United States Patent
Wedekind et al.

(10) Patent No.: US 10,980,451 B2
(45) Date of Patent: *Apr. 20, 2021

(54) SYSTEMS AND METHODS FOR DISPLAY DEVICE AND SENSOR ELECTRONICS UNIT COMMUNICATION

(71) Applicant: DexCom, Inc., San Diego, CA (US)

(72) Inventors: Jeffrey R. Wedekind, San Diego, CA (US); Douglas William Burnette, San Diego, CA (US); Aditya Mandapaka, San Diego, CA (US); Zebediah L. McDaniel, San Diego, CA (US); Peter C. Simpson, Cardiff, CA (US); Arturo Garcia, Chula Vista, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/027,418

(22) Filed: Sep. 21, 2020

(65) Prior Publication Data

US 2021/0007644 A1 Jan. 14, 2021

Related U.S. Application Data

(63) Continuation of application No. 16/556,144, filed on Aug. 29, 2019, now Pat. No. 10,799,157, which is a
(Continued)

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/0004* (2013.01); *A61B 5/0015* (2013.01);
(Continued)

(58) Field of Classification Search
CPC ............ A61B 5/14532; A61B 5/14865; A61B 5/7275; A61B 5/742; A61B 5/0004;
(Continued)

(56) References Cited

U.S. PATENT DOCUMENTS

| 612,939 A | 10/1898 | Willson, Jr. |
| 4,757,022 A | 7/1988 | Shults et al. |

(Continued)

FOREIGN PATENT DOCUMENTS

| EP | 2453398 A1 | 5/2012 |
| EP | 2498196 A2 | 9/2012 |

(Continued)

OTHER PUBLICATIONS

Anonymous, "Near Field Communication—Wikipedia, The Free Encyclopedia," Retrieved from https://en.wikipedia.org/w/index.php?title=Near_field_communication&%20oldid=543740757, Jun. 27, 2014, 15 pages.

(Continued)

*Primary Examiner* — Christian Jang
(74) *Attorney, Agent, or Firm* — Knobbe Martens Olson & Bear LLP

(57) ABSTRACT

Methods and apparatus are provided for communication among display devices and sensor electronics unit in an analyte monitoring system. The analyte monitoring system may include a sensor that is configured to perform measurements indicative of analyte levels. The sensor may be communicatively coupled to the sensor electronics unit. The sensor electronics unit may be configured to transmit data indicative of analyte levels to the display devices using one or more communication protocols. Furthermore, the sensor electronics unit may be configured to operate in multiple modes, and switch between the modes in response to com- (Continued)

mands received from the display devices. Related systems, methods, and articles of manufacture are also described.

16 Claims, 28 Drawing Sheets

Related U.S. Application Data continuation of application No. 15/471,374, filed on Mar. 28, 2017, now Pat. No. 10,561,349.

(60) Provisional application No. 62/315,976, filed on Mar. 31, 2016.

(51) Int. Cl.
  *H04L 29/06* (2006.01)
  *A61B 5/1486* (2006.01)
  *G16H 40/60* (2018.01)
  *G16H 10/60* (2018.01)
  *A61B 5/11* (2006.01)
  *G16H 40/63* (2018.01)
  *G16H 40/67* (2018.01)
  *G16H 10/40* (2018.01)
  *H04L 29/08* (2006.01)

(52) U.S. Cl.
  CPC .......... *A61B 5/0022* (2013.01); *A61B 5/1116* (2013.01); *A61B 5/14546* (2013.01); *A61B 5/14865* (2013.01); *A61B 5/4839* (2013.01); *A61B 5/7275* (2013.01); *A61B 5/7278* (2013.01); *A61B 5/742* (2013.01); *A61B 5/743* (2013.01); *A61B 5/746* (2013.01); *A61B 5/7475* (2013.01); *G16H 10/40* (2018.01); *G16H 10/60* (2018.01); *G16H 40/60* (2018.01); *G16H 40/63* (2018.01); *G16H 40/67* (2018.01); *H04L 69/18* (2013.01); *A61B 5/6898* (2013.01); *A61B 2560/0209* (2013.01); *A61B 2560/0223* (2013.01); *A61B 2560/0252* (2013.01); *A61B 2562/0219* (2013.01); *H04L 67/12* (2013.01); *Y02A 90/10* (2018.01)

(58) Field of Classification Search
  CPC ..... A61B 5/7278; A61B 5/0022; A61B 5/743; A61B 5/14546; A61B 5/7475; A61B 5/746; A61B 5/4839; A61B 5/1116; A61B 5/0015; A61B 2560/0209; A61B 2562/0219; A61B 2560/0252; A61B 5/6898; A61B 2560/0223; G16H 40/60; G16H 40/63; G16H 40/67; G16H 10/60; H04L 67/12; H04L 69/18; Y02A 90/10
  See application file for complete search history.

(56) References Cited

U.S. PATENT DOCUMENTS

| | | |
|---|---|---|
| 4,994,167 A | 2/1991 | Shults et al. |
| 6,001,067 A | 12/1999 | Shults et al. |
| 6,234,964 B1 | 5/2001 | Iliff |
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,558,321 B1 | 5/2003 | Burd et al. |
| 6,565,509 B1 | 5/2003 | Say et al. |
| 6,579,690 B1 | 6/2003 | Bonnecaze et al. |
| 6,585,644 B2 | 7/2003 | Lebel et al. |
| 6,702,857 B2 | 3/2004 | Brauker et al. |
| 6,741,877 B1 | 5/2004 | Shults et al. |
| 6,862,465 B2 | 3/2005 | Shults et al. |
| 6,931,327 B2 | 8/2005 | Goode, Jr. et al. |
| 6,950,708 B2 | 9/2005 | Bowman, IV et al. |
| 6,958,705 B2 | 10/2005 | Lebel et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,192,450 B2 | 3/2007 | Brauker et al. |
| 7,226,978 B2 | 6/2007 | Tapsak et al. |
| 7,276,029 B2 | 10/2007 | Goode, Jr. et al. |
| 7,310,544 B2 | 12/2007 | Brister et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,430 B2 | 4/2009 | Von Arx et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,761,130 B2 | 7/2010 | Simpson et al. |
| 7,771,352 B2 | 8/2010 | Shults et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,792,562 B2 | 9/2010 | Shults et al. |
| 7,797,028 B2 | 9/2010 | Goode, Jr. et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode et al. |
| 7,927,274 B2 | 4/2011 | Rasdal et al. |
| 7,933,639 B2 | 4/2011 | Goode et al. |
| 7,935,057 B2 | 5/2011 | Goode, Jr. et al. |
| 7,946,984 B2 | 5/2011 | Brister et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |

(56) References Cited

U.S. PATENT DOCUMENTS

| | | |
|---|---|---|
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,008 B2 | 12/2011 | Mehta et al. |
| 8,073,519 B2 | 12/2011 | Goode, Jr. et al. |
| 8,073,520 B2 | 12/2011 | Kamath et al. |
| 8,095,692 B2 | 1/2012 | Mehta et al. |
| 8,112,240 B2 | 2/2012 | Fennell |
| 8,118,877 B2 | 2/2012 | Brauker et al. |
| 8,121,857 B2 | 2/2012 | Galasso et al. |
| 8,128,562 B2 | 3/2012 | Goode, Jr. et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,180,591 B2 | 5/2012 | Yuen et al. |
| 8,195,265 B2 | 6/2012 | Goode, Jr. et al. |
| 8,206,297 B2 | 6/2012 | Kamath et al. |
| 8,208,973 B2 | 6/2012 | Mehta |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,298,142 B2 | 10/2012 | Simpson et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,332,008 B2 | 12/2012 | Goode et al. |
| 8,346,338 B2 | 1/2013 | Goode, Jr. et al. |
| 8,364,229 B2 | 1/2013 | Simpson et al. |
| 8,369,919 B2 | 2/2013 | Kamath et al. |
| 8,374,667 B2 | 2/2013 | Brauker et al. |
| 8,386,004 B2 | 2/2013 | Kamath et al. |
| 8,394,021 B2 | 3/2013 | Goode et al. |
| 8,412,185 B2 | 4/2013 | Cader et al. |
| 8,432,260 B2 | 4/2013 | Talty et al. |
| 8,527,025 B1 | 9/2013 | Shults et al. |
| 8,549,600 B2 | 10/2013 | Shedrinsky |
| 8,638,397 B2 | 1/2014 | Ueno et al. |
| 8,926,509 B2 | 1/2015 | Magar et al. |
| 8,968,198 B2 | 3/2015 | Brauker et al. |
| 9,011,332 B2 | 4/2015 | Heller et al. |
| 9,028,410 B2 | 5/2015 | San Vicente et al. |
| 9,232,916 B2 | 1/2016 | Mao et al. |
| 9,445,445 B2 | 9/2016 | Miller et al. |
| 9,451,910 B2 | 9/2016 | Brister et al. |
| 9,532,737 B2 | 1/2017 | Karan et al. |
| 9,579,053 B2 | 2/2017 | Brister et al. |
| 9,662,438 B2 | 5/2017 | Kamen et al. |
| 9,668,682 B2 | 6/2017 | Brister et al. |
| 9,681,807 B2 | 6/2017 | Miller et al. |
| 9,724,028 B2 | 8/2017 | Brauker et al. |
| 9,788,354 B2 | 10/2017 | Miller et al. |
| 9,788,766 B2 | 10/2017 | Simpson et al. |
| 9,801,541 B2 | 10/2017 | Mensinger et al. |
| 9,931,036 B2 | 4/2018 | Miller et al. |
| 9,931,037 B2 | 4/2018 | Miller et al. |
| 9,999,379 B2 | 6/2018 | Hernandez-Rosas et al. |
| 1,037,618 A1 | 8/2019 | Simpson; Peter C et al. |
| 1,056,134 A1 | 2/2020 | Wedekind; Jeffrey R et al. |
| 1,056,855 A1 | 2/2020 | Wedekind; Jeffrey R et al. |
| 2002/0045808 A1 | 4/2002 | Ford et al. |
| 2002/0065453 A1 | 5/2002 | Lesho et al. |
| 2002/0195997 A1 | 12/2002 | Peek et al. |
| 2003/0028184 A1 | 2/2003 | Lebel et al. |
| 2003/0032874 A1 | 2/2003 | Rhodes et al. |
| 2003/0060692 A1 | 3/2003 | L Ruchti et al. |
| 2004/0044272 A1 | 3/2004 | Moerman et al. |
| 2005/0023137 A1 | 2/2005 | Bhullar et al. |
| 2005/0027462 A1 | 2/2005 | Goode, Jr. et al. |
| 2005/0027463 A1 | 2/2005 | Goode, Jr. et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0051427 A1 | 3/2005 | Brauker et al. |
| 2005/0056552 A1 | 3/2005 | Simpson et al. |
| 2005/0090607 A1 | 4/2005 | Tapsak et al. |
| 2005/0154271 A1 | 7/2005 | Rasdal et al. |
| 2005/0176136 A1 | 8/2005 | Burd et al. |
| 2005/0182451 A1 | 8/2005 | Griffin et al. |
| 2005/0192557 A1 | 9/2005 | Brauker et al. |
| 2005/0203360 A1 | 9/2005 | Brauker et al. |
| 2005/0245799 A1 | 11/2005 | Brauker et al. |
| 2005/0283208 A1 | 12/2005 | Von Arx et al. |
| 2006/0015020 A1 | 1/2006 | Neale et al. |
| 2006/0016700 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036143 A1 | 2/2006 | Brister et al. |
| 2006/0036144 A1 | 2/2006 | Brister et al. |
| 2006/0040402 A1 | 2/2006 | Brauker et al. |
| 2006/0068208 A1 | 3/2006 | Tapsak et al. |
| 2006/0142651 A1 | 6/2006 | Brister et al. |
| 2006/0155180 A1 | 7/2006 | Brister et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0224108 A1 | 10/2006 | Brauker et al. |
| 2006/0226985 A1 | 10/2006 | Goodnow et al. |
| 2006/0235285 A1 | 10/2006 | Brister et al. |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0257995 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2006/0290496 A1 | 12/2006 | Peeters |
| 2007/0016381 A1 | 1/2007 | Kamath et al. |
| 2007/0027370 A1 | 2/2007 | Brauker et al. |
| 2007/0027385 A1 | 2/2007 | Brister et al. |
| 2007/0032706 A1 | 2/2007 | Kamath et al. |

(56) References Cited

U.S. PATENT DOCUMENTS

| | | |
|---|---|---|
| 2007/0032718 A1 | 2/2007 | Shults et al. |
| 2007/0045902 A1 | 3/2007 | Brauker et al. |
| 2007/0059196 A1 | 3/2007 | Brister et al. |
| 2007/0060093 A1 | 3/2007 | Kerth et al. |
| 2007/0060132 A1 | 3/2007 | Wilhelmsson et al. |
| 2007/0066873 A1 | 3/2007 | Kamath et al. |
| 2007/0108245 A1 | 5/2007 | Ferman et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0203966 A1 | 8/2007 | Brauker et al. |
| 2007/0208245 A1 | 9/2007 | Brauker et al. |
| 2007/0208246 A1 | 9/2007 | Brauker et al. |
| 2007/0232879 A1 | 10/2007 | Brister et al. |
| 2007/0253021 A1 | 11/2007 | Mehta et al. |
| 2007/0255116 A1 | 11/2007 | Mehta et al. |
| 2007/0255352 A1 | 11/2007 | Roline et al. |
| 2007/0293742 A1 | 12/2007 | Simonsen et al. |
| 2008/0033254 A1 | 2/2008 | Kamath et al. |
| 2008/0045824 A1 | 2/2008 | Tapsak et al. |
| 2008/0083617 A1 | 4/2008 | Simpson et al. |
| 2008/0086044 A1 | 4/2008 | Brister et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194938 A1 | 8/2008 | Brister et al. |
| 2008/0197024 A1 | 8/2008 | Simpson et al. |
| 2008/0199894 A1 | 8/2008 | Galasso |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0262533 A1 | 10/2008 | McEwen et al. |
| 2008/0275313 A1 | 11/2008 | Brister et al. |
| 2008/0287765 A1 | 11/2008 | Rasdal et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0045055 A1 | 2/2009 | Rhodes et al. |
| 2009/0054737 A1 | 2/2009 | Magar et al. |
| 2009/0062633 A1 | 3/2009 | Brauker et al. |
| 2009/0062635 A1 | 3/2009 | Brauker et al. |
| 2009/0076360 A1* | 3/2009 | Brister .................. G16Z 99/00 600/365 |
| 2009/0085768 A1 | 4/2009 | Patel et al. |
| 2009/0099436 A1 | 4/2009 | Brister et al. |
| 2009/0124877 A1 | 5/2009 | Goode, Jr. et al. |
| 2009/0124879 A1 | 5/2009 | Brister et al. |
| 2009/0124964 A1 | 5/2009 | Leach et al. |
| 2009/0131769 A1 | 5/2009 | Leach et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0171180 A1 | 7/2009 | Pering et al. |
| 2009/0178459 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192751 A1 | 7/2009 | Kamath et al. |
| 2009/0203981 A1 | 8/2009 | Brauker et al. |
| 2009/0216103 A1 | 8/2009 | Brister et al. |
| 2009/0240120 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287074 A1 | 11/2009 | Shults et al. |
| 2009/0289507 A1 | 11/2009 | Shiu |
| 2009/0291634 A1 | 11/2009 | Saarisalo |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0026250 A1 | 2/2010 | Petty |
| 2010/0030484 A1 | 2/2010 | Brauker et al. |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0094111 A1 | 4/2010 | Heller et al. |
| 2010/0096259 A1 | 4/2010 | Zhang et al. |
| 2010/0121169 A1 | 5/2010 | Petisce et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191082 A1 | 7/2010 | Brister et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0212583 A1 | 8/2010 | Brister et al. |
| 2010/0216507 A1 | 8/2010 | Maeda |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |

(56) References Cited

U.S. PATENT DOCUMENTS

| | | |
|---|---|---|
| 2010/0240976 A1 | 9/2010 | Goode, Jr. et al. |
| 2010/0261987 A1 | 10/2010 | Kamath et al. |
| 2010/0274107 A1 | 10/2010 | Boock et al. |
| 2010/0280341 A1 | 11/2010 | Boock et al. |
| 2010/0283917 A1 | 11/2010 | Ueno et al. |
| 2010/0286496 A1 | 11/2010 | Simpson et al. |
| 2010/0292556 A1 | 11/2010 | Golden |
| 2010/0298684 A1 | 11/2010 | Leach et al. |
| 2010/0323431 A1 | 12/2010 | Rutkowski et al. |
| 2010/0324403 A1 | 12/2010 | Brister et al. |
| 2010/0331644 A1 | 12/2010 | Neale et al. |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009272 A1 | 1/2011 | Wattebled et al. |
| 2011/0009727 A1 | 1/2011 | Mensinger et al. |
| 2011/0019824 A1 | 1/2011 | Sattiraju et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0054282 A1 | 3/2011 | Nekoomaram et al. |
| 2011/0058485 A1 | 3/2011 | Sloan |
| 2011/0060530 A1 | 3/2011 | Fennell |
| 2011/0065384 A1 | 3/2011 | Cader et al. |
| 2011/0077490 A1 | 3/2011 | Simpson et al. |
| 2011/0118579 A1 | 5/2011 | Goode, Jr. et al. |
| 2011/0124992 A1 | 5/2011 | Brauker et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0178378 A1 | 7/2011 | Brister et al. |
| 2011/0190614 A1 | 8/2011 | Brister et al. |
| 2011/0201898 A1 | 8/2011 | Benco et al. |
| 2011/0201910 A1 | 8/2011 | Rasdal et al. |
| 2011/0201911 A1 | 8/2011 | Johnson et al. |
| 2011/0210830 A1 | 9/2011 | Talty et al. |
| 2011/0218414 A1 | 9/2011 | Kamath et al. |
| 2011/0221590 A1 | 9/2011 | Baker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0263958 A1 | 10/2011 | Brauker et al. |
| 2011/0264035 A1 | 10/2011 | Yodfat et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0084053 A1 | 4/2012 | Yuen et al. |
| 2012/0108934 A1 | 5/2012 | Valdes et al. |
| 2012/0130214 A1 | 5/2012 | Brister et al. |
| 2012/0172691 A1 | 7/2012 | Brauker et al. |
| 2012/0179014 A1 | 7/2012 | Shults et al. |
| 2012/0182939 A1 | 7/2012 | Rajan et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0216507 A1 | 8/2012 | Nieuwstadt |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0233679 A1 | 9/2012 | Shedrinsky |
| 2012/0235823 A1 | 9/2012 | Trock et al. |
| 2012/0238851 A1 | 9/2012 | Kamen et al. |
| 2012/0238852 A1 | 9/2012 | Brauker et al. |
| 2012/0245447 A1 | 9/2012 | Karan et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |
| 2012/0296311 A1 | 11/2012 | Brauker et al. |
| 2012/0302854 A1 | 11/2012 | Kamath et al. |
| 2012/0302855 A1 | 11/2012 | Kamath et al. |
| 2012/0309302 A1 | 12/2012 | Buhot |
| 2012/0317194 A1 | 12/2012 | Tian |
| 2012/0323100 A1 | 12/2012 | Kamath et al. |
| 2013/0012798 A1 | 1/2013 | Brister et al. |
| 2013/0030273 A1 | 1/2013 | Tapsak et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0053666 A1 | 2/2013 | Hughes et al. |
| 2013/0137946 A1 | 5/2013 | Geske et al. |
| 2013/0172709 A1 | 7/2013 | Mears et al. |
| 2013/0203351 A1 | 8/2013 | Hillan et al. |
| 2013/0321425 A1 | 12/2013 | Greene et al. |
| 2013/0326495 A1 | 12/2013 | Reunamaki et al. |
| 2014/0176338 A1 | 6/2014 | He et al. |
| 2014/0184422 A1 | 7/2014 | Mensinger et al. |
| 2014/0235166 A1 | 8/2014 | Molettiere et al. |
| 2014/0266776 A1 | 9/2014 | Miller et al. |
| 2014/0276419 A1 | 9/2014 | Rosinko et al. |
| 2014/0288402 A1 | 9/2014 | Brister et al. |
| 2016/0066826 A1 | 3/2016 | Larvenz et al. |
| 2016/0081586 A1 | 3/2016 | Miller et al. |
| 2017/0135041 A1 | 5/2017 | Miller et al. |
| 2017/0231497 A1 | 8/2017 | Brister et al. |
| 2017/0281000 A1 | 10/2017 | Wedekind et al. |
| 2017/0281060 A1 | 10/2017 | Wedekind et al. |
| 2018/0132720 A1 | 5/2018 | Miller et al. |
| 2018/0160949 A1 | 6/2018 | Brister et al. |
| 2019/0059730 A1 | 2/2019 | Brister et al. |
| 2019/0069817 A1 | 3/2019 | Brister et al. |
| 2019/0380163 A1 | 12/2019 | Miller et al. |
| 2020/0008721 A1 | 1/2020 | Wedekind et al. |
| 2020/0008722 A1 | 1/2020 | Wedekind et al. |
| 2020/0093407 A1 | 3/2020 | Miller et al. |
| 2020/0214565 A1 | 7/2020 | Miller et al. |
| 2020/0343941 A1 | 10/2020 | Miller et al. |

FOREIGN PATENT DOCUMENTS

| | | |
|---|---|---|
| WO | WO-9718639 A1 | 5/1997 |
| WO | WO-2013019225 A1 | 2/2013 |

OTHER PUBLICATIONS

File History of European Application No. 14708172.3 filed on Jun. 16, 2015, including Opposition documents for U.S. Pat. No. 2,973,082 (Appl. No. EP14708172.3), 1179 pages.

(56) References Cited

OTHER PUBLICATIONS

International Preliminary Report on Patentability for Application No. PCT/US2017/024557 dated Oct. 11, 2018, 8 pages.
International Search Report and Written Opinion for Application No. PCT/US2017/024557 dated Jul. 27, 2017, 10 pages.
Wikipedia, "Near-Field Communication," downloaded from https://en.wikipedia.org/wiki/Near-field_commucation on Jan. 3, 2019, pp. 1-14.
Decuir J., "Bluetooth 4.0: Low Energy," IEEE SCV Consultants' Network of Silicon Valley, May 15, 2012, 60 pages.
Dementyev A., et al., "Power Consumption Analysis of Bluetooth Low Energy, Zig Bee and ANT Sensor Nodes in a Cyclic Sleep Scenario," Apr. 2013, 5 pages.
Extended European Search Report for Application No. 18175412.8 dated Oct. 17, 2018, 11 pages.
International Preliminary Report on Patentability for Application No. PCT/US2014/016111 dated Sep. 24, 2015, 10 pages.
International Search Report and Written Opinion for Application No. PCT/US2014/016111 dated Dec. 22, 2014, 13 pages.
Kwak K.S., et al., "A Traffic-adaptive MAC Protocol for WBAN," IEEE Globecom 2020 Workshop on Mobile Computing and Emerging Communication Networks, 2010, pp. 1286-1289.
Mirano Systems Inc, "Green Receipt," Retrieved from https://web.archive.org/web/20121224003730/http://mirano.ca/, 2012, 1 page.
NFC Forum, "NFC Data Exchange Format (NDEF)," NFCForum-TS-NDEF 1.0, Technical Specification, NFC Forum™, NDEF 1.0, Jul. 24, 2006, 25 pages.
NFCForum, NFCForum-TS-DigitalProtocol-1.0, 2010; 194 pages.
Office Action from Australian Patent Application No. 2020202301, dated Jun. 26, 2020, 3 pages.
Office Action from Canadian Patent Application No. 3007516 dated Oct. 23, 2020, 4 pages.
Office Action from European Patent Application No. 17776465.1, dated Sep. 3, 2020, 130 pages.
Specification of the Bluetooth 4.0, Jun. 30, 2010, 2302 pages.
Townsend k., et al., "Getting Started with Bluetooth Low Energy," Chapter 1, Released May 2014, O'Reilly Media, Inc, 26 pages.
Ullah N., et al., "A Very Low Power Mac (VLPM) Protocol for Wireless Body Area Networks," Sensors, Mar. 25, 2011, pp. 3717-3737.

* cited by examiner

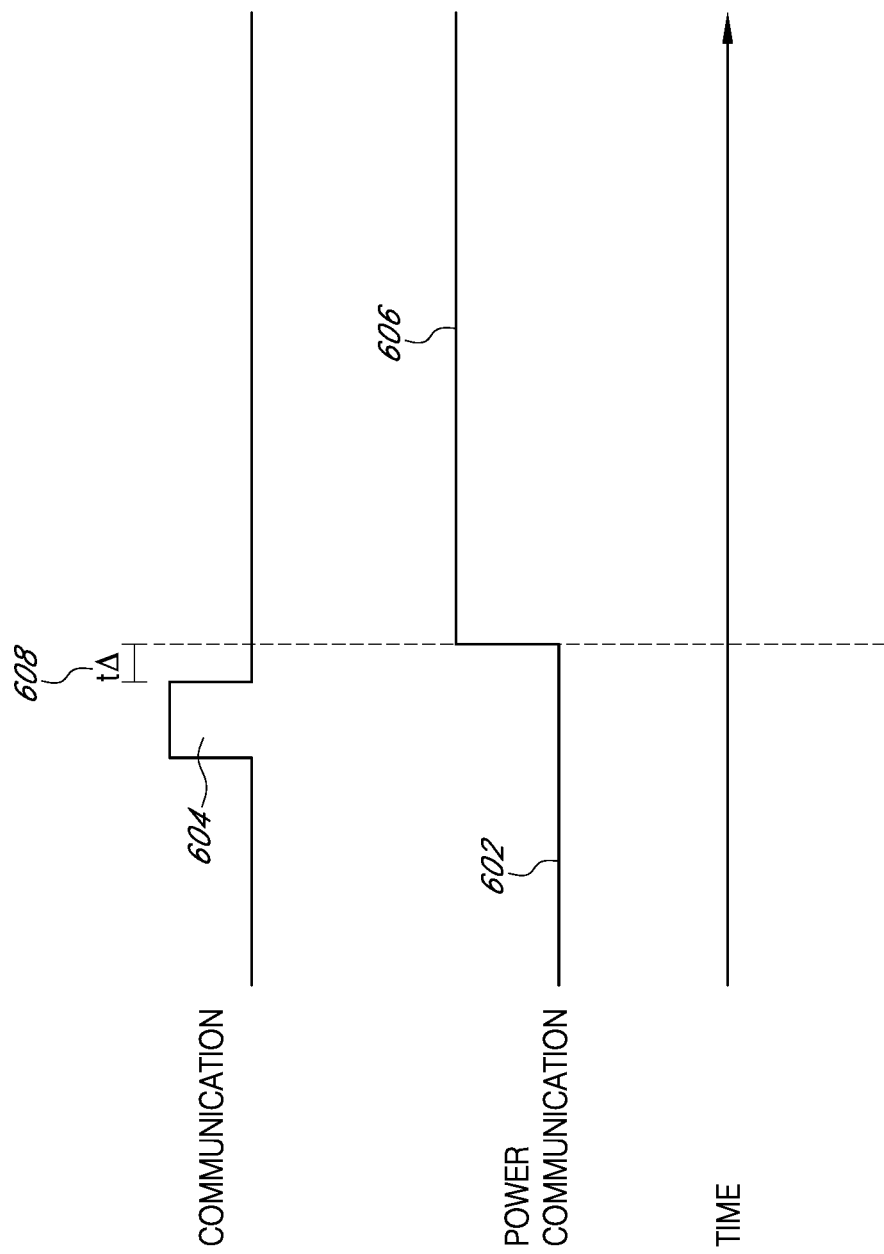

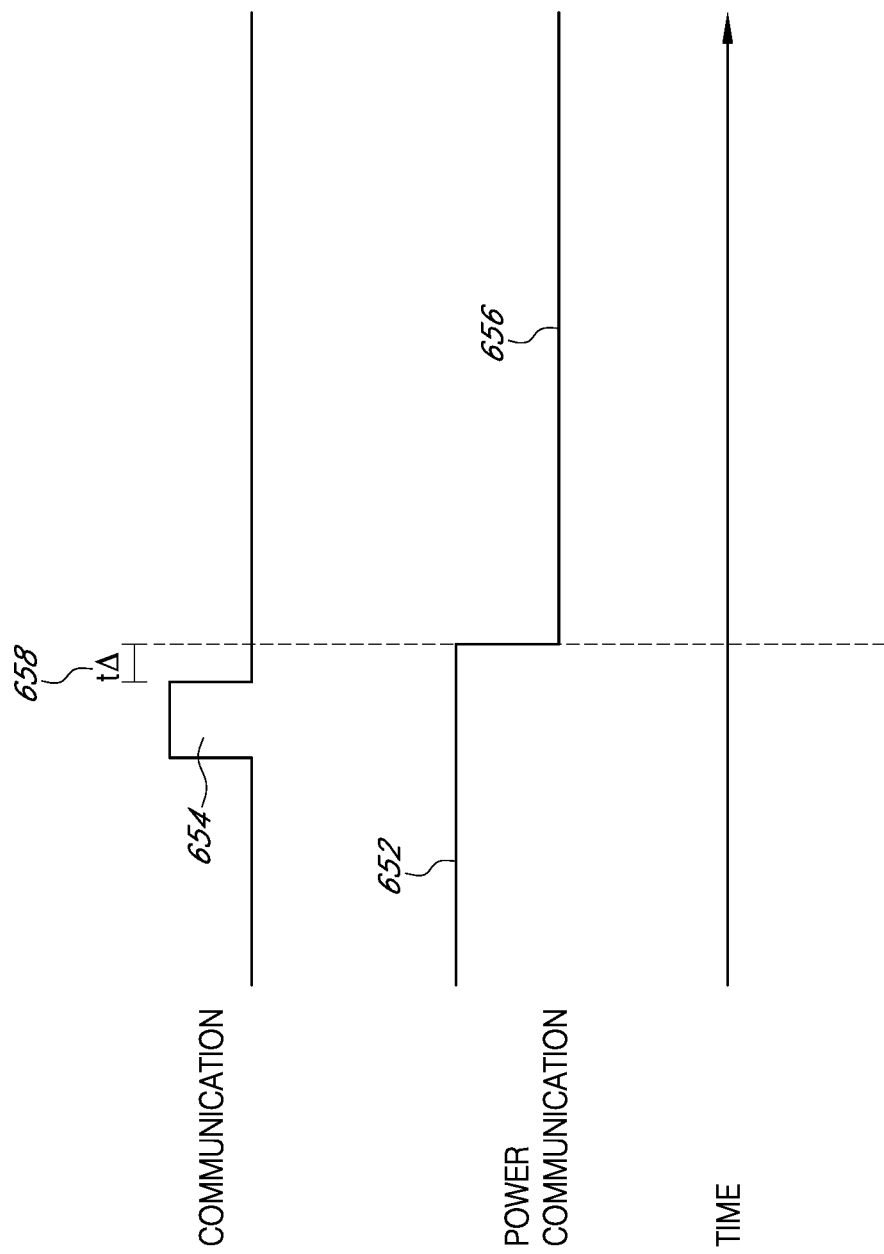

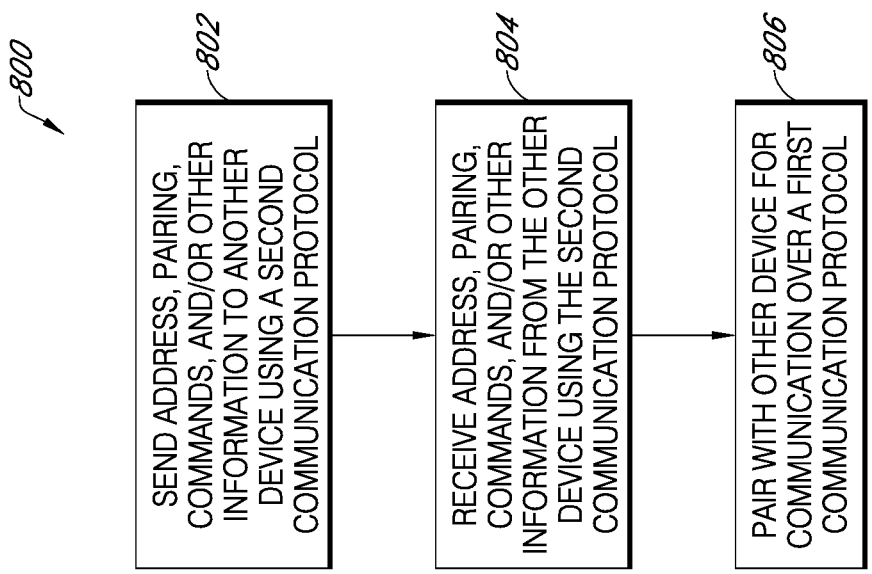

SYSTEMS AND METHODS FOR DISPLAY DEVICE AND SENSOR ELECTRONICS UNIT COMMUNICATION

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 16/556,144, filed Aug. 29, 2019, which is a continuation of U.S. application Ser. No. 15/471,374, filed Mar. 28, 2017, now U.S. Pat. No. 10,561,349, which claims the benefit of U.S. Provisional Application No. 62/315,976, filed on Mar. 31, 2016. Each of the aforementioned applications is incorporated by reference herein in its entirety, and each is hereby expressly made a part of this specification.

FIELD

The present application relates generally to systems and methods for communications between a sensor electronics unit and a display device of an analyte monitoring system.

BACKGROUND

Analyte monitors can be configured to mount on tissue to detect analytes in a sensing area. For example, and without limitation, analyte monitors can include sensors that measure the concentration of glucose, lactate, cholesterol, hemoglobin, and/or other blood or bodily fluid constituents.

In some cases, persons with diabetes mellitus (also known as diabetes) can use an analyte monitor. Diabetes is a disorder in which the pancreas of a person may not create sufficient insulin, such as in the case of Type I diabetes, and/or in which insulin may not be effective for a person, such as is in the case of Type II diabetes. In a diabetic state, a victim can suffer from high blood sugar, which can cause an array of physiological derangements, such as kidney failure, skin ulcers, or bleeding into the vitreous of the eye, which can be associated with the deterioration of small blood vessels. A hypoglycemic reaction, such as low blood sugar, can be induced by an inadvertent overdose of insulin, or after a normal dose of insulin or glucose-lowering agent accompanied by extraordinary exercise or insufficient food intake.

In some cases, a diabetic can carry an analyte monitor such as a self-monitoring blood glucose ("SMBG") monitor, which typically can utilize uncomfortable finger pricking methods. Due to the lack of comfort and/or convenience, a diabetic typically measures his or her glucose level only two to four times per day. Unfortunately, these time intervals can be spread so far apart that the diabetic would likely find out too late that he/she has a hyperglycemic or hypoglycemic condition, which can sometimes cause dangerous side effects. In fact, it is not only unlikely that a diabetic would take a timely SMBG value, but additionally, the diabetic would likely not know if his/her blood glucose value is rising or falling based on conventional methods.

Consequently, a variety of analyte monitors are being developed to include non-invasive, transdermal (e.g., transcutaneous), and/or implantable electrochemical sensors for continuously detecting and/or quantifying blood glucose values. These, as well as other types of devices, generally transmit raw or processed data to remote devices, which can include a display, to allow presentation of information to a user hosting the sensor.

SUMMARY

Any of the features of aspects specified herein are applicable to all other aspects and implementations identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

In some implementations, a plurality of communication protocols can be used for communication between a sensor electronics unit and one or more display devices. The communication between the sensor electronics unit can be based on wired and/or wireless communication protocols, which will be discussed later in this disclosure with reference to FIGS. 3-4, as well as elsewhere throughout this disclosure. For example, and without limitation, a first communication protocol can utilize radio transmission, such as BLUETOOTH®, or Bluetooth Low Energy (BLE) wireless communication protocol, which uses a radio transmission frequency range 2.4 to 2.485 GHz. A second communication protocol can utilize a radio frequency ("RF") field, such as near field communication ("NFC") or radio frequency identification ("RFID"). NFC can be an RF field with a 13.56 MHz frequency. RFID can operate in a range of frequency bands, such as, without limitation, 120-150 kHz, 13.56 MHz, 433 MHz, 865-868 MHz, 902-928 MHz, 2450-5800 MHz, 3.1-10 GHz.

In some implementations, the second communication protocol can be used by a display device to communicate with a sensor electronics unit. In some cases, these communications can include commands/requests, transmissions of data, and/or other communications.

In some implementations, the display device can utilize the second communication protocol to cause the sensor electronics unit to perform one or more actions. In some cases, these actions can be combined in an action queue. Accordingly, the actions described in various implementations in this disclosure can be combined and performed in a sequence of actions. These various actions, and their functional units, will be discussed later in this disclosure with reference to FIGS. 5C, 6A-B, as well as elsewhere throughout this disclosure.

In some implementations, one action can be a wake action, where the display device uses the second communication protocol to send commands/requests and/or data to wake up a sensor electronics unit from a shelf mode, idle mode, and/or any low power mode. In some cases, after the sensor electronics unit wakes, it can pair and communicate using the first communication protocol with the display device that was used to wake the sensor electronics unit. Similarly, the second communication protocol can be used to change the mode of operation of the sensor electronics unit, such as changing it to shelf mode, idle mode, low power mode, normal mode, high speed mode, and/or any mode that may be desirable for the sensor electronics unit.

In some embodiments, an analyte level monitoring system including an analyte sensor for measuring analyte levels and communicatively coupled to a sensor electronics unit is provided. The sensor electronics unit is configured to receive analyte measurement data from the sensor and may be further configured to process the data to calculate estimated analyte values based on the measurement data. The sensor electronics unit is also configured to communicate with a display device using a plurality of communication protocols and to operate in a plurality of operational modes. For example, and without limitation, modes of operation may include a normal power mode and a low power mode. The display device is configured to communicate commands to the sensor electronics unit using at least one of the plurality of communication protocols. For instance the commands may include one or more commands which, upon receipt by the sensor electronics unit, cause the sensor electronics unit to switch from a low power mode, such as a storage mode, to a normal power mode and/or wirelessly connect to the display device using a communication protocol different from the one used to communicate the command. Alternatively, the sensor electronics unit may switch from a normal power mode to a low power mode and/or terminate a connection for communication with the display device using a first communication protocol in response to a command communicated using a second communication protocol. The sensor electronics unit may communicate data indicative of analyte levels, such as analyte measurement data or estimated analyte values, to the display device using at least one of the plurality of communication protocols, for instance while operating in the normal power mode. In some of these embodiments, the display device is configured to process analyte measurement data to calculate estimated analyte values.

In other embodiments, an analyte monitoring system comprises an analyte sensor for measuring analyte levels and communicatively coupled to a sensor electronics unit. The sensor electronics unit is configured to receive analyte measurement data from the sensor and may be further configured to process the data to calculate estimated analyte values based on the measurement data. The sensor electronics unit is also configured to communicate with a display device using a plurality of communication protocols. The sensor electronics unit may communicate analyte measurement data or estimated analyte values to the display device using a first communication protocol. In some of these embodiments, the display device is configured to process analyte measurement data to calculate estimated analyte values. The display device is also configured to communicate commands to the sensor electronics unit using a second communication protocol. For instance, upon receipt of the commands by the sensor electronics unit, the sensor electronics unit may cease to perform analyte measurements, and further cease to transmit analyte measurement data or estimated analyte values.

In some embodiments, an analyte level monitoring system including an analyte sensor for measuring analyte levels and communicatively coupled to a sensor electronics unit is provided. The sensor electronics unit is configured to receive analyte measurement data from the sensor and may be further configured to process the data to calculate estimated analyte values based on the measurement data. The sensor electronics unit is also configured to communicate with a display device using a plurality of communication protocols. The sensor electronics unit may communicate analyte measurement data or estimated analyte values to the display device at a predefined time using a first communication protocol. The sensor electronics unit may further be configured to communicate analyte measurement data or estimated analyte values from before the predefined time to the display device using a second communication protocol. In some of these embodiments, the display device is configured to process analyte measurement data to calculate estimated analyte values.

In other embodiments, an analyte monitoring system comprises an analyte sensor for measuring analyte levels and communicatively coupled to a sensor electronics unit. The sensor electronics unit is configured to receive analyte measurement data from the sensor and may be further configured to process the data to calculate estimated analyte values based on the measurement data. The sensor electronics unit is also configured to communicate with a display device using a plurality of communication protocols. The sensor electronics unit may communicate analyte measurement data or estimated analyte values to the display device using a first communication protocol. In some of these embodiments, the display device is configured to process analyte measurement data to calculate estimated analyte values. The display device is also configured to communicate commands to the sensor electronics unit using a second communication protocol. For instance the commands may include one or more instructions which, upon receipt by the sensor electronics unit, cause the sensor electronics unit to transmit analyte measurement data or estimated analyte values using the first communication protocol in response to the data request command sent using the second communication protocol. Alternatively a portion of the analyte data or values may be communicated using the first communication protocol, and another portion of the analyte data or values may be communicated using a different communication protocol.

In some implementations, one action can be a calibrate action, where the display device uses the second communication protocol to send commands/requests and/or data to transmit calibration data to the sensor electronics unit and calibrate the sensor electronics unit. This calibration data can include data obtained by a user through finger pricking and entered onto a display device. The calibration data can be used by the sensor electronics unit to calibrate its calibration function that converts the raw measurements (e.g., currents, voltages, resistances, gate logic, etc.) of an analyte sensor into data indicative of analyte measurements, such as estimated glucose values ("EGVs"), estimated blood glucose levels, blood glucose levels, and/or any other analyte measurement or estimation of an analyte measurement.

In some implementations, one action can be a clone action where the display device can use the second communication protocol to send commands/requests and/or data that clones the sensor electronics unit. For example, and without limitation, two sensor electronics units can be used in a cloning action. The display device can send commands/requests to a first sensor electronics unit using the second communication protocol to send a portion or all of the stored data of the first sensor electronics unit (e.g., white lists, bonding lists, calibration data, analyte measurements, raw sensor measurements, etc.) to the display device over the first communication protocol or the second communication protocol. The display device can then use the second communication protocol to then initiate a transfer of the data it obtained from the first sensor electronics unit to the second sensor electronics unit.

In some implementations, one action can be a retrieve data action where the display device can use the second communication protocol to send commands/requests and/or data that causes the sensor electronics unit to send data to the display device using the first communication protocol and/or the second communication protocol. For example, and without limitation, NFC-capable or RFID-capable display devices may alter the normal establishment of communications, such as scheduled communications or communications following a particular timing as described later in this disclosure with reference to FIG. 7A-E and elsewhere throughout this disclosure. For example, and without limitation, a user may wish to have a sensor electronics unit transmit sensor information prior to a scheduled transmission. This transmission can be due to the user/host feeling the onset of a hypoglycemic condition, or the user may wish to have a backlog of sensor data transmitted in a bulk transfer to a display device.

In some implementations, one action can be a set white/bonding list action where the display device uses the second communication protocol to send commands/requests and/or data that sets, adjusts, and/or manipulates the white list or bonding list of the first communication protocol in the sensor electronics unit. White lists and bonding lists will be discussed in more detail later in this disclosure with reference to FIGS. 5C, 6A-B, 9A-F, as well as elsewhere throughout this disclosure. This action can include adding display devices to the white list or bonding list, removing display devices from the white list or bonding list, and/or rearranging the white list and/or bonding list. In some implementations, adding the display device can transmit over the second communication protocol command(s) that add that display device to the sensor electronic unit's white list for the first communication protocol, where the command(s) can also designate the position of the display device, and other display devices, on that white list, and can shift other display devices off the white list.

In some implementations, one action can be to start or stop a sensor session, where the display device uses the second communication protocol to send commands/requests and/or data that causes the sensor electronics unit to start or stop sensor measurements and/or transmissions.

In some implementations, a plurality of communication protocols (e.g., the first and second communication protocol) can be used to send data and/or commands. For example, and without limitation, certain types of communications can be transmitted over the first communication protocol and certain types of communications can be transmitted over the second communication protocol. By way of illustration, and without limitation, all commands can be sent over the second communication protocol and all data can be sent over the first communication protocol. In some implementations, communications can be split between the first communication protocol and the second communication protocol. For example, and without limitation, encrypted data/information can be sent over one communication protocol whereas the decryption key and/or other security information can be sent over another communication protocol so that a display device uses both communication protocols to be able to read communications from a sensor electronics unit. In some implementations, communications can be split between a plurality communication protocols so that a complete message comprises data/information from the plurality of communication protocols.

In some implementations, a sensor electronics unit can adjust communication protocols based on battery life. For example, and without limitation, the second communication protocol can be used to recover data from a dead and/or low power sensor electronics unit. In some cases, the sensor electronics unit can cease data measurements and/or transmission when the battery life falls below a predetermined threshold. One or more communication protocols (e.g., the second communication protocol) may then be used to power the sensor electronics module and further recover the data stored in the sensor electronics module. In some cases, the sensor electronics unit can load the data onto a passive tag when its battery life falls below a predetermined threshold.

In some cases, a display device can use NFC to power and/or initiate the communication from a sensor electronics unit to the display device via radio transmission (e.g. using a BLUETOOTH® or BLE wireless protocol). Such may be desirable when the sensor electronics unit has low battery life or no battery life. This can be used by a health practitioner to process patient data and/or by any user to pull data off a dying or dead sensor electronics unit, or in cases where there is a malfunction of the sensor electronics unit.

BRIEF DESCRIPTION OF THE DRAWINGS

The disclosed aspects will hereinafter be described in conjunction with the appended drawings, provided to illustrate and not to limit the disclosed aspects, wherein like designations denote like elements. Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

FIG. 6C illustrates an example timing diagram where an RF field communication protocol is used to wake an example sensor electronics unit from a low power mode.

FIG. 6E illustrates an example timing diagram of an example sensor electronics unit that is put into a low power mode.

FIG. 8 illustrates an example flow chart showing how one communication protocol can be used to facilitate pairing for communication using another communication protocol.

DETAILED DESCRIPTION

Figure 1A:
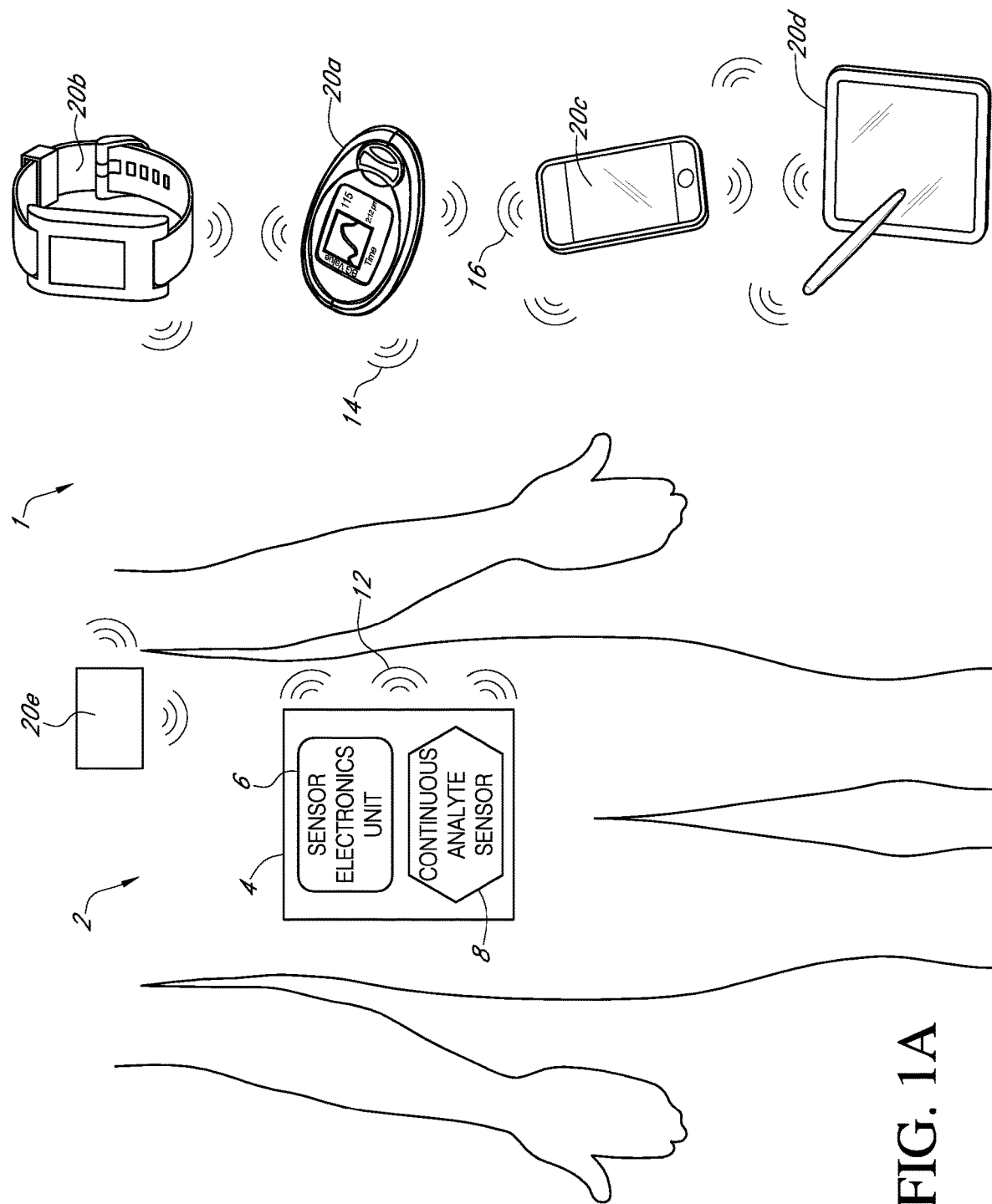
FIG. 1A is a diagram depicting an example continuous analyte monitoring system having a sensor electronics unit, a sensor, and a plurality of display devices that can be connected to the sensor electronics unit.

Various aspects of the novel systems, apparatuses, and methods disclosed herein are described more fully hereinafter with reference to the accompanying drawings. This disclosure can, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the novel systems, apparatuses, and methods disclosed herein, whether implemented independently of, or combined with, any other aspect of the disclosure. For example, an apparatus can be implemented or a method can be practiced using any number of the aspects set forth herein. In addition, the scope of the disclosure is intended to cover such an apparatus or method that is practiced using other structure, functionality, or structure and functionality in addition to or other than the various aspects of the disclosure set forth herein. It should be understood that any aspect disclosed herein can be implemented by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, and/or objectives. The detailed description and drawings are merely illustrative of the disclosure rather than limiting, the scope of the disclosure being defined by the appended claims and equivalents thereof.

As alluded to previously, continuous monitoring of blood glucose values, one example of an analyte (discussed in greater detail below), can improve upon conventional monitoring systems and methods by improving comfort and convenience, as well as lessening the chance that a person's deteriorating or medically critical condition goes unnoticed. Thus, various implementations described herein are directed to systems and methods of continuous analyte monitoring and communications between sensor electronics units and display devices.

In some implementations, a system is provided for continuous measurement of an analyte in a host that can include: a continuous analyte sensor (and/or any other sensor) configured to substantially continuously measure a concentration of the analyte in the host; and a sensor electronics unit operatively and/or communicatively coupled to the continuous analyte sensor to receive the analyte concentration measurements and communicate them to display devices. In particular, the sensor electronics unit can include electronics configured to process data, and/or a data stream, associated at least in part with an analyte concentration measured by the continuous analyte sensor in order to generate sensor information that includes raw sensor data, transformed sensor data, and/or any other sensor data or data derived therefrom, e.g., predictive or trend data. The sensor electronics unit may further be configured to generate sensor information that is customized for respective display devices, such that different display devices may receive sensor information modified for different display devices for presentation to the host, a host care taker, etc.

Communications between the sensor electronics unit and one or more display devices can be controlled via an advertising and communication protocol indicating, for example, how often and/or how long the sensor electronics unit advertises to a display device, the order in which the sensor electronics unit advertised to a display device, etc. The sensor electronics unit may comprise a communications unit operative in accordance with the advertising and communication protocol, such as a radio transceiver, that effectuates such communications between the sensor electronics unit and the one or more display devices. The control effectuated by the advertising and connection protocol can be achieved by varying or adjusting variables or parameters that can impact communications such as, without limitation, the timing and the order of communications.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some implementations, the analyte for measurement by the sensor heads, devices, and methods is analyte. However, other analytes are contemplated as well, including but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-13 hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free 13-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *Rickettsia* (scrub typhus), *Schistosoma mansoni, Toxoplasma gondii, Treponoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Sensor electronics units can include electronics configured to communicate to and store data of sensors (e.g., analyte sensors) of a user. The sensor electronics unit can connect to display devices (e.g., mobile devices, specialized medical receivers), or any of the other display devices described in this disclosure). In any case, display devices can be devices that a user can use to monitor sensor measurements.

In some implementations, the sensor electronics unit may be configured to search for, advertise to, and/or attempt to wirelessly communicate with a display device, such as one from a list of display devices (e.g., a white list). This list can be stored in memory and comprise display device information that reflects, at least in part, those display devices or types of devices that are permitted to pair and/or bond with the sensor electronics unit. For example, and without limitation, in some cases, only display devices or device types (e.g., model, make, or classification of device (e.g., specialized receiver, mobile device, etc.)) on the white list can connect to a sensor electronics unit. A request to connect from a display device not on the white list, or from a display device whose type is not on the white list, may be ignored or rejected, and that display device may not be permitted to connect to the sensor electronics unit.

In this example, a display device on the white list may respond to an advertising signal transmitted by the sensor electronics unit. Upon the sensor electronics unit receiving this response, the white list may be updated with an identifier indicative of the display device. In some implementations, a display device may be removed from the white list after some predetermined time of inactivity, e.g., no communications between the sensor electronics unit and the display device. Another list (e.g., a bonding list) may be utilized to maintain a listing of the bonding or pairing information of display devices that can be paired with the sensor electronics unit. By way of illustration, and without limitation, upon pairing or bonding/inclusion in the white list, the display device identifier may also be stored in the bonding list. Thus, re-pairing a display device to the sensor electronics unit can then be avoided when utilizing a bonding list because the sensor electronics unit can pull the pairing information from the bonding list. For example, and without limitation, if a display device is removed from the white list (e.g., due to some predetermined amount of inactivity, express removal, and/or the pairing of a new device) the identifier of that display device may still be stored in the bonding list. In this way, the bonding list can be accessed upon the sensor electronics unit receiving a response to an advertising signal from a display device to check whether or not the display device was previously bonded to the sensor electronics unit. If so, a data connection can be established without engaging in authentication.

In some implementations, the search for and/or attempted wireless communication can occur in a predetermined and/or programmable order (e.g., grading and/or escalating). For example, and without limitation, if an attempt at communicating with and/or alarming a first display device fails, this failure triggers an attempt to communicate with and/or alarm a second display device, and so on. It should be noted that the sensor electronics unit may not be tied to a single display device. Rather the sensor electronics unit can be configured to communicate with a plurality of different display devices directly, systematically, simultaneously (e.g., via broadcasting), regularly, periodically, randomly, on-demand, in response to a query, based on alerts or alarms, and/or the like.

The sensor information (e.g., data, measurements, etc.) may comprise processed and/or transformed sensor information that does not require processing by the display device prior to display of the sensor information. However, some display devices may comprise software including display instructions (e.g., software programming comprising instructions configured to display the sensor information and optionally query the sensor electronics unit to obtain the sensor information) configured to enable display of the sensor information thereon. In some implementations, the display device is programmed with the display instructions at the manufacturer and can include security and/or authentication to avoid plagiarism of the display device. In some implementations, a display device is configured to display the sensor information via a downloadable program (e.g., a downloadable Java Script via the internet and/or a mobile application downloaded from an entity that created and/or owns and/or licenses the app, and/or an app store such as from APPLE, INC. or GOOGLE INC., or other companies), such that any display device that supports downloading of a program (for example, and without limitation, any display device that supports Java applets or the mobile application) can be configured to display displayable sensor information (e.g., mobile devices, smartphones, tablets, personal digital assistants, personal computers, and the like).

In some implementations, certain display devices may be in direct wireless communication with the sensor electronics unit, although intermediate network hardware, firmware, and/or software can be included within the direct wireless communication. In some implementations, a repeater (e.g., a BLUETOOTH® OR BLE repeater) can be used to re-transmit the transmitted sensor information to a location farther away than the immediate range of the telemetry module of the sensor electronics unit. In some implementations, a display device (e.g., BLUETOOTH® OR BLE display device) can be used to re-transmit the transmitted sensor information to a display device, possibly in a different format, such as in a text message. In certain implementations, the sensor electronics unit transmits sensor information to one or more display devices, where the sensor information transmitted from the sensor electronics unit is received by the display device without intermediate processing of the sensor information.

In some implementations, one or more display devices are configured to query the sensor electronics unit for sensor information, where the display device requests sensor information from the sensor electronics unit in an on-demand fashion, such as, without limitation, in response to a query. In some implementations, the sensor electronics unit can be configured for periodic, systematic, regular, irregular or aperiodic transmission of sensor information to one or more display devices (e.g., every 1, 2, 5, or 10 minutes or more). In some implementations, the sensor electronics unit can be configured to transmit data packages associated with a triggered alert (e.g., triggered by one or more alert conditions). However, any combination of the above-described statuses of data transmission can be implemented with any combination of a paired sensor electronics unit and display device(s). For example, and without limitation, one or more display devices can be configured for querying a sensor electronics unit database and for receiving alarm information triggered by one or more alarm conditions being met. Additionally, the sensor electronics unit can be configured to transmit sensor information to one or more display devices (e.g., the same or different display devices as described in the previous example), where the display devices function differently with regard to how they obtain sensor information.

In some implementations, as described in more detail below, a display device can be configured to query/request data stored in memory in the sensor electronics unit for certain types of data content, including direct queries into a database in the memory of the sensor electronics unit and/or requests for configured or configurable packages of data content therefrom; namely, the data stored in the sensor electronics unit can be configurable, queryable, predetermined, and/or pre-packaged, based on the display device with which the sensor electronics unit is communicating. In some additional or alternative implementations, the sensor electronics unit can generate the sensor information based on the sensor electronic unit's knowledge of which display device is to receive a particular transmission. Additionally, some display devices are capable of obtaining calibration information and wirelessly transmitting the calibration information to the sensor electronics unit, such as through manual entry of the calibration information, automatic delivery of the calibration information, and/or an integral reference analyte monitor incorporated into the display device. U.S. Patent Publication Nos. 2006/0222566, 2007/0203966, 2007/0108245, and 2005/0154271, all of which are incorporated herein by reference in their entirety, describe systems and methods for providing an integral reference analyte monitor incorporated into a display device and/or other calibration methods that can be implemented with implementations disclosed herein.

In general, a plurality of display devices (e.g., a custom analyte monitoring device, a mobile phone, a tablet, a smart watch, a reference analyte monitor, a medicament delivery device, a medical device and a personal computer) may be configured to wirelessly communicate with the sensor electronics unit. The one or more display devices can be configured to display at least some of the sensor information wirelessly communicated by the sensor electronics unit. The sensor information may include, for example and without limitation, sensor data, such as raw data and/or transformed sensor data, such as analyte concentration values, rate of change information, trend information, alert information, sensor diagnostic information, calibration information, temperature readings or non-visual information such as sound, etc.

The features that are described throughout this disclosure have a number of advantages as compared to presently available systems and methods. These will now generally be described. For example, there is a need in the art for improved systems and methods of communication using communication protocols between sensor electronics units and display devices. In some cases, the use of the communication protocol can consume too much power, processor functionality, and/or other resources of a CGM system. This issue can be compounded through repetitive pairing, synchronizing, and/or handshaking procedures that may be used in some communication protocols, such as BLUETOOTH® OR BLE. Accordingly, there is a need for improved communications that effectively utilize power, processor functionality, and/or other resources of CGM systems.

In some cases, the repetitive pairing, synchronizing, and/or handshaking procedures of CGM systems can also cause excessive communication traffic. This communication traffic can burden networks and/or drain network resources (e.g., communication channels, data lines, power, processing power, etc.), such as by tying up communication channels and/or data lines, causing interference, consuming power, utilizing processor time, etc. In some cases, excessive communication traffic can lead to network slowdown, network failure, and/or increased costs in running networks, such as more energy costs or additional hardware utilization (e.g., processors, communication lines, cooling, etc.). Accordingly, there is a need for improved communications in CGM systems.

In particular, because certain CGM systems perform repetitive handshaking/authentication to exchange data (e.g., EGV data) with some protocols (e.g., radio transmission such as BLUETOOTH®), these CGM systems can strain the battery life of sensor electronics unit. In addition, because multiple display devices can compete to connect with the sensor electronics unit (e.g., during the same advertisement window), repetitive handshaking/authentication may lead to unwanted interference. This interference may lead to connection failure, and eventually to unwanted data drop. Accordingly, utilizing a second communication protocol (e.g., an RF field such as NFC or RFID) can allow CGM systems to more efficiently pair sensor electronics units to display devices on demand.

In some cases, interactions using communication protocols between sensor electronics units and display devices can be non-intuitive and/or cumbersome for users. For example, and without limitation, a user may navigate through multiple menus and configure multiple devices in order to pair and/or un-pair sensor electronics units, display devices, and/or other devices that utilize a communication protocol. As another non-limiting example, initialization protocols, where sensor electronics units and/or display devices are calibrated and/or configured, can require navigation of multiple menus that can be cumbersome for a user. Having too many steps can detract from the user experience and/or deter users from effectively using CGM systems and/or faithfully following their medical regimen. Accordingly, there is a need for improved communications in CGM systems that allow for enhanced usability.

In some cases, user authentication of a display device for a transceiver can be slow and/or cumbersome for users. However, such authentication may provide security for users by preventing unauthorized devices from receiving and/or sending data and/or commands to sensor electronics units. Having too many steps of an authentication scheme can detract from the user experience and/or also further discourage users from effectively using the system and/or faithfully following their medical regimen. Accordingly, there is a need to improve user authentication between display devices and sensor electronics units.

In some cases, communications over a communication protocol can be compromised and/or otherwise lead to security problems. For example, and without limitation, a device can steal a display devices' authentication and/or communicate as a display device to a sensor electronics unit. Such security issues can allow an unauthorized person to receive private information and/or take control of a user's CGM system, possibly causing harm. Accordingly, there is a need for advanced communication systems and/or methods to improve security.

In some cases, some communication protocols, such as BLUETOOTH® OR BLE, use energy from the sensor electronics unit to send messages. As a result, it can be difficult to get data from a sensor electronics unit once the sensor electronics unit has run out of power (e.g., the sensor electronics unit's battery has died) or there has been a malfunction/fault in the sensor electronics unit that may prevent transfer of data over radio transmission such as BLUETOOTH® OR BLE (e.g., an error in the radio protocol). Retrieving such data can be desirable when a user has not previously accessed the data from the sensor electronics (e.g. data was note transmitted to the user's display device) and/or desires an additional copy. A health practitioner may also desire to download this data as well in order to provide the appropriate treatment to a patient. Accordingly, there is a need for systems and methods to extract data from sensor electronics units when the sensor electronics units no longer have energy to power some communication protocols or there has been a malfunction.

In some cases, communications can be at predefined time intervals. For example, a sensor electronics unit may only be able to communicate to a display device every 5 minutes, 10 minutes, 15 minutes, 20 minutes, or any other predefined period of time. As another example, a sensor electronics unit may only clear devices off white lists to permit a new device to connect every 5 minutes, 10 minutes, 15 minutes, 20 minutes, or any other predefined period of time. A user may desire to have a display device pair with a sensor electronics unit, or send/receive communications from the display device to the sensor electronics unit outside of the predefined period of time. Accordingly, there is a need for systems and methods to enable communications users to pair and/or communicate on-demand. These and more advantages will be readily apparent by the implementations disclosed herein.

FIG. 1A is a diagram depicting an example Continuous Analyte Monitoring System 1 having Sensor Electronics Unit 6, Continuous Analyte Sensor 8, and a plurality of Display Devices 20A-E that can be connected to Sensor Electronics Unit 6. Continuous Analyte Monitoring System 1 can include Analyte Sensor System 4 and Display Devices 20A-E. Analyte Sensor System 4 can be operatively connected to Host 2 and a plurality of Display Devices 20A-E according to certain aspects of the present disclosure. In some cases, Display Devices 20A-E can run a software application, such as a mobile application (e.g., a mobile application downloaded from an entity that created and/or owns and/or licenses the app, and/or an app store such as from APPLE, INC. or GOOGLE INC., or other), also referred to as an app, that performs the functionality and/or has the structure described throughout this disclosure.

Display device 20E alternatively or in addition to being a display device, may be a medicament delivery device that can act cooperatively with Analyte Sensor System 4 to deliver medicaments to Host 2. By way of illustration, and without limitation, Display Device 20E can be an insulin delivery pump, an insulin delivery pen, or other devices for delivery medication. Analyte Sensor System 4 can include Sensor Electronics Unit 6 and Continuous Analyte Sensor 8, which can be associated with Sensor Electronics Unit 6. Sensor Electronics Unit 6 may be in direct wireless communication with one or more of the plurality of Display Devices 20A-E via wireless communications signals or wired communication signals. As will be discussed in greater detail below, Display Devices 20A-E may also communicate amongst each other and/or through each other to Analyte Sensor System 4. Wireless communications signals from Analyte Sensor System 4 to Display Devices 20A-E can include uplink Signals 12. Wireless communications signals from Display Devices 20A-E to Analyte Sensor System 4 can be include downlink Signals 14. Wireless communication signals can also be between two or more of Display Devices 20A-E. By way of illustration, crosslink Signal 16 can be signal communications between Display Device 20A and Display Device 20C.

Sensor Electronics Unit 6 can include sensor electronics that are configured to process sensor information and/or send and/or receive sensor data to one or more Display Devices 20A-E. FIG. 1A illustrates Display Devices 20A-E, but as will be discussed in this disclosure with reference to FIG. 2A, Continuous Analyte Monitoring System 1 can have any number of Display Devices 20A-N. Display Device 20, as used throughout this disclosure, represents any one of Display Devices 20A-N. In certain implementations, Sensor Electronics Unit 6 can include electronic circuitry associated with measuring and processing data from Continuous Analyte Sensor 8, including prospective algorithms associated with processing and/or calibration of the continuous analyte sensor data. Sensor Electronics Unit 6 can be integral with (e.g., non-releasably attached to) or releasably attachable to the Continuous Analyte Sensor 8 achieving a physical connection therebetween. Sensor Electronics Unit 6 may include hardware, firmware, and/or software that enable analyte level measurement. For example, and without limitation, Sensor Electronics Unit 6 can include a potentiostat, a power source for providing power to Continuous Analyte Sensor 8, other components useful for signal processing and data storage, and a telemetry module for transmitting data from itself to one or more Display Devices 20A-N. Electronics can be affixed to a printed circuit board ("PCB"), or the like, and can take a variety of forms. For example, the electronics can take the form of an integrated circuit ("IC"), such as an Application-Specific Integrated Circuit ("ASIC"), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0108245, all of which are incorporated herein by reference in their entirety for all purposes.

Display Devices 20A-N can be configured for displaying, alarming, and/or basing medicament delivery on the sensor information that has been transmitted by Sensor Electronics Unit 6 (e.g., in a data package that is transmitted to one or more of Display Devices 20A-N based on their respective preferences). Each of Display Devices 20A-N can include a display such as a touchscreen display for displaying sensor information to a user (e.g., Host 2 or a care taker/medical professional) and/or receiving inputs from the user. In some implementations, Display Devices 20A-N may include other types of user interfaces such as a voice user interface instead of or in addition to a touchscreen display for communicating sensor information to the user of Display Devices 20A-N and/or receiving user inputs. In some implementations, one, some, or all of Display Devices 20A-N can be configured to display or otherwise communicate the sensor information as it is communicated from Sensor Electronics Unit 6 (e.g., in a data package that is transmitted to respective Display Devices 20A-N), without any additional prospective processing required for calibration and real-time display of the sensor information.

In some implementations, Display Device 20A can be a specialized medical receiver, specially designed for displaying certain types of displayable sensor information associated with analyte values received from Sensor Electronics Unit 6 (e.g., a numerical value and a direction such as trending upward or downward). In some implementations, Display Device 20C can be a handheld device, such as a mobile phone based on the Android or iOS operating system, a palm-top computer and the like, where Display Device 20C can have a relatively larger display and be configured to display a graphical representation of the continuous sensor data (e.g., including current and/or historic data). Other display devices can include other hand-held devices, such as a tablet (e.g., Display Device 20D), a smart watch (e.g., Display 20B), a medicament delivery device (e.g., Display Device 20E), a blood glucose meter, and/or a desktop or laptop computers.

As alluded to above, because the different Display Devices 20A-N can provide different user interfaces, content of the data packages (e.g., amount, format, and/or type of data to be displayed, alarms, and the like) can be customized (e.g., programmed differently by the manufacturer and/or by a user) for each particular display device and/or display device type. Accordingly, in some implementations, one or more of Display Devices 20A-N can be in direct or indirect wireless communication with Sensor Electronics Unit 6 to enable a plurality of different types and/or levels of display and/or functionality associated with the sensor information, which is described in more detail elsewhere herein.

Continuous Analyte Sensor 8 can be, for example and without limitation, a subcutaneous, transdermal (e.g., transcutaneous), or intravascular device. In some implementations, Continuous Analyte Sensor 8 can analyze a plurality of intermittent blood samples, although Continuous Analyte Sensor 8 can be configured to use any method of analyte-measurement, including enzymatic, chemical, physical, electrochemical, spectrophotometric, polarimetric, calorimetric, iontophoretic, radiometric, immunochemical, and the like.

Continuous Analyte Sensor 8 can use any known method, including invasive, minimally invasive, and non-invasive sensing techniques (e.g., fluorescent monitoring), to provide a data stream indicative of the concentration of a measured analyte in Host 2. In some implementations, this data stream can be typically a raw data signal, which can be converted into a calibrated and/or filtered data stream that is used to provide a useful value of the measured analyte to a user, such as Host 2 or a caretaker (e.g., a parent, a relative, a guardian, a teacher, a doctor, a nurse, and/or any other individual that has an interest in the well-being of Host 2). It should be understood that the devices and methods described herein can be applied to any device capable of detecting a concentration of an analyte and providing an output signal that represents the concentration of the analyte.

In some implementations, Continuous Analyte Sensor 8 can be capable of measuring a concentration of glucose in Host 2, one of which is described below as utilizing an implantable continuous glucose sensor. For example, and without limitation, Continuous Analyte Sensor 8 can be an implantable glucose sensor, such as described with reference to U.S. Pat. No. 6,001,067 and U.S. Patent Publication No. US-2005-0027463-A1. In another implementation, Continuous Analyte Sensor 8 can be a transcutaneous glucose sensor, such as described with reference to U.S. Patent Publication No. US-2006-0020187-A1. In still other implementations, Continuous Analyte Sensor 8 can be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, co-pending U.S. Patent Publication No. US-2008-0108942-A1 filed on Mar. 26, 2007, and co-pending U.S. Patent Application No. US-2007-0197890-A1 filed on Feb. 14, 2007. In one alternative implementation, Continuous Analyte Sensor 8 can comprise a transcutaneous sensor such as described in U.S. Pat. No. 6,565,509 to Say et al., for example. In another alternative implementation, Continuous Analyte Sensor 8 can comprise a subcutaneous sensor such as described with reference to U.S. Pat. No. 6,579,690 to Bonnecaze et al. or U.S. Pat. No. 6,484,046 to Say et al., for example. In another alternative implementation, Continuous Analyte Sensor 8 can comprise a refillable subcutaneous sensor such as described with reference to U.S. Pat. No. 6,512,939 to Colvin et al., for example. In another alternative implementation, Continuous Analyte Sensor 8 an comprise an intravascular sensor such as described with reference to U.S. Pat. No. 6,477,395 to Schulman et al., for example. In another alternative implementation, Continuous Analyte Sensor 8 can comprise an intravascular sensor such as described with reference to U.S. Pat. No. 6,424,847 to Mastrototaro et al., for example. Each of the aforementioned patents and patent applications are herein incorporated by reference.

Figure 1B:
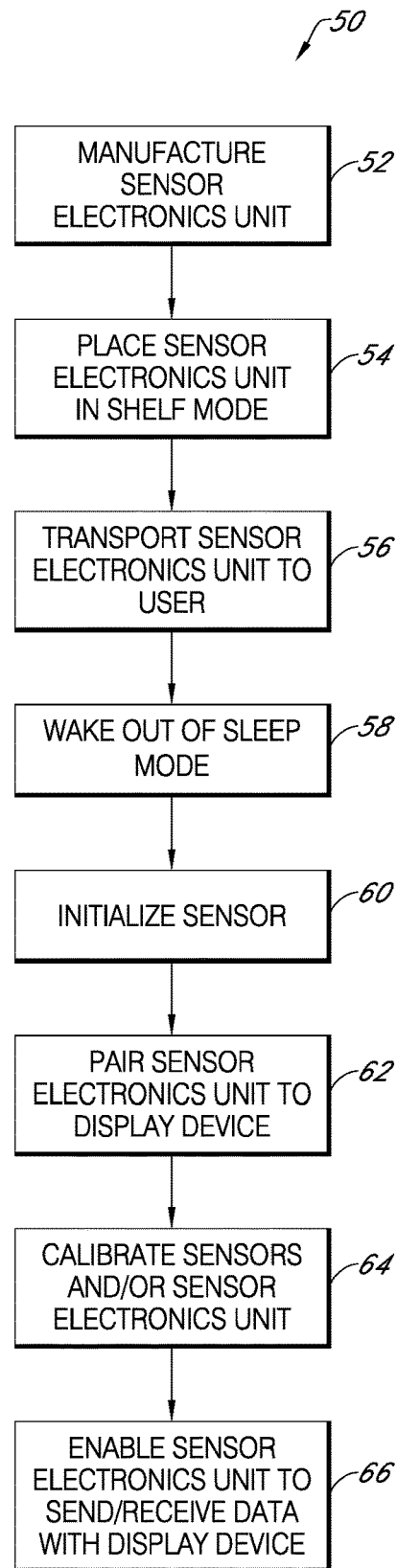
FIG. 1B illustrates an example flow chart showing an example initiation of a sensor electronics unit from manufacturing to use by a user.

FIG. 1B illustrates an example flow chart showing an example initiation of Sensor Electronics Unit 6 from manufacturing to use by a user. Sensor Electronics Unit 6 can have a predetermined life cycle comprising the example method 50. In Block 52, Sensor Electronics Unit 6 can be manufactured in a factory setting. In some cases, the manufacturing can involve circuit fabrication, assembly, testing, calibration, etc. In Block 54, once Sensor Electronics Unit 6 is manufactured, it can then be put in a shelf mode and/or any low power mode, which will be described more with reference to FIG. 6E, as well as elsewhere throughout this disclosure. This shelf mode and/or any low power mode can enable Sensor Electronics Unit 6 to consume less power before it is used. In Block 56, as the Sensor Electronics Unit 6 is in shelf mode, it can be transported to a user. As a non-limiting illustrative example, a Sensor Electronics Unit 6 can be in shelf mode as it is shipped, placed into storage, and/or before it is activated by a user. There are other instances where a Sensor Electronics Unit 6 may be put into shelf mode and/or any low power mode, which will be described throughout this disclosure.

In Block 58, when it is desirable for the Sensor Electronics Unit 6 to be activated and used, the Sensor Electronics Unit 6 can be woken out of shelf mode and/or any low power mode. For example and without limitation, in some cases, the Sensor Electronics Unit 6 can periodically check to see if it is connected to a Continuous Analyte Sensor 8. This periodic check can involve sensing the current and/or voltage across electrodes. In some cases, as an illustrative example and without limitation, the periodic check can occur at a predetermined time intervals and/or after a predetermined number of counts, such as every 5, 10, 15, or any desirable number of minutes. If there is a change in current and/or voltage indicative at least in part of a connection to a Continuous Analyte Sensor 8 (e.g., an increase in current and/or voltage, and/or a change over a certain period of time and/or counts) the Sensor Electronics Unit 6 can wake up. In certain cases, a predetermined threshold can be used for the current, voltage, number of counts, time, etc. such that when the currents, voltages, numbers of counts, time, etc. exceed (or fall below when appropriate) that predetermined threshold, the Sensor Electronics Unit 6 wakes up. In some implementations, if the Sensor Electronics Unit 6 has an accelerometer, waking up can occur much faster. For example, and without limitation, while in shelf mode, the Sensor Electronics Unit 6 can perform a current check once every five (5) minutes or at longer intervals. If the accelerometer detects motion, the Sensor Electronics Unit 6 can wake up and reduce the intervals at which it checks for current. The Sensor Electronics Unit 6 can go back into shelf mode if the current remains under the wake-up threshold and no motions are detected for a certain period of time. Advantageously, the accelerometer can facilitate much shorter warm-up times without shelf life being impacted. The motion can be indicative of a user getting ready to use the Sensor Electronics Unit 6.

In Block 60, after the Sensor Electronics Unit 6 wakes up, the Continuous Analyte Sensor 8 of the Sensor Electronics Unit 6 can begin initialization. The initialization can be part of a warm up period where the Sensor Electronics Unit 6 and/or Continuous Analyte Sensor 8 run software, calibrates, runs diagnostics, etc.

In Block 62, the Sensor Electronics Unit 6 can pair with one or more Display Devices 20A-N. In order to pair with display devices, the Sensor Electronics Unit 6 can first advertise (e.g., broadcasting to display devices for connection) to pair with display devices. Advertising by the Sensor Electronics Unit 6 can include using a communication protocol, such as, without limitation, BLUETOOTH® (e.g., BLUETOOTH® Low Energy ("BLE"), classic BLUETOOTH®, Dual-mode BLUETOOTH®, etc.), IBEACONS®, ZIGBEE®, Wi-Fi, induction wireless data transmission, radio transmission, radio-frequency identification ("RFID"), near-field communication ("NFC"), and/or any other communication protocol desired and/or mentioned in this disclosure. As used herein, any reference to BLUETOOTH® can include BLE, classic BLUETOOTH®, Dual-mode BLUETOOTH®, and/or any other BLUETOOTH® protocol. Any Display Devices 20A-N receiving the advertisement can send a connection request to the sensor electronics device 6. The Sensor Electronics Unit 6 and the Display Devices 20A-N can then proceed with the appropriate steps to pair using the communication protocol used (e.g., authentication, connection, encryption/decryption, exchanging data, etc.).

In Block 64, once one or more Display Devices 20A-N and a Sensor Electronics Unit 6 are paired, a user can calibrate the Continuous Analyte Sensor 8 and/or Sensor Electronics Unit 6. In some cases, the user can use finger sticking to take measurements indicative of his/her blood glucose levels. He/she can enter those measurements into one or more Display Devices 20A-N, which can transmit the data using a communication protocol to the Sensor Electronics Unit 6, where the measurements can be used to calibrate the Continuous Analyte Sensor 8. For example, and without limitation, the measurements can be incorporated into a calibration function which can be used by a Continuous Analyte Sensor 8 and/or Sensor Electronics Unit 6 to convert measurements taken by Continuous Analyte Sensor 8 or (e.g., current and/or voltage measurements) into measurements indicative of blood glucose levels, such as, without limitation, measurements with units mmol/L or mg/dL. In some cases, the calibration function can be used in one or more Display Devices 20A-N and not in the Continuous Analyte Sensor 8 and/or Sensor Electronics Unit 6. In such a case, raw data (e.g., voltages, currents, counts) can be sent to Display Devices 20A-N, where it can be converted to measurements indicative of blood glucose levels. After calibration, the Sensor Electronics Unit 6 can go into a transmission cycle, where it can communicate with connected Display Devices 20A-N and/or any other desired devices.

In Block 66, the Sensor Electronics Unit 6 can connect to the one or more Display Devices 20A-N and transmit/receive communications in a transmission cycle, where Sensor Electronics Unit 6 sends relevant data (e.g., analyte data) to the one or more Display Devices 20A-N. As an example illustration, and without limitation, the Sensor Electronics Unit 6 and the Display Devices 20A-N can be connected during the transmission cycle using the following procedures. The Sensor Electronics Unit 6 can periodically advertise at predetermined time intervals, such as every 5, 10, 15, and/or any number of minutes as desired. The advertisement window can be anywhere from 7 seconds to 22 seconds. In some cases, the duration of the advertisement window can be open longer to allow for a plurality of Displays Devices 20A-N (e.g., a receiver and/or mobile devices) to connect and/or exchange data and/or commands/requests. The duration of any given interval can be dependent on the type of each of Display Devices 20A-N present.

This transmission cycle can be influenced by the battery constraints of the Sensor Electronics Unit 6. Modifying advertising parameters such as advertising interval or duration can directly impact the total battery life of the Sensor Electronics Unit 6. Through testing, these parameters (e.g., advertisement intervals and durations) can be tuned to optimize the time it takes for the different Display Devices 20A-N to connect. In some cases, these parameters can be smartly tuned in order to adaptively change in operation by monitoring past connection performance in order to set, for example, the advertisement intervals and duration. By doing so, having the Displays Devices 20A-N connect as fast as possible can reduce the total average time of advertising when a Display Device 20A-N is nearby.

As mentioned, in some cases Continuous Analyte Monitoring System 1 can comprise a Sensor Electronics Unit 6 operatively and/or communicatively coupled to a Continuous Analyte Sensor 8. The Sensor Electronics Unit 6 can receive data (raw and/or processed) from Continuous Analyte Sensor 8. Also as mentioned, the Sensor Electronics Unit 6 can communicate to one or more Display Devices 20A-N using a communication protocol, such as, without limitation, a radio transmission including BLUETOOTH®. Through this communication protocol, the Sensor Electronics Unit 6 can send data to the one or more Display Devices 20A-N, including, without limitation, data based at least in part on the received sensor information. The one or more Display Devices 20A-N can also send data, commands, and/or other communication to the Sensor Electronics Unit 6.

In some cases, where the Sensor Electronics Unit 6 and one or more Display Devices 20A-N connect using radio transmission such as BLUETOOTH®, the Sensor Electronics Unit 6 can play the role of a peripheral device, which is an auxiliary device that is configured to connect, and in some cases support, the central devices which the user uses. In this situation, the Display Devices 20A-N can play the roles of central devices. In this setup, the central devices can be responsible for scanning for a peripheral device to connect to. By way of illustration, using this terminology (which is sometimes used in the art) for abundance of clarity, a peripheral device (e.g., the Sensor Electronics Unit 6) can advertise that it is available for a connection and accept connection requests made by central devices (e.g., Display Devices 20A-N). In some implementations, the peripheral device may not serve more than a predetermined number of connections in one transmission window (e.g. 1, 2, 3, 4, 5, 6, or more connections). To allow for the peripheral device to request data periodically, such as every 5, 10, 15 and/or any number of desired minutes, the central devices can scan, connect, exchange data, and ultimately disconnect in a timely manner. The peripheral device can enforce timeouts within the connection to prevent central devices from staying connected longer than expected. The peripheral device can use a white list, as previously described, to permit specific central devices, or types of devices, to connect. This can mean that even though it is advertising itself as connectable, a central device may be rejected from connecting due to the white list feature being enabled for different central devices.

Figure 1C:
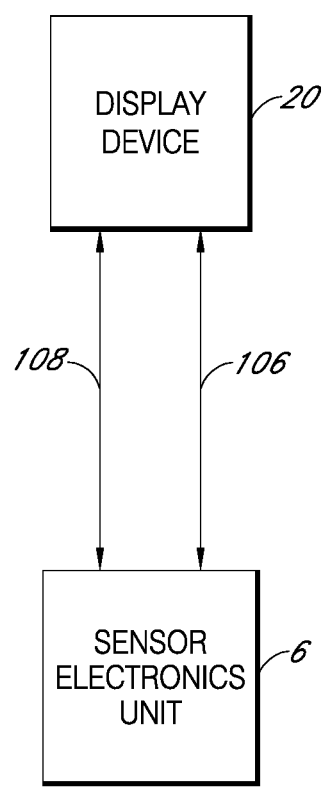
FIG. 1C illustrates an example display device and sensor electronics unit communicating with two different communication channels.

In some implementations, a Sensor Electronics Unit 6 can communicate with one or more Display Devices 20A-N using a plurality of communication channels. FIG. 1C illustrates Sensor Electronics Unit 6 communicating over two different Communication Channels 106, 108 with Display Device 20. As previously mentioned, Display Device 20, as used throughout this disclosure, represents any one of Display Devices 20A-N.

Sensor Electronics Unit 6 and Display Device 20 can communicate over a plurality of communication protocols over Communication Channels 106, 108. As used herein, communication protocols can include any communication system configured to transmit information between two or more electronics, including, without limitation, wired and wireless technologies such as BLUETOOTH®, IBEACONS®, ZIGBEE®, Wi-Fi, induction wireless data transmission, radio frequencies, RFID, NFC, GSM, infrared, Ethernet cables, coaxial cables, Universal Serial Bus ("USB"), firewire, data lines, wire, and/or any wired and/or wireless connection known in the art. In some cases, communication protocols can utilize radio transmission, such as that used by BLUETOOTH®. Radio transmission is described further throughout this disclosure, including with reference to FIGS. 5A-B. In some cases, communication protocols can utilize electromagnetic radio waves (e.g., the electro induction between antenna loops) and/or radio frequency ("RF") fields, such as those used by NFC or RFID. Radio transmission and RF fields are described further throughout this disclosure, including with reference to FIGS.

5A-B. And where particular communication protocols are discussed in reference to examples, it should be understood that other communication protocols could be used as well.

As an illustrative example, Communication Channel 106 can utilize RF fields, such as, without limitation, NFC or RFID. Communication Channel 108 can utilize radio transmission, such BLUETOOTH®. In the case where Communication Channel 106 is NFC or and Communication Channel 108 is BLUETOOTH®, NFC or RFID can provide some advantages over BLUETOOTH®, including, without limitation, having little interference in crowds, ease of use, automatic pairing when in proximity, lower power usage, and others. Similarly, BLUETOOTH® can have advantages over NFC or RFID such as high speed of data transmission, increased range, autonomous communications with multiple different devices, automatically scheduled transmissions and others.

In some implementations, as will be described in this disclosure, data, commands, statuses, and/or other communications between Sensor Electronics Unit 6 and Display Device 20 can be transmitted over different communication protocols, such as Communication Channels 106, 108, depending on context, such as the range of the communication protocol or the speed of data transfer. In some cases, communication over multiple communication protocols, together and/or sequentially, can be used to provide additional security, usability, and/or other desirable advantages. Each of the multiple communication protocols used can have different characteristics that can be utilized differently, and for different advantages in different uses.

Figure 2A:
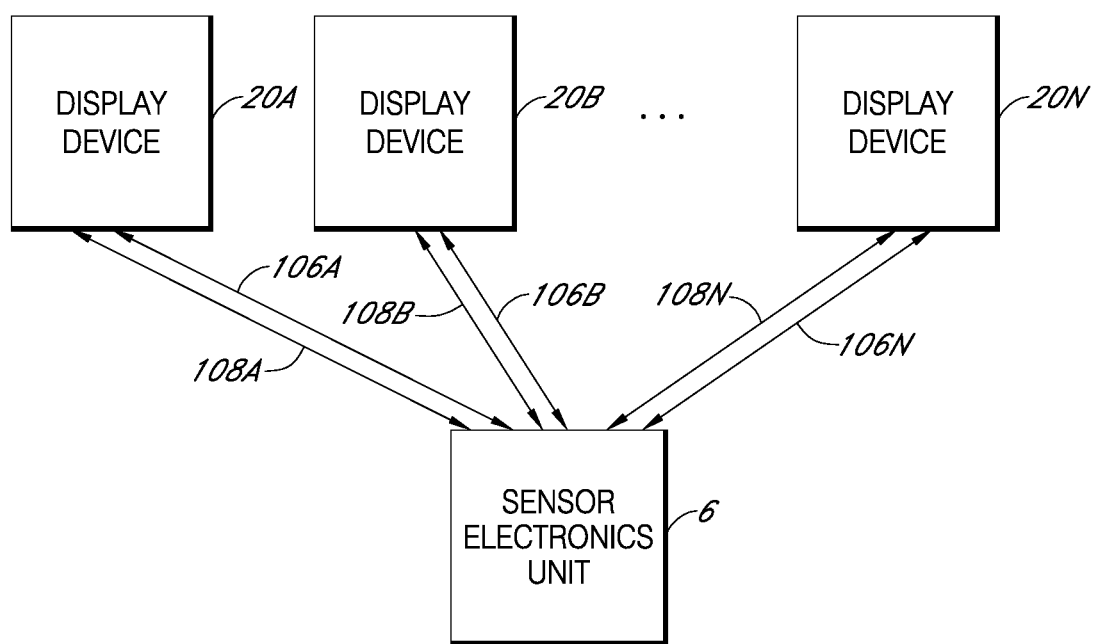
FIG. 2A illustrates a block diagram of an example system where a sensor electronics unit is communicatively coupled to a plurality of display devices using a plurality of communication channels.

FIG. 2A illustrates a block diagram of an example system where a Sensor Electronics Unit 6 is communicatively coupled to a plurality of Display Devices 20A-N using a plurality of Communication Channels 106A-N, 108A-N. As used herein, "N" in Display Devices 20A-N and Communication Channels 106A-N, 108A-N can be indicative at least in part of the number of display devices that can connect to Sensor Electronics Unit 6 at once. For example, where N is B, B can be indicative at least in part that two display devices (e.g., Display Devices 20A, B) can connect to Sensor Electronics Unit 6 and can communicate with Sensor Electronics Unit 6 over Communication Channels 106A-B, 108A-B. Where N is C, C can be indicative that at least in part that three display devices (e.g., Display Device 20A,B,C) can communication over Communication Channels 106A-C, 108A-C. Similarly, N can be indicative at least in part of any number of display devices. In some cases, this number of display devices that can connect to Sensor Electronics Unit 6 can be predetermined in the manufacturing and/or configuration of Sensor Electronics Unit 6. For example, two (2) or three (3) display devices can connect to Sensor Electronics Unit 6 in many example configurations, however, this number is not limited, and more can connect. In some cases, the number of display devices that can connect to Sensor Electronics Unit 6 can be limited by the communication protocol and/or the energy consumption of the communication protocol. For example, and without limitation, some versions of BLUETOOTH® may be limited to up to seven (7) display devices.

In some cases, one or more of Communication Channels 106A-N can utilize the same communication protocols as each other. In some cases, one or more of Communication Channels 106A-N can utilize the different communication protocols from each other. Similarly, in some cases, one or more of Communication Channels 108A-N can utilize the same communication protocols as each other, or one or more of Communication Channels 108A-N can utilize different communication protocols from each other. Also, in some cases, any of Communication Channels 106A-N can utilize the same communication protocols as any of Communication Channels 108A-N. Similarly, in some cases, any of Communication Channels 106A-N can utilize different communication protocols as any of Communication Channels 108A-N. That is, it is appreciated that any kind of permutation of different communication protocols can be used as the Communication Channels 106A-N, 108A-N between Sensor Electronics Unit 6 and Display Devices 20A-N. As a non-limiting example, Communication Channels 106A-N each can use a first communication protocol, such as a radio transmission like BLUETOOTH®, and Communication Channels 108A-N can each use a second, different communication protocol, such as an RF field like NFC or RFID. Communication between each of Display Devices 20A-N can also use any of the communication protocols described in this disclosure, including radio transmission (e.g., BLUETOOTH®) or RF fields (e.g., NFC or RFID).

Figure 2B:
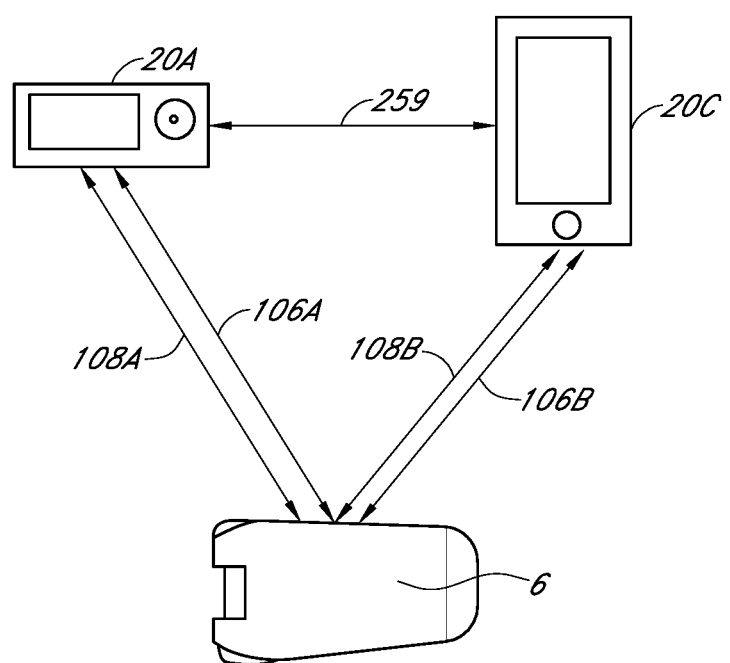
FIG. 2B illustrates an example system where an example sensor electronics unit is communicatively coupled to two example display devices.

FIG. 2B illustrates an example system where an example Sensor Electronics Unit 6 is communicatively coupled to two example Display Devices 20A, C, and Display Device 20A and Display Device 20C are configured to communication with each other. Display Devices 20A,C are particularly illustrative because in many implementations, especially for CGM systems, a user may have Display Device 20A as a specialized display device and one other Display Device 20C, which can be a mobile device. However, Display Devices 20A,C are illustrated merely as examples, and any other display device, including any of Display Devices 20A-N, can instead be used. Display Devices 20A,C can communicate with each other through Communication Channel 259. Over Communication Channel 259, Display Devices 20A,C can utilize any communication protocol described in this disclosure. By way of illustrative example, and without limitation, Display Devices 20A,C can communicate with each other using an RF field such as NFC or RFID. For example, using NFC or RFID, Display Devices 20A,C can transmit data (e.g., estimated blood glucose levels, pairing information, information about a Sensor Electronics Unit 6, calibration information, timing information (e.g., time synchronizations, EGV data with time stamps, etc.), raw sensor data, system status information, detected faults, alerts, clocking information, device manufacturing ID, and/or any other data and/or information described in this disclosure), commands/requests (e.g., data requests, synchronization requests, pairing requests), etc. to one another. In some cases, information about Sensor Electronics Unit 6 can be transmitted to allow one of Display Devices 20A,C to facilitate pairing of the other of Display Devices 20A,C to Sensor Electronics Unit 6. This information can be used to allow the other of Display Devices 20A,C to pair with Sensor Electronics Unit 6 using another communication protocol, such as a communication utilizing radio transmission, including BLUETOOTH®. For example, and without limitation, pairing information can be sent directly between Display Devices 20A, C or via a server (e.g., a network, cloud, etc.). By way of illustration, and without limitation, a user can pair Display Device 20A with Sensor Electronics Unit 6. Subsequently, the pairing information (e.g., timing information, encryption key, authentication information, advertising parameters, address, make/model, name, GAP, IRK, and/or any other relevant information for pairing) of Sensor Electronics Unit 6 can be sent to Display Device 20C from Display Device 20A directly, or Display Device 20A can send that pairing information to a server, which Display Device 20C can then access. Accordingly, Display Device 20C can download the pairing information uploaded by Display Device 20A. With the pairing information, Display Device 20C can then more easily pair with Sensor Electronics Unit 6. In some cases, Display Device 20C can download the pairing information by signing into a mobile application (e.g., a mobile application downloaded from an entity that created and/or owns and/or licenses the app, and/or an app store such as from APPLE, INC. or GOOGLE INC., or other companies). After sign in, this mobile application can communicate with the server and obtain the pairing information so Display Device 20C can connect with the Sensor Electronics Unit 6. Advantageously, allowing Display Devices 20A,C to communicate in this way can allow pairing information to be shared quickly and efficiently, which can reduce communication traffic between Display Device 20A and/or Display Device 20C and Sensor Electronics Unit 6. Moreover, it can allow Display Devices 20A,C to update and/or receive information (e.g., via the server) when Display Devices 20A,C are not within range of each other and/or Sensor Electronics Unit 6. Having this ability to update and/or receive information can be advantageous in keeping a plurality of Display Devices 20A,C updated even when they are not connected to Sensor Electronics Unit 6. Such transfer of pairing information between Display Devices 20A,C can be advantageous in allowing a healthcare practitioner to set up a system for a user. For example, and without limitation, the healthcare practitioner could have Display Device 20C that can send over the pairing information of a patient's Display Device 20A during setup of Display Device 20A. This can allow the healthcare practitioner to facilitate the patient's use of Display Device 20A, especially when the patient is a child, elderly person, handicapped, or otherwise not fully capable of setting up Display Device 20A. As another non-limiting example, a user may want to use Display Device 20C and uses Display Device 20A to send over the pairing information.

Estimated blood glucose levels can be sent between Display Devices 20A,C to facilitate viewing of information regarding the user of Sensor Electronics Unit 6. For example, and without limitation, Display Device 20A can be a display device of a user. Display Device 20C can be a display device belonging to a medical practitioner. Transmission, using an RF field, such as NFC or RFID, of data from Display Device 20A to Display Device 20C can comprise past data that can allow the health practitioner to analyze the behavior of the patient's blood glucose level and provide therapy. Advantageously, NFC or RFID can allow a secure way of transferring such data without the need for pairing. Also, since the doctor may ultimately retrieve data from a plurality of display devices, or have a plurality of display devices to which he/she can connect using a radio transmission such as BLUETOOTH®, the ability to use NFC or RFID can allow the doctors to save battery in his/her display device (e.g., from not advertising and/or having to re-authenticate) and may allow the practitioner to not mistakenly connect to another device in the vicinity. In other uses, the data sent via NFC or RFID can be used for backfill purposes in order to allow one of Display Devices 20A-B to send past data to the other. In some cases, present data can also be sent via NFC or RFID between Display Devices 20A-B. A person having ordinary skill in the art should appreciate that other communication protocols can be used as well to transfer data, such as Wi-Fi or any other communication protocol described in this disclosure.

In some implementations, a communication protocol (e.g., NFC, RFID, Wi-Fi, BLUETOOTH® and/or any other communication protocol described in this disclosure or known in the art) can be used to synchronize alerts on Display Devices 20A,C. For example, and without limitation, Wi-Fi can be used so that when a user acknowledges an alert or communication on one of Display Devices 20A,C, such acknowledgment is viewable on the other of Display Devices 20A,C. Advantageously, this can allow a plurality of users and devices to coordinate regarding therapy of a user of a Sensor Electronics Unit 6, and/or prevent excessive alerts and communications for multiple users and/or a single user using multiple devices.

Figure 3:
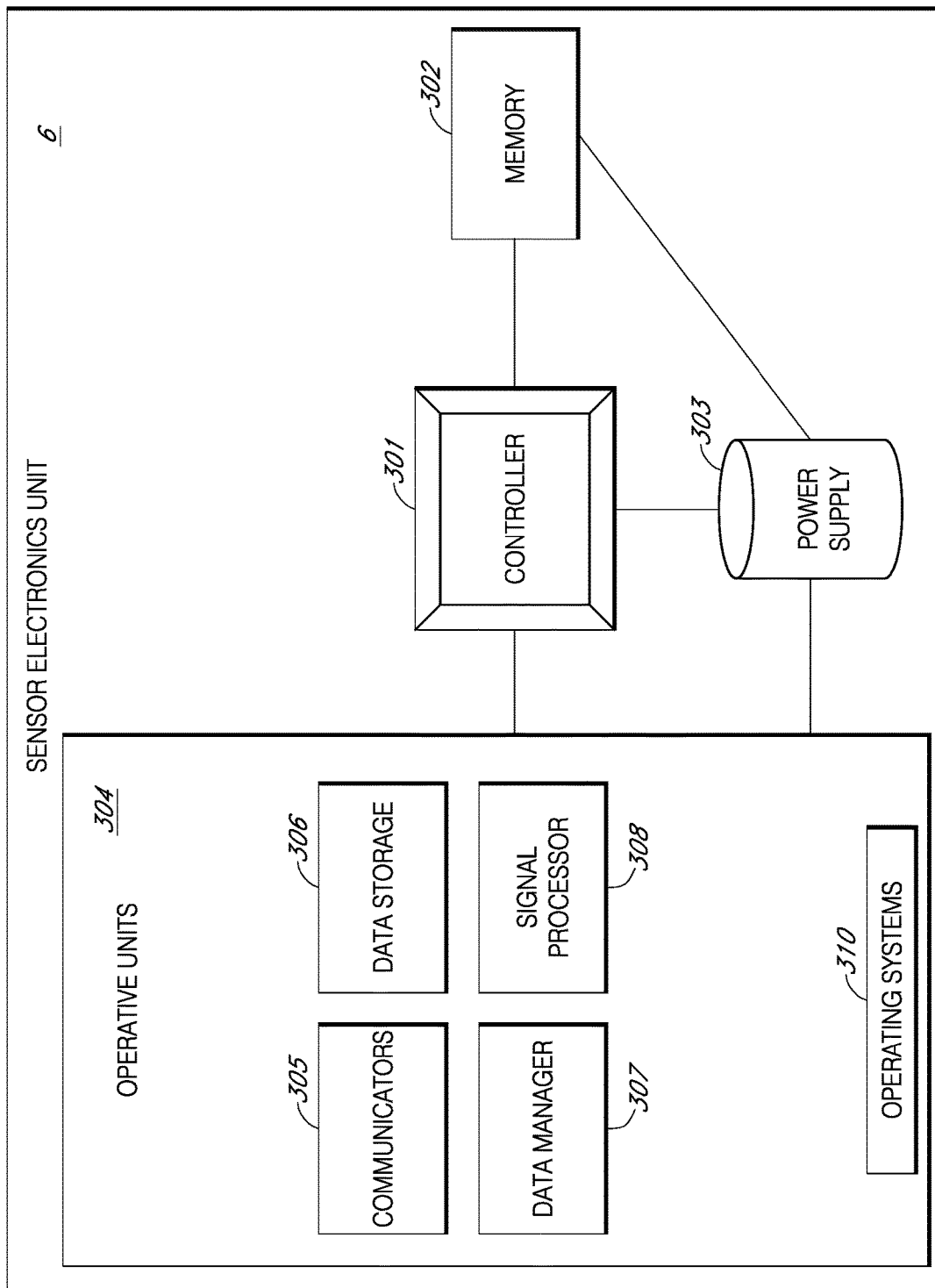
FIG. 3 illustrates a functional block diagram of an example sensor electronics unit.

FIG. 3 illustrates a functional block diagram of example Sensor Electronics Unit 6. Sensor Electronics Unit 6 can include Controller 301, Memory 302, Power Supply 303, and/or Operative Units 304, each of which can be operatively and/or communicatively coupled to each other and each other's components and/or subcomponents. Controller 301 can control the various operations performed by Sensor Electronics Unit 6. In some implementations, Sensor Electronics Unit 6 can be configured to perform the example processes, methods, and/or systems, and/or substantially similarly processes, methods, and/or systems described with reference to Sensor Electronics Units 6 throughout this disclosure.

Controller 301 can be operatively and/or communicatively coupled to Memory 302, which can include, without limitation, volatile, non-volatile, read-only memory ("ROM"), and/or random access memory ("RAM"), and can provide instructions and data to Controller 301. A portion of Memory 302 can also include non-volatile random access memory ("NVRAM"). Controller 301 can perform logical and/or arithmetic operations based on program instructions stored within Memory 302. Controller 301 can include one or more processors (e.g., microprocessors) and other peripherals. The instructions in Memory 302 can be executable to implement the methods described herein. For example, Memory 302 can be a non-transitory, computer-readable storage medium having a plurality of instructions stored thereon, the instructions being executable by a processing apparatus (e.g., Controller 301) to operate Sensor Electronics Unit 6. Operative Units 304 can be coupled to Controller 301 to perform the various operations described in this disclosure. One or more, or none, of the units in Operative Units 304 can be included in some implementations. Throughout this disclosure, reference will be made to various controllers and/or processors. In some implementations, a single controller (e.g., Controller 301) can serve as the various controllers and/or processors described. In other implementations, different controllers and/or processors can be used. Controller 301 can send and/or receive signals, such as power signals, control signals, sensor signals, interrogatory signals, status signals, data signals, electrical signals and/or any other desirable signals, including discrete and analog signals. Controller 301 can coordinate and/or manage Operative Units 304, and/or set timings (e.g., synchronously or asynchronously), turn on/off, control power budgets, receive/send network instructions and/or updates, update firmware, send interrogatory signals, receive and/or send statuses, and/or perform any operations for running features of Sensor Electronics Unit 6.

Operative Units 304 can include various units that perform functions for Sensor Electronics Unit 6. For example, and without limitation, such units of Operative Units 304 can include Communicators 305, Data Storage 306, Data Manager 307, Signal Processor 308, and/or Operating Systems 310.

In some implementations, Communicators 305 can communicatively couple Sensor Electronics Unit 6, and/or any components therein (e.g., Operative Units 304), to one or more display devices (e.g., Display Device 20A-N and/or any other display device described in this disclosure). Communicators 305 can be configured to send/receive communications over wired and/or wireless connections, such as any wired and/or wireless connection described in this disclosure. For example, and without limitation, Communicators 305 can utilize a communication protocol configured to send and/or receive data over communication channels. For example, and without limitation, such communication protocols can include BLUETOOTH®, IBEACON®, ZIGBEE®, Wi-Fi, induction wireless data transmission, radio frequencies, radio transmission, RF fields, RFID, NFC, GSM, infrared, Ethernet cables, coaxial cables, USB, firewire, data lines, wire, and/or any wired and/or wireless connection known in the art. For example, and without limitation, Communicators 305 can include an antenna, inductor, signal line, ground line, and/or any other electronics used for sending/receiving data. In the case of NFC, RFID, and/or substantially similar technologies, Communicators 305 can include readers, writers, and/or tags.

Communicators 305 can be configured to send and/or receive statuses, commands, and/or other data/information. For example, and without limitation, Communicators 305 can transmit statuses, commands, and/or data/information from Data Storage 306, Data Manager 307, Signal Processor 308, Operating Systems 310, Operative Units 304, Controller 301, Memory 302, Power Supply 303, and/or any other component and/or subcomponent of Sensor Electronics Unit 6.

Data Storage 306 can be configured to temporarily and/or permanently store (e.g., record) data. Data Storage 306 can include storage devices that can store data using different mediums, such as, without limitation, electrical (e.g., semiconductors, floating-gate transistors, hard disks, flash memory, RAM, ROM, enterprise storage, cloud, distributive storage devices, etc.), optical storage (e.g., photographic, microform, holographic, optical disk, magneto-optical drives, 3D optical data storage, holographic data storage), chemicals (e.g., organics, proteins, synapses, receptors, chemical concentrations, etc.), thermodynamics (e.g., phase change materials, heat storage devices, etc.), photochemicals (e.g., films, etc.), mechanical (e.g., switches), magnetic storage (e.g., magnetic tape, wire, etc.), etc. Data Storage 306 can also store any data and/or information based at least in part on data from any component of Sensor Electronics Unit 6, including Controller 301, Power Supply 303, Memory 302, and/or units in Operative Units 304.

Data Manager 307 can be configured to analyze and/or manage data in Data Storage 309, Memory 302, and/or any component of Sensor Electronics Unit 6 (e.g., Controller 301, Power Supply 303, and/or units in Operative Units 304). Operations that Data Manager 307 can use on such data include, but are not limited to, compression, decompression, sorting, categorizing, directing, optimizing, defragging, deleting, secure erasing, securing, manipulating, identifying, copying, pasting, write protecting (e.g., temporary write protection or permanent write protection), backing up, authenticating, etc. Data Manager 307 can also perform error monitoring, error correction, and/or data validation, including identifying and/or fixing transmission-related errors, data formatting, device-related error codes, invalid data, duplicate data points, and/or other processes on the data.

Signal Processor 308 can be configured to process any data of Sensor Electronics Unit 6, including, as a non-limiting example, data stored in Data Storage 306 and/or managed by Data Manager 307. Signal Processor 308 can perform any analysis of data presented in this disclosure, as well as other analyses and/or processes.

Power Supply 303 can include one or more batteries, including, without limitation, lithium, lithium ion, nickel-cadmium, nickel-metal hydride, nickel-hydrogen, carbon-zinc, silver-oxide, zinc-carbon, zinc-air, mercury oxide, alkaline, or any other type of battery known in the art. Certain batteries can be rechargeable, such as wirelessly (e.g., by a resonant circuit and/or a resonant tank circuit) and/or by plugging into an external power source. Power Supply 303 can also be any supplier of energy, including wall sockets and electronic devices that convert solar, wind, water, nuclear, hydrogen, gasoline, natural gas, fossil fuels, mechanical energy, steam, and/or any power source into electricity. Power Supply 303 can have sensors (not illustrated) that monitor the amount of power available. For example, and without limitation, where a battery is used, the sensors can measure the amount of battery life remaining. A sensor can detect and/or approximate the life of the battery of a Sensor Electronics Unit 6. In some implementations, the sensor for battery life can actively measure the charge, capacitance, chemical composition, or potential of a battery unit. In some cases, the sensor can be a timer that approximates the life of the Sensor Electronics Unit 6, such as 1, 2, 3, 4, 5, 6 or more months. The approximate time or percentage of battery life used or remaining may be displayed in one or more display devices and/or the sensor electronics unit 6. In some cases, the sensor can keep track of battery usage (e.g., as counts, power budgets, voltage consumption, current consumption, approximated leakage, etc.) and sum the amount of battery usage over time. A running total can be kept and compared to the total battery budget (e.g., as counts, power budgets, voltage budget, current budgets, etc.) to approximate the remaining and/or used life of the battery.

Operating System 310 can be configured to manage Memory 302, Controller 301, Power Supply 303, units in Operative Units 304, and/or any software, hardware and/or features of Sensor Electronics Unit 6. For example, and without limitation, Operating System 310 can include device drivers to manage hardware resources for Sensor Electronics Unit 6.

Any of the aforementioned components of Sensor Electronics Unit 6 can be instantiated in software and/or hardware. For example, a unit can be piece(s) of hardware and/or can be a unit/module of code run on a computer. Hardware can include processors, circuit logic, etc.

Figure 4A:
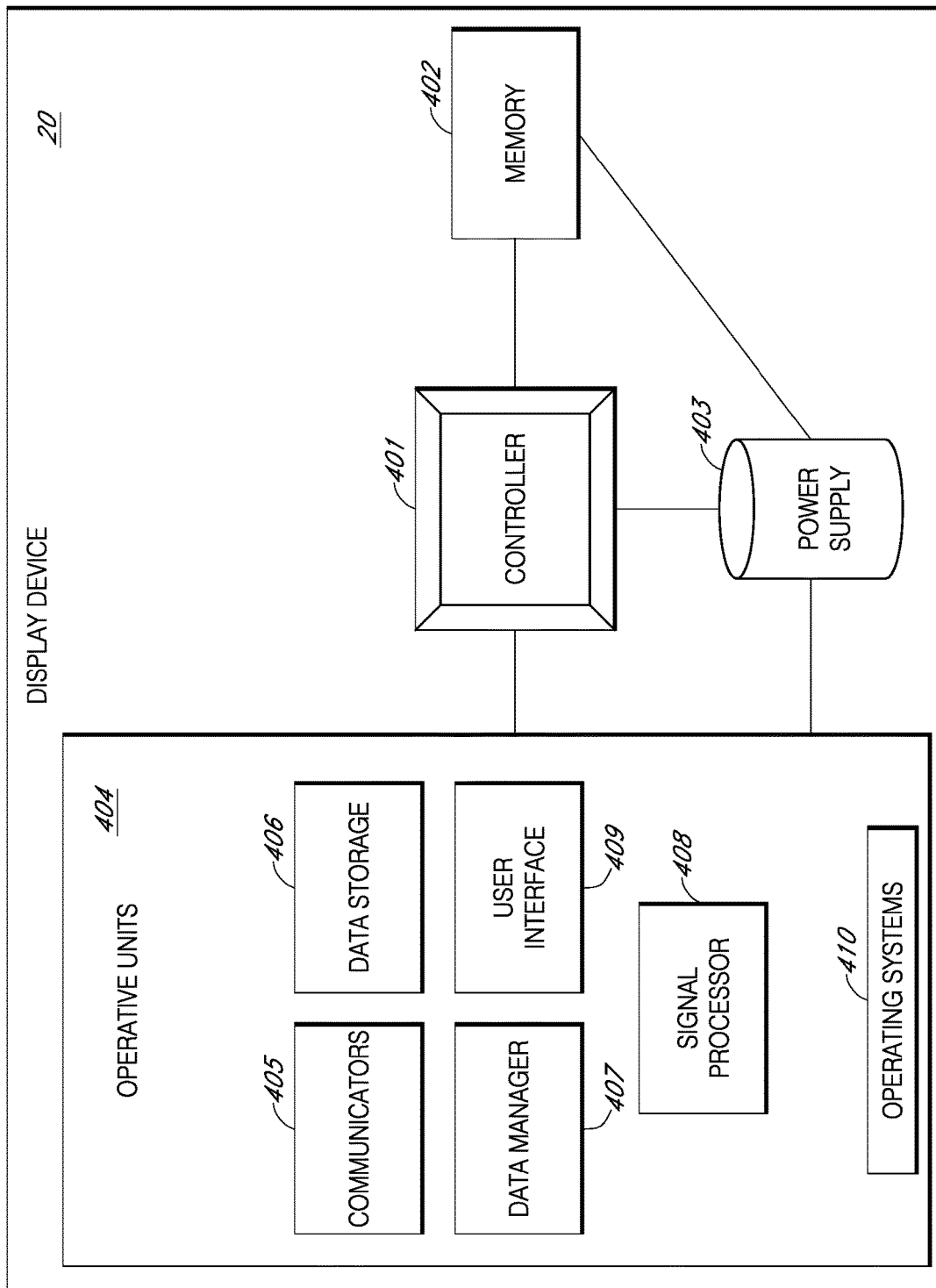
FIG. 4A illustrates a functional block diagram of an example display device.

FIG. 4A illustrates a functional block diagram of example Display Device 20. As previously mentioned, Display Device 20, as used throughout this disclosure, represents any one of Display Devices 20A-N. In some implementations, Display Device 20 can be configured to perform the example processes, methods, and/or systems, and/or substantially similarly processes, methods, and/or systems described with reference to display devices throughout this disclosure.

Controller 401 can be operatively and/or communicatively coupled to Memory 402, which can include, without limitation, volatile, non-volatile, ROM, and/or RAM, and can provide instructions and data to Controller 401. A portion of Memory 402 can also include NVRAM. Controller 401 can perform logical and arithmetic operations based on program instructions stored within Memory 402. Controller 401 can include one or more processors (e.g., microprocessors) and other peripherals. The instructions in Memory 402 can be executable to implement the methods described herein. For example, Memory 402 can be a non-transitory, computer-readable storage medium having a plurality of instructions stored thereon, the instructions being executable by a processing apparatus (e.g., Controller 401) to operate Display Device 20. Operative Units 404 can be coupled to Controller 401 to perform the various operations described in this disclosure. One or more, or none, of the units in Operative Units 404 can be included in some implementations. Throughout this disclosure, reference will be made to various controllers and/or processors. In some implementations, a single controller (e.g., Controller 401) can serve as the various controllers and/or processors described. In other implementations, different controllers and/or processors can be used. Controller 401 can send and/or receive signals, such as power signals, control signals, sensor signals, interrogatory signals, status signals, data signals, electrical signals and/or any other desirable signals, including discrete and analog signals. Controller 401 can coordinate and/or manage Operative Units 404, and/or set timings (e.g., synchronously or asynchronously), turn on/off, control power budgets, receive/send network instructions and/or updates, update firmware, send interrogatory signals, receive and/or send statuses, and/or perform any operations for running features of Display Device 20.

Operative Units 404 can include various units that perform functions for Display Device 20. For example, and without limitation, such units of Operative Units 404 can include Communicators 405, Data Storage 406, Data Manager 407, Signal Processor 408, User Interface 409 and/or Operating Systems 410.

In some implementations, Communicators 405 can communicatively couple Display Device 20, and/or any components therein (e.g., Operative Units 404), to one or more sensor electronics units (e.g., Sensor Electronics Unit 6). Communicators 405 can be configured to send/receive communications over wired and/or wireless connections, such as any wired and/or wireless connection described in this disclosure. For example, and without limitation, Communicators 405 can utilize a communication protocol configured to send and/or receive data over communication channels. For example, and without limitation, such communication protocols can include BLUETOOTH®, IBEACON®, ZIGBEE®, Wi-Fi, induction wireless data transmission, radio transmission, RF fields, radio frequencies, RFID, NFC, GSM, infrared, Ethernet cables, coaxial cables, USB, firewire, data lines, wire, and/or any wired and/or wireless connection known in the art. For example, and without limitation, Communicators 405 can include an antenna, inductor, signal line, ground line, and/or any other electronics used for sending/receiving data. In the case of NFC, RFID, and similar technologies, Communicators 405 can include readers, writers, and/or tags.

Communicators 405 can be configured to send and/or receive statuses, commands, and/or other data/information. For example, and without limitation, Communicators 405 can transmit statuses, commands, and/or data/information from Data Storage 406, Data Manager 407, Signal Processor 408, Operating Systems 410, Operative Units 404, Controller 401, Memory 402, Power Supply 403, and/or any other component and/or subcomponent of Sensor Electronics Unit 20.

Data Storage 406 can be configured to temporarily and/or permanently store (e.g., record) data. Data Storage 406 can include storage devices that can store data using different mediums, such as, without limitation, electrical (e.g., semiconductors, floating-gate transistors, hard disks, flash memory, RAM, ROM, enterprise storage, cloud, distributive storage devices, etc.), optical storage (e.g., photographic, microform, holographic, optical disk, magneto-optical drives, 3D optical data storage, holographic data storage), chemicals (e.g., organics, proteins, synapses, receptors, chemical concentrations, etc.), thermodynamics (e.g., phase change materials, heat storage devices, etc.), photochemicals (e.g., films, etc.), mechanical (e.g., switches), magnetic storage (e.g., magnetic tape, wire, etc.), etc. Data Storage 406 can also store any data and/or information based at least in part on data from any component of Display Device 20, including Controller 401, Power Supply 403, Memory 402, and/or units in Operative Units 404.

Data Manager 407 can be configured to analyze and/or manage data in Data Storage 406, Memory 402, and/or any component of Display Device 20 (e.g., Controller 401, Power Supply 403, and/or units in Operative Units 404). Operations that Data Manager 407 can use on such data include, but are not limited to, compression, decompression, sorting, categorizing, directing, optimizing, defragging, deleting, secure erasing, securing, manipulating, identifying, copying, pasting, write protecting (e.g., temporary write protection or permanent write protection), backing up, authenticating, etc. Data Manager 407 can also perform error monitoring, error correction, and/or data validation, including identifying and/or fixing transmission-related errors, data formatting, device-related error codes, invalid data, duplicate data points, and/or other processes on the data.

Signal Processor 408 can be configured to process any data of Display Device 20, including, as a non-limiting example, data stored in Data Storage 406 and/or managed by Data Manager 407. Signal Processor 408 can perform any analysis of data presented in this disclosure, as well as other analyses and/or processes.

User Interface 409 can be configured for a user to communicate with Display Device 20. For example, and without limitation, User Interfaces 409 can include touch panels, buttons, keypads/keyboards, ports (e.g., USB, DVI, Display Port, E-Sata, Firewire, PS/2, Serial, VGA, SCSI, audioport, HDMI, PCMCIA ports, memory card ports (e.g., SD and miniSD), and/or ports for computer-readable medium), mouse, rollerballs, consoles, vibrators, audio transducers, and/or any interface for a user to input and/or receive data and/or commands, whether coupled wirelessly or through wires (including, without limitation, any of the wireless or wired connections described in this disclosure). User Interface 409 can include a display, such as, without limitation, LCDs, LED displays, LED LCD displays, IPSs, cathode ray tubes, plasma displays, HD panels, 4K displays, retina displays, organic LED displays, touchscreens, surfaces, canvases, and/or any displays, televisions, monitors, panels, and/or devices known in the art for visual presentation.

Power Supply 403 can include one or more batteries, including, without limitation, lithium, lithium ion, nickel-cadmium, nickel-metal hydride, nickel-hydrogen, carbon-zinc, silver-oxide, zinc-carbon, zinc-air, mercury oxide, alkaline, or any other type of battery known in the art. Certain batteries can be rechargeable, such as wirelessly (e.g., by a resonant circuit and/or a resonant tank circuit) and/or by plugging into an external power source. Power Supply 403 can also be any supplier of energy, including wall sockets and electronic devices that convert solar, wind, water, nuclear, hydrogen, gasoline, natural gas, fossil fuels, mechanical energy, steam, and/or any power source into electricity. Power Supply 403 can have sensors (not illustrated) that monitor the amount of power available. For example, and without limitation, where a battery is used, the sensors can measure the amount of battery life remaining. A sensor can detect and/or approximate the life of the battery of a Display Device 20. In some implementations, the sensor for battery life can actively measure the charge, capacitance, chemical composition, or potential of a battery unit. In some cases, the sensor can be a timer that approximates the life of Display Device 20, such as 1, 2, 3, 4, 5, 6 or more months. The sensor can then display the approximate time or percentage of battery life used or remaining. In some cases, the sensor can keep track of battery usage (e.g., as counts, power budgets, voltage consumption, current consumption, approximated leakage, etc.) and sum the amount of battery usage over time. A running total can be kept and compared to the total battery budget (e.g., as counts, power budgets, voltage budget, current budgets, etc.) to approximate the remaining and/or used life of the battery.

Operating System 410 can be configured to manage Memory 402, Controller 401, Power Supply 403, units in Operative Units 404, and/or any software, hardware and/or features of Display Device 20. For example, and without limitation, Operating System 410 can include device drivers to manage hardware resources for Display Device 20.

Any of the aforementioned components of Display Device 20 can be instantiated in software and/or hardware. For example, a unit can be piece(s) of hardware and/or can be a unit/module of code run on a computer. Hardware can include processors, circuit logic, etc.

Figure 4B:
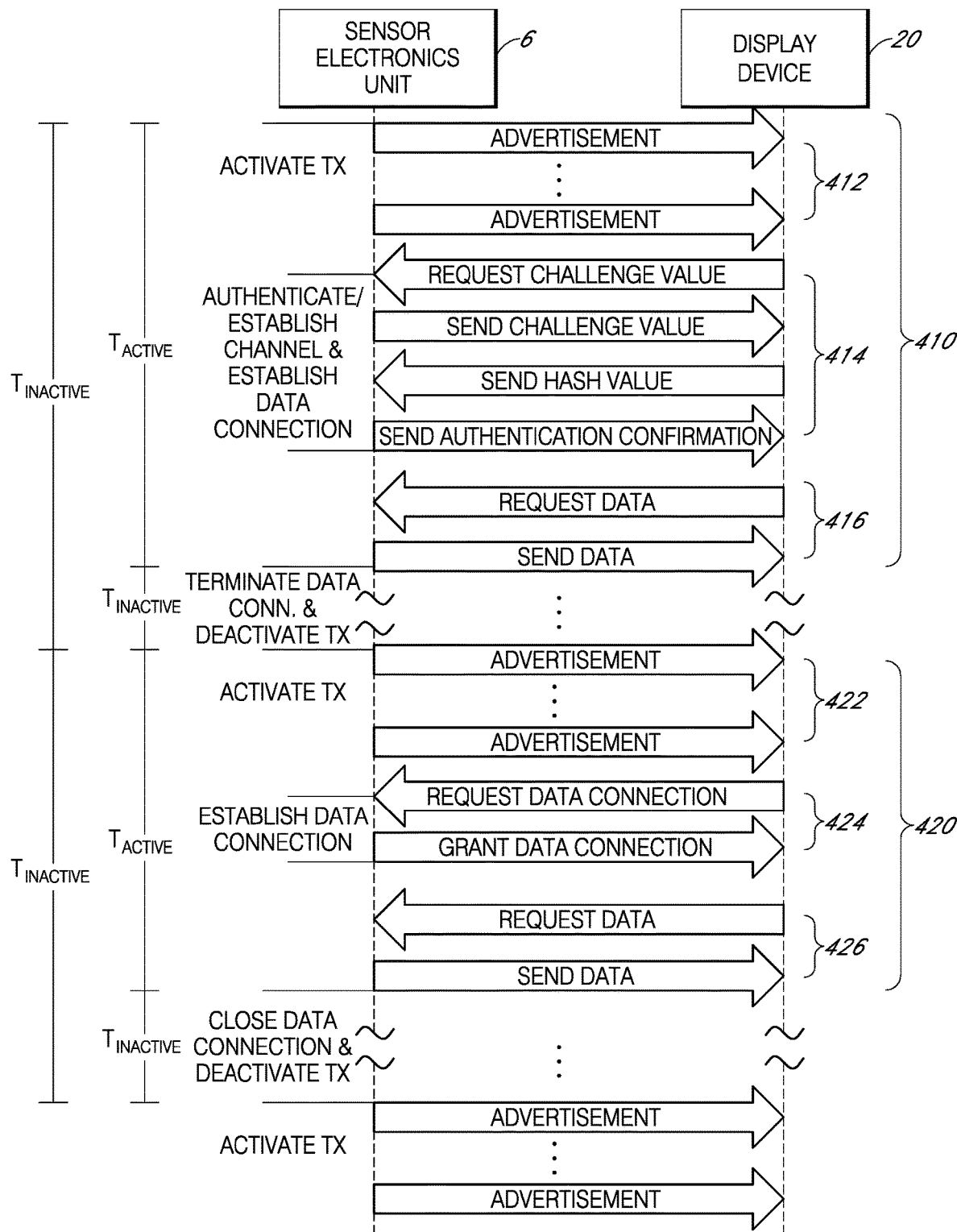
FIG. 4B is an example advertising/connection sequence between an example sensor electronics unit and an example display device.

FIG. 4B is an example advertising/connection sequence between an example Sensor Electronics Unit 6 and Display Device 20. The various tasks performed in connection with the advertising/connection illustrated in FIG. 4B may be performed by a processor/controller executing instructions embodied in a non-transitory computer-readable medium. For example, the tasks performed in connection with the procedure may be performed by hardware, software, firmware, or any combination thereof incorporated into one or more of computing devices, such as Sensor Electronics Unit 6 and/or Display Device 20. It should be appreciated that the procedure may include any number of additional or alternative tasks. The tasks shown in FIG. 4B may not be performed in the illustrated order, and the procedure may be incorporated into a more comprehensive procedure or process having additional functionality not described in detail herein.

In the example described below, the analyte values can be glucose values based on one or more measurements from Continuous Analyte Sensor 8. However, it should be understood that the analyte values can be any other analyte value described herein. The wireless data communication between Sensor Electronics Unit 6 and Display Device 20 may happen periodically, at times separated by an update interval denoted "$T_{interval}$" that may correspond to a time duration between two consecutive wireless communication sessions between a Communicators 305 of the Sensor Electronics Unit 6 (e.g., Communicators 305) and the Communicators 405 of Display Device 20 (e.g., Communicators 405). Alternatively, the update interval may be a period of obtaining and sending a recently measured glucose value. Transmitting advertisement signals, establishing a data connection (e.g., a communication channel), authentication, and requesting and sending data may occur during wireless communication sessions each lasting an active time or period (also referred to as timings) denoted "$T_{Active}$" within an update interval $T_{interval}$. In between two consecutive wireless communication sessions, the communication units can go into an inactive or sleep mode for an inactive period denoted as "$T_{Inactive}$" to conserve battery life and/or reduce peak voltage requirements, for example.

FIG. 4B illustrates an example where two such wireless communication sessions, namely, a first wireless Communication Session 410 and a second wireless Communication Session 420. Each wireless Communication Session 410, 420 starts with Sensor Electronics Unit 6 establishing a data connection with Display Device 20. To establish a data connection with Display Device 20, the Communicators Unit 305 of Sensor Electronics Unit 6 can transmit a series of Advertisement Signals 412 during the first wireless Communication Session 420. Each advertisement signal may be considered an invitation for Communicators 405 of Display Device 20 to establish a data connection with Communicators 305 of Sensor Electronics Unit 6. In some implementations, advertisement signals 412 may be embodied as advertising beacons, as will be discussed in greater detail below. It should be noted that in some implementations, Advertisement Signals 412 themselves can have advertising parameters so that directed or targeted advertising can be performed to a specific Display Device 20 or type of device.

In some cases, Sensor Electronics Unit 6 can engage in an initial system setup when Sensor Electronics Unit 44 is powered on because Sensor Electronics Unit 6 can just be turning on for the first time and/or may not be currently paired with Display Device 20. Typically, a user of Display Device 20 can identify a new and/or never-been used Sensor Electronics Unit 6 that can be paired with Display Device 20 by entering identification information (e.g., a serial number) associated with the new/unpaired Sensor Electronics Unit 6 via an application (e.g., a downloadable Java Script via the Internet and/or a mobile application downloaded from an entity that created and/or owns and/or licenses the app, and/or an app store such as from APPLE, INC. or GOOGLE INC., or other companies), running on Display Device 20 using User Interface 409. During the first wireless Communication Session 410, an authentication procedure can be performed as part of Data Connection Process 414, which can be a first data connection process. In some embodiments, information may be obtained from a passive tag or communicator 305 incorporated into the Sensor Electronics Unit 6, for instance using an NFC reader in Display Device 20 to read the passive NFC tag. For instance and without limitation, the passive NFC tag may store data such as calibration or manufacturing information including identification information associated with Continuous Analyte Sensor 8 or Sensor Electronics Unit 6. In some cases, the Display Device 20 is configured to read information from the passive tag (e.g., via communicator 405) after completion of the authentication procedure. In some cases, at least a portion of the information stored on the passive tag is encrypted. In some embodiments, the tag may be placed on a base of the sensor electronics module 6. In such embodiments, the stored information (e.g., information related to the sensor or the sensor electronics module) in the passive tag may be initially read by the display device 20. Following that, the display device may transmit the captured information to the sensor electronics module 6 or other display devices via a wireless protocol (e.g., NFC or BLE).

To establish a data connection with the Sensor Electronics Unit 6, Display Device 20 can listen continuously or periodically until an advertisement signal transmitted by the Communicators 305 of Sensor Electronics Unit 6 is received. Once the Communicators 305 of Sensor Electronics Unit 6 begin transmitting Advertisement Signals 412, it may take one, two, or more advertisement signals for Display Device 20 to receive at least one of the advertisement signals and respond to at least one of the advertisement signals. In some cases, extended advertising can consume energy and/or battery life of Sensor Electronics Unit 6. In some implementations, the Communicators 305 of Sensor Electronics Unit 6 can stop sending additional advertisement signals once Display Device 20 receives an advertisement signal and responds to that advertisement signal, for example, via an acknowledgement. In other implementations, Communicators 305 of Sensor Electronics Unit 6 can continue to send additional advertisement signals even after receiving a response from Display Device 20 so that another display device (e.g., one or more of Display Devices 20A-N), can receive and/or respond to at least one of the additional advertisement signals. After an advertisement signal is successfully received by Display Device 20, Display Device 20 and Sensor Electronics Unit 6 can engage in Data Connection Process 414.

During Data Connection Process 414, Display Device 20 can request a challenge value from Sensor Electronics Unit 6 and Sensor Electronics Unit 6 can send the challenge value to Display Device 20 in response. Upon receiving the challenge value, Display Device 20 can calculate a hash value based on the challenge value and the identification information associated with Sensor Electronics Unit 6 and/or Communicators 305 of Sensor Electronics Unit 6 and sends the hash value to Communicators 305 of Sensor Electronics Unit 6. Communicators 305 of Sensor Electronics Unit 6 can receive the hash value from Display Device 20, decode the identification information from the hash value, and verify that the received identification information matches identification information associated with Sensor Electronics Unit 6 and/or the Communicators 305 of Sensor Electronics Unit 6 previously stored in the memory of Sensor Electronics Unit 6 (e.g., Memory 302), such as during manufacturing of Sensor Electronics Unit 6. Upon verification, Communicators 305 of Sensor Electronics Unit 6 can send a signal confirming a successful authentication to Display Device 20. Once authenticated, Sensor Electronics Unit 6 and Display Device 20 can exchange information to determine how data will be exchanged (e.g., a specific frequency, time slot assignment, encryption, etc.).

After completion of the Data Connection Process 414, Sensor Electronics Unit 6 and now-connected Display Device 20 can engage in a first Data Communication 416 during which Display Device 20 can request and/or receive desired information (e.g., analyte measurement data, control information, identification information, and/or instructions) from Sensor Electronics Unit 6. When the first Data Communication 416 is completed, the data connection can be terminated (e.g., by closing the established communication channel) and the Communicators 305 and/or Controller 301 of Sensor Electronics Unit 6 can be deactivated by causing the Communicators 305 and/or Controller 301 to enter a sleep or inactive mode (e.g., low power mode or shelf mode). In some implementations, the Communicators 305 of Sensor Electronics Unit 6 can be completely or substantially completely powered down during a sleep mode (e.g., low power or shelf mode). In some implementations, the Communicators 305 of Sensor Electronics Unit 6 can be in a low power mode using only a small fraction (e.g., 1-50%) of the normal current/power. As will be discussed further below with reference to FIGS. 6C-D, as well as elsewhere throughout this disclosure, the Communicators 305 of Sensor Electronics Unit 6 may be woken up, for example, by a communication protocol using an RF field, such as NFC or RFID, which places an on-demand request from a Display Device 20.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 20 seconds and $T_{Active}$ may be between 20 and 40 seconds. As such, the Communicators 305 of the Sensor Electronics Unit 6 may be powered fully for only 10 percent (e.g., 30 seconds) of a five minute $T_{interval}$. This may significantly reduce power consumption and peak voltage demand. In some cases, that Communicators 305 may not completely power down, but enter a low-power mode when not transmitting. After an inactive time or period $T_{Inactive}$, a second wireless Communication Session 420 can start when the Communicators 305 of Sensor Electronics Unit 6 powers up again, begins transmitting a second series of Advertisement Signals 422, engages in a second data Connection Process 424 and a second data Communication Process 426 with the Communicators 405 of Display Device 20 as shown in FIG. 4B. Unlike the first data Connection Process 414, however, the second data Connection Process 424 need not involve an authentication procedure because the Sensor Electronics Unit 6 and the Display Device 20 have been successfully paired or bonded during the first wireless Communication Session 410 as described above. This process may continue, with new data connections and communications being completed at the pre-determined intervals. During all or part of each inactive period $T_{Inactive}$ during which the Communicators 305 of Sensor Electronics Unit 6 is in a sleep mode, the Controller 401 of Sensor Electronics Unit 6 can take measurement(s) of one or more analyte values using the analyte sensor and sensor measurement circuitry. For example, and without limitation, the Controller 401 or Sensor Electronics Unit 6 may take multiple analyte value measurements and average them to generate a single averaged analyte value to be transmitted in a next wireless communication session.

Continuously re-establishing a new communication channel to allow for partially or wholly powering down the Communicators 305 of Sensor Electronics Unit 6 during each update interval $T_{interval}$ can provide significant power savings. For example, the cycle of re-establishing new communication channels and powering down the Communicators 305 can allow the Sensor Electronics Unit 6 to operate for, e.g., 1 month, 3 months, 6 months, 1 year, etc., without battery replacement. It should be noted that in some implementations, battery replacement can be a function of the actual expiration of battery power or some predetermined level of remaining battery power. Furthermore, rather than globally transmitting glucose data points during the update interval $T_{interval}$, establishing specific data connections (e.g., communication channels) with only desired display devices, e.g., Display Device 20 and/or any Display Devices 20A-N, can prevent unauthorized use and interception of glucose measurement values. In some implementations, only a subset of multiple display devices (e.g., Display Device 20A-N) can be configured to receive different data such as glucose measurement values and/or alarm conditions. For example, and without limitation, in addition to a display device identifier(s), a white list may be populated with a data type identifier indicative of a type of data to be sent to that particular display device(s) populating the white list. For example, and without limitation, the particular display device(s) can have a data type identifier indicative of the display device receiving glucose measurement data and/or alarm conditions, such as low blood glucose levels. In other implementations, Sensor Electronics Unit 6 can be pre-programmed with preference or profile information, which can be accessed to determine what type(s) of data are to be sent to what display device(s). Thus, prior to the exchange of sensor information, Sensor Electronics Unit 6 can access the white list (or bonding list in some implementations) and/or preference/profile information to determine what type(s) of data should be sent to a display device. In still other implementations, initial communications between Sensor Electronics Unit 6 and a Display Device 20, the Display Device 20 can transmit type information (e.g., the type of information that the display device should receive) to Sensor Electronics Unit 6. This has a benefit of preventing all of Display Devices 20A-N communicating with Sensor Electronics Unit 6 from issuing alarms, thereby confusing and/or frustrating the user. In addition, by establishing a secure two-way communication channel, requests for specific glucose measurement values or communication of calibration or configuration information may be transmitted on an as-needed/requested basis between Sensor Electronics Unit 6 and Display Device 20.

Also, in some implementations, the Communicators 305 of Sensor Electronics Unit 6 may not be activated for data communication every update interval $T_{interval}$. Instead, Communicators 305 of Sensor Electronics Unit 6 may be activated every second, third, or fourth update interval $T_{interval}$, for example, so that communication between the Sensor Electronics Unit 6 with Display Device 20 occurs less frequently than every update interval $T_{interval}$. Doing so can further reduce power consumption. Activation could also depend on the sensor information. For example, Communicators 305 of Sensor Electronics Unit 6 need only be activated if data meets certain thresholds, such as a current rate of change, current high value, current low value, absolute difference from a previously exchanged value, percentage difference from a previously exchanged value, and the like. In some implementations, instead of skipping certain fixed update intervals, the length of each interval can be made to vary based on the sensor information or other criteria. For example, and without limitation, if the sensor information indicates a low glucose value and/or a hypoglycemic reaction is detected, the update interval value can be shortened from a normal, longer update interval value so that more frequent readings are taken and/or transmitted.

In some implementations, one or more of the update interval $T_{interval}$, the active period $T_{Active}$, and a frequency $F_{Activation}$ by which the transceiver is activated (e.g., every second, third or fourth update interval) may be variable. In certain implementations, the above-identified parameters can be user configurable (e.g., by inputting a value for the variable using user interface of Display Device 20) and/or automatically varied by the Sensor Electronics Unit 6 or Display Device 20 based on one or more criteria. The criteria can include: (i) a monitored battery power (e.g., using Power Supply 303) of Sensor Electronics Unit 6, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor is used), (ix) one or more errors detected by Sensor Electronics Unit 6 and/or Display Device 20 and/or (x) type of Display Device 20 (e.g., where Display Device 20 can be connected or populating the white list or bonding list).

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the Sensor Electronics Unit 6 and one or more of Display Devices 20.

Figure 5A:
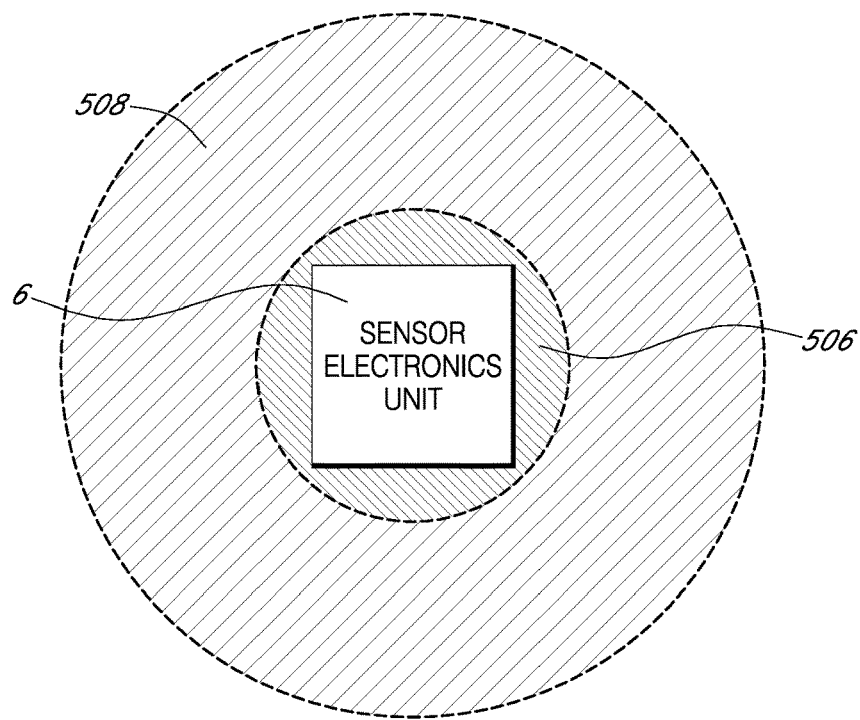
FIG. 5A illustrates example ranges of example communication protocols of an example sensor electronics unit, where each communication protocol has a different range.

In some implementations, communication protocols can have different ranges and/or different authentication protocols. FIG. 5A illustrates example ranges of example communication protocols of an example Sensor Electronics Unit 6 having two communication protocols, where each communication protocol has a different range. As described earlier, communication protocols can include any communication protocol known in the art, including those described in this disclosure. For example, and without limitation, Range 506 can be indicative at least in part of the range of RF fields, such as, without limitation, NFC or RFID. By example, where NFC has Range 506, Range 506 can be in the order of centimeters, such as ten centimeters or less. Because of the short range, in many cases, NFC can have simple and/or automatic connection between devices using the NFC communication protocol. NFC-enabled devices can include devices that work with NFC card emulation, NFC reader/writer, and/or NFC peer-to-peer. NFC can transfer data with rates in the range of 106 to 424 kbits/s, or any other speed as the communication protocol's standards are updated from time-to-time. In some cases, NFC communicates at 13.56 MHz. In some cases, the initiating device of a transmission using NFC can generate an RF field that can power the receiving device. In many cases, NFC is desirable due to its security and simplicity. However, NFC communication protocols can have limited range. NFC is sometimes considered to be included by some skilled in the art as a subset and/or outgrowth of the RFID family of technologies. Generally, RFID technologies can have variable ranges, including those having ranges up to 2000 feet. An RFID system can be Active Reader Passive Tag ("ARPT") with an active reader device that transmits interrogator signals and also receives authentication replies form passive tags. In some cases, an RFID system can be Active Reader Active Tag ("ARAT") where an active tag is awoken with an interrogator signal from an active reader. RFID can work in a range of frequency bands, such as, without limitation, 120-150 kHz, 13.56 MHz, 433 MHz, 865-868 MHz, 902-928 MHz, 2450-5800 MHz, 3.1-10 GHz. As used herein, communication protocols using RF fields can include other RF fields besides NFC or RFID, including other RF fields operating in the frequency ranges of 13.56 MHz, 120-150 kHz, 13.56 MHz, 433 MHz, 865-868 MHz, 902-928 MHz, 2450-5800 MHz, 3.1-10 GHz. NFC or RFID are merely used as illustrative examples.

Range 508 can be indicative at least in part of a second communication protocol. For example, and without limitation, the second communication protocol can utilize radio transmission, such as BLUETOOTH®. By way of illustrative example, and without limitation, in the case where the second communication protocol is BLUETOOTH®, Range

508 can be over approximately thirty feet. In some cases, BLUETOOTH® can have a user manually set up connections between devices, such as a procedure where one device detects the other device, and the devices are paired and/or authenticated. BLUETOOTH® may transmit in the ISM band from 2.4 to 2.485 GHz, or any frequency as the BLUETOOTH® standard is updated from time-to-time. BLUETOOTH® version can have relatively high speeds of data transfer, such as up to 800 kbits/s. In many cases, BLUETOOTH® is favored for its speed and range. However, there can be issues of connectivity, energy consumption, excessive handshaking, dropped packets, security, etc. As used herein, radio transmission can include other radio transmission protocols besides BLUETOOTH®, including other radio transmissions operating in the frequency range of 2.4 to 2.485 GHz. BLUETOOTH® is merely used as an illustrative example.

Figure 5B:
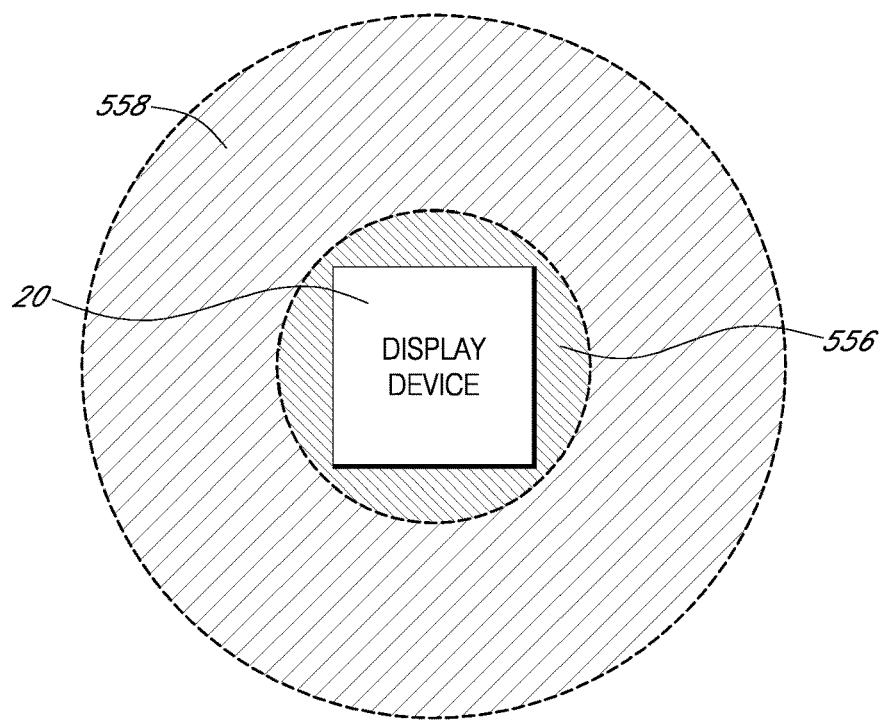
FIG. 5B illustrates example ranges of example communication protocols of an example display device, where each communication protocol has a different range.

Similarly, FIG. 5B illustrates example ranges of example communication protocols of an example Display Device 20, where each communication protocol has a different range. Ranges 556, 558 can be substantially similar to Ranges 506, 508, respectively. As mentioned, various communication protocols can be used, such as those using RF fields (e.g., NFC or RFID) or radio transmission (e.g., BLUETOOTH®).

Figure 5C:
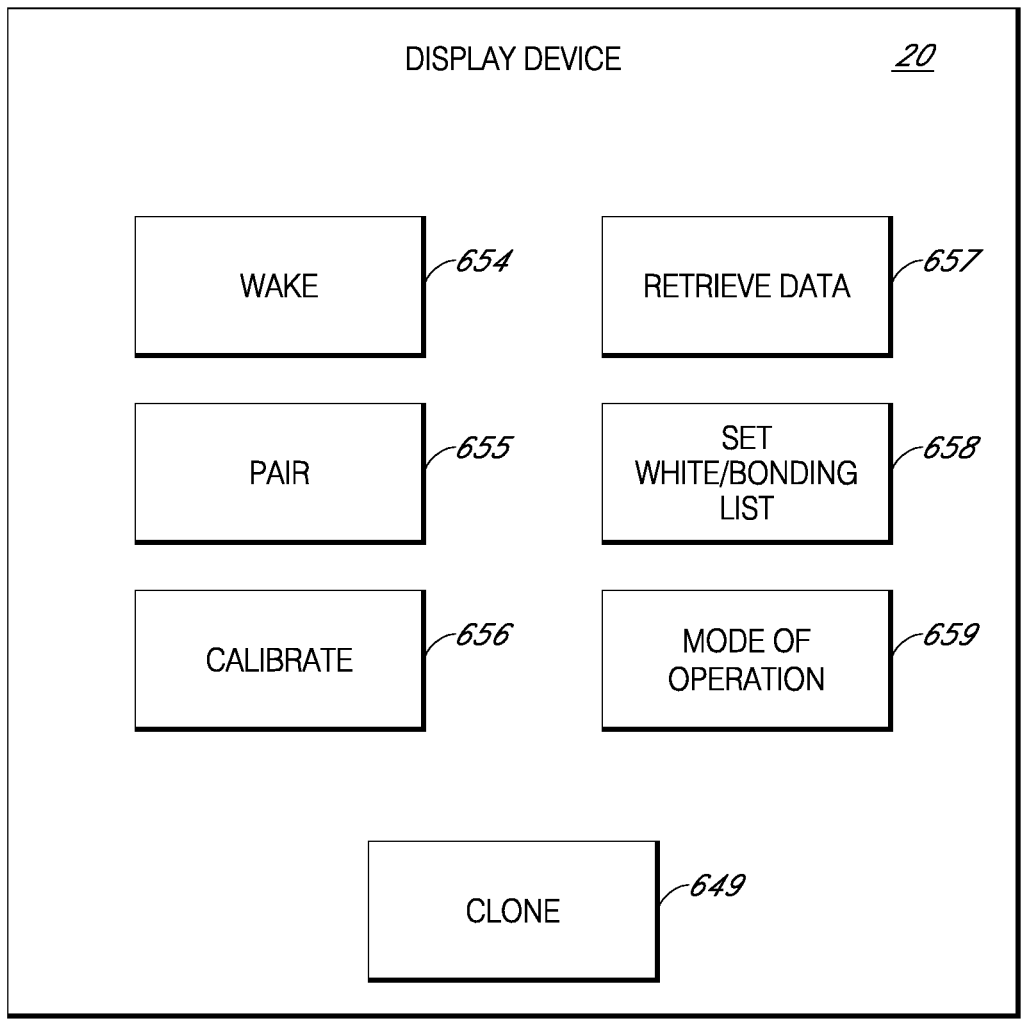
FIG. 5C illustrates an example functional block diagram illustrating example functional units of an example display device.

FIG. 5C illustrates an example functional block diagram illustrating certain functional units of Display Device 20. These functional units can be instantiated in software and/or hardware. For example, a unit can be piece(s) of hardware and/or can be a unit/module of code run on a computer. Hardware can include processors, circuit logic, etc.

Wake Unit 654 can implement a waking action where the user can use Display Device 20 to wake up a Sensor Electronics Unit 6 from, for example and without limitation, a low power mode and/or shelf mode (e.g., as described with reference to FIGS. 4B, 6C-D, as well as elsewhere throughout this disclosure). In some cases, waking up Sensor Electronics Unit 6 can include sending a wake up command to Sensor Electronics Unit 6.

Pair Unit 655 can be used to pair the Display Device 20 with Sensor Electronics Unit 6, which can be configured for communication via radio transmission (e.g., BLUETOOTH®) and/or any other communication protocol described in this disclosure. In some cases, where Display Device 20 and the Sensor Electronics Unit 6 have not been paired with that communication protocol before, Pair Unit 655 can include one or more of a command to pair, initial setup information, timing information, advertising parameters, device information, frequency, sequence, encryption/decryption information, and/or other parameters. This functionality and more will be discussed later with reference to FIG. 8, as whereas elsewhere throughout this disclosure. In cases where the Display Device 20 has paired with the Sensor Electronics Unit 6, Pair Unit 655 can include adding (if not already) the Display Device 20 to the white/bonding list, advertising to the Display Device 20, connecting, authentication, exchanging data, etc.

Calibrate Unit 656 can be used to calibrate the Sensor Electronics Unit 6. For example, and without limitation, a user can measure his/her blood glucose levels through finger pricking. He/she can enter that data (e.g., through a User Interface 409 into a field (not illustrated)) on Display Device 20 and send information based at least in part on that data to a Sensor Electronics Unit 6 over an RF field communication protocol such as NFC or RFID. Advantageously, calibration can be time sensitive where a user can desire to adjust and/or add new calibration parameters soon so that he/she has the correct readings. Advantageously, calibration using an RF field such as NFC or RFID can be accomplished on demand and without the need of following pairing procedures.

Retrieve Data Unit 657 can be used to request to retrieve data from the Sensor Electronics Unit 6. In some cases, retrieving data can comprise a command to send data over another communication protocol other than the communication protocol used to request the data. The command can comprise a request for data along with what data to send (e.g., the last 1, 2, 3, 4, 5, 6, 7, 8, 9, 10 or more data points), types of data (e.g., sensor data or electronics unit logs), timeframes of data (e.g., including time stamps), etc. By way of illustrative example, the second communication protocol used by Display Device 20 to request the sending of data from Sensor Electronics Unit 6 can utilize an RF field, such as NFC or RFID. The second communication protocol used to transfer data can be radio transmission, such as BLUETOOTH®. Advantageously, sending the data over the radio transmission instead of the RF field can allow for faster transfer rates and transfer over longer distances. For example, where it is desirable to retrieve the data on Display Device 20, a user can use that Display Device 20 to initiate data transfer from the Sensor Electronics Unit 6 to the Display Device 20 using RF fields such as NFC or RFID, and then walk further away while the data transfers over radio transmission such as BLUETOOTH®. If the data were transferred over NFC, it might take longer and/or the user would have to stay close to the Sensor Electronics Unit 6. Having the flexibility to move around, including further away, during data transfer may be advantageous for healthcare practitioners as they treat the user and other patients.

In some cases, the command to send data can be a command that requests the data to be sent over NFC. Such may be desirable when security is important (e.g., the user wants data to only be sent to close devices), the sensor electronics has little or no battery life, and/or any situation desired by a user. In some implementations, the determination of when to use NFC for data transfer can be determined by Display Device 20 or Sensor Electronics Unit 6, such as using NFC when only a small amount of data is transferred.

Set White/Bonding List Unit 658 can be used to set a white/bonding list. In some communication protocols, such as radio transmission communication protocols, can have one or more white lists and/or bonding lists that can be used by a Sensor Electronics Unit 6 to manage connected devices. The role of the white list can include a list of devices and/or their pairing information (e.g., timing information, encryption key, authentication information, advertising parameters, address, make/model, name, Generic Access Profile ("GAP"), Identity Resolving Key ("IRK"), etc.) for which Sensor Electronics Unit 6 can be paired. In some cases, the white list can be stored in memory of the Sensor Electronics Unit 6 and updated. In some implementations, there can be a predetermined number of slots in the white list, such as 1, 2, 3, 4, 5, or more slots. The display devices listed in the white list can connect for communication with Sensor Electronics Unit 6. For example, and without limitation, a Display Device 20 can be added to the white list, after which, the pairing information from the Display Device 20 can be pulled by the Sensor Electronics Unit 6 from the bonding list. Once the Display Device 20 is connected, the white list can be updated to only allow that specific Display Device 20, and other display devices on its white list, to connect.

A bonding list can include a predetermined number of slots, such as 1, 2, 3, 4, 5, or more slots. The bonding list can be stored in memory, and in some cases, it can be maintained by an application on the Sensor Electronics Unit 6 or on a display device (e.g., Display Device 20). The bonding list can contain the authentication and/or pairing information (e.g., timing information, encryption key, authentication information, advertising parameters, address, make/model, name, GAP, IRK, etc.) for a predetermined number of display devices. The display devices whose information is on the bonding list may or may not be on the white list.

In some cases, the Display Device 20 may not be on the white list. Placing that Display Device 20 may be desirable, and convenient, to the user because he/she is presently using that Display Device 20. For example, and without limitation, if a user is using a receiver, but then wants to use a smart phone and leave the receiver elsewhere, the user may desire to quickly add the smart phone to the white list. As will be described later in this disclosure with reference to FIG. 9A, in some cases, Set White/Bonding List Unit 658 can include sending a command to add the Display Device 20 to the white list of Sensor Electronics Unit 6 along with the pairing information of Display Device 20. This information can be added to any open slot in the white list. In some implementations, as will be discussed later in this disclosure with reference to FIG. 9C, Set White/Bonding List Unit 658 can include removing Display Device 20 from the white list so the Sensor Electronics Unit 6 does not communicate with it, and Sensor Electronics Unit 6 and Display Device 20 do not inadvertently connect. For example, a user can have a plurality of display devices (including Display Device 20) and may not want to get the same alerts on all of them.

In some cases, as will be discussed later in this disclosure with reference to FIG. 9D, Sensor Electronics Unit 6 can communicate with each Display Device 20 on its white list in a particular order, such as in sequential order (e.g., starting with the first slot and going to the nth slot). In such a case, some slots may allow Display Device 20 to connect and receive information relatively faster than other slots in the same white list. For example, and without limitation, some slots on the white list only allow the device to connect less frequently than when on other slots, such as only every 20 minutes instead of every 5 minutes. Also, different slots in the white list can have different parameters associated with it that can impact, for example and without limitation, the reliability of the connection. Accordingly, along with a command to add the Display Device 20 to the white list of a sensor electronics device, and any other associated data desirable (e.g., pairing information), Set White/Bonding List Unit 658 can include a request to add the Display Device 20 to a particular slot in the white list. For example, and without limitation, the Display Device 20 can request to be added to the first slot. Advantageously, this can allow the Display Device 20 to have preferable reliability and connection, and/or faster reception of data in some situations.

In some cases, adding a Display Device 20 to the white list can have repercussions to other display devices in the white list. Where the requested slot in the white list is empty, the Display Device 20's information (e.g., pairing information) can be simply added to that empty slot. However, there can be other situations. For example, and without limitation, where the Display Device 20 requests to be in a slot that is already filled, Set White/Bonding List Unit 658 can include instructions on what should be done with that previously occupying display device. In some cases, as will be discussed later in this disclosure with reference to FIG. 9D, Set White/Bonding List Unit 658 can include a request to remove the display device occupying the desired slot of the new Display Device 20. In this way, the previously occupying display device can be removed from the white list (and in some cases, the bonding list too). In other cases, as will be discussed later in this disclosure with reference to FIG. 9E, Set White/Bonding List Unit 658 can include a request that shifts the display devices in later designated slots down and removes the display device in the last slot. For example, and without limitation, in the case where there are three slots in the white list, numbered 1 to 3, each of which is filled, Set White/Bonding List Unit 658 can include a request to add the pairing display device to slot 1. A temporary white list can be made in memory holding the previous contents of the white list. The information from previous slot 1 can then be put into slot 2, and the information from previous slot 2 can be put in slot 3. The information from previous slot 3 can then not be added to the white list.

In some cases, Set White/Bonding List Unit 658 can also designate which display device should be removed from the white list. In the previous example, Set White/Bonding List Unit 658 can include a request to add the present display device to slot 1, remove the display device previously in slot 2 and shift the devices according. In that situation, the new display device would be added to slot 1, the display device previously in slot 1 would be added to slot 2, and the display device in slot 3 would stay put.

Set White/Bonding List Unit 658 can also include any number of reorderings of the white list. In some cases, the white list can be reordered without adding any new devices. Advantageously, this can allow the user to dynamically adjust his/her preferences. In these situations, Set White/Bonding List Unit 658 can include one or more requests instructing Sensor Electronics Unit 6 how to reorder the white list and/or where each device should go. In some cases, where Display Device 20 has information regarding the white list of Sensor Electronics Unit 6 beforehand (e.g., a previous exchange of the white list and/or structure of the white list from Sensor Electronics 6 to Display Device 20), this can include a white list map (e.g., a bit map and/or pointers indicating how to reorder the white list) transmitted to the Sensor Electronics Unit 6, letting the Sensor Electronics Unit 6 know where to send the contents of each slot to another slot. The white list map can include pointers or addresses indicative at least in part of which slots the presently listed display devices on the white list should go. For example, each entry in the white list map (e.g., a vector or matrix) can correspond to a slot in the white list. Each entry in that white list map can include at least the address of the slot to which the present entry in the white list should move in the updated white list. In other implementations, Set White/Bonding List Unit 658 can include an entirely new white list that will be used by the Sensor Electronics Unit 6 to replace its previous white list.

As a separate action, or included in Set White/Bonding List Unit 658, the bonding list can be set. Setting the bonding list can include a command to add or remove an item from the bonding list. Typically, the order of the bonding list does not have implications for a user, but a user could change the order of the bonding list in a similar way as described above with respect to the white list, including commands to add and/or remove particular display devices from particular slots (e.g., identified by the display device and/or the slot number) of the bonding list, and/or reorder the bonding list. The bonding list can include more slots (e.g., store more devices) than the white list.

Mode of Operation Unit 659 can include setting the mode of operation. Mode of Operation Unit 659 can include a request for the Sensor Electronics Unit 6 to go into shelf mode, low power mode, normal operation, active, sleep, transmitting, idle, battery management (e.g., to be energy efficient to reduce energy consumption such as by the use of communication protocols using RF fields, such as NFC or RFID, instead of radio transmission such as BLU-ETOOTH®) and/or any mode and/or status desired.

Clone Unit 649 can include cloning Sensor Electronics Unit 6. Cloning can include receiving and/or sending from Sensor Electronics Unit 6 one or more parameters to configure a second sensor electronics unit. By way of illustrative example, in some cases, a user may want to fully clone Sensor Electronics Unit 6 by transferring the Sensor Electronics Unit 6's data and/or configurations (e.g., pairing information, calibration data, timings, white lists, bonding lists, etc.) to another, second sensor electronics unit. As another illustrative example, only a subset of the data and/or configurations of Sensor Electronics Unit 6 may be transferred. Such can be desirable when a user only wants to clone certain aspects of the Sensor Electronics Unit 6. In some cases, pairing information may not be transferred between the Sensor Electronics Unit 6 and the second sensor electronics unit because that information may be device specific and change between the units. In any of these cases, Clone Unit 649 can use a communication protocol to transfer the one or more parameters of Sensor Electronics Unit 6 to second sensor electronics unit.

By way of illustrative example, in some cases Sensor Electronics Unit 6 and Display Device 20 may normally transfer data utilizing a first communication protocol such as a radio transmission (e.g., BLUETOOTH®). In the case where a second communication protocol utilizing an RF field, such as NFC or RFID, is used on the Sensor Electronics Unit 6, Clone Unit 649 can use the second communication protocol to transfer the data and/or configurations from Sensor Electronics Unit 6 onto Display Device 20. Display Device 20 can store the data and/or configurations in memory. In some cases, this transfer can occur while Sensor Electronics Unit 6 still has low battery life and/or after the battery of the Sensor Electronics Unit 6 has died and the second communication protocol, such as NFC, is also used to power the transfer. In some cases, before the battery of the Sensor Electronics Unit 6 dies, Sensor Electronics Unit 6 can upload the data and/or configurations of the Sensor Electronics Unit 6 to an NFC tag that can facilitate passive transfer. In some implementations, the second communication protocol could be used to initiate the cloning, but the first communication protocol could be used to actually transfer the data from one display device to another. By way of illustrative example, the first communication protocol could be a radio transmission, such as BLUETOOTH®. Display Device 20 could initiate the cloning of Sensor Electronics Unit 6 via the second communication protocol, which can utilize an RF field, such as NFC or RFID. Sensor Electronics Unit 6 could then transfer its data and/or configurations via the first communication protocol to either a second sensor electronics unit or Display Device 20. Where the data and/or configurations are transferred to Display Device 20, Display Device 20 could subsequently transfer the data and/or configurations to the second sensor electronics unit via a communication protocol, such as the first or second communication protocols, or any other communication protocol described in this disclosure. Subsequently, Display Device 20 could send the data and/or configurations to the second sensor electronics unit. In some cases, this second sensor electronics unit can use the data and/or configurations to set itself up substantially similarly to Sensor Electronics Unit 6 (e.g., with substantially similar pairings, configurations, calibrations, etc.).

Figure 6A:
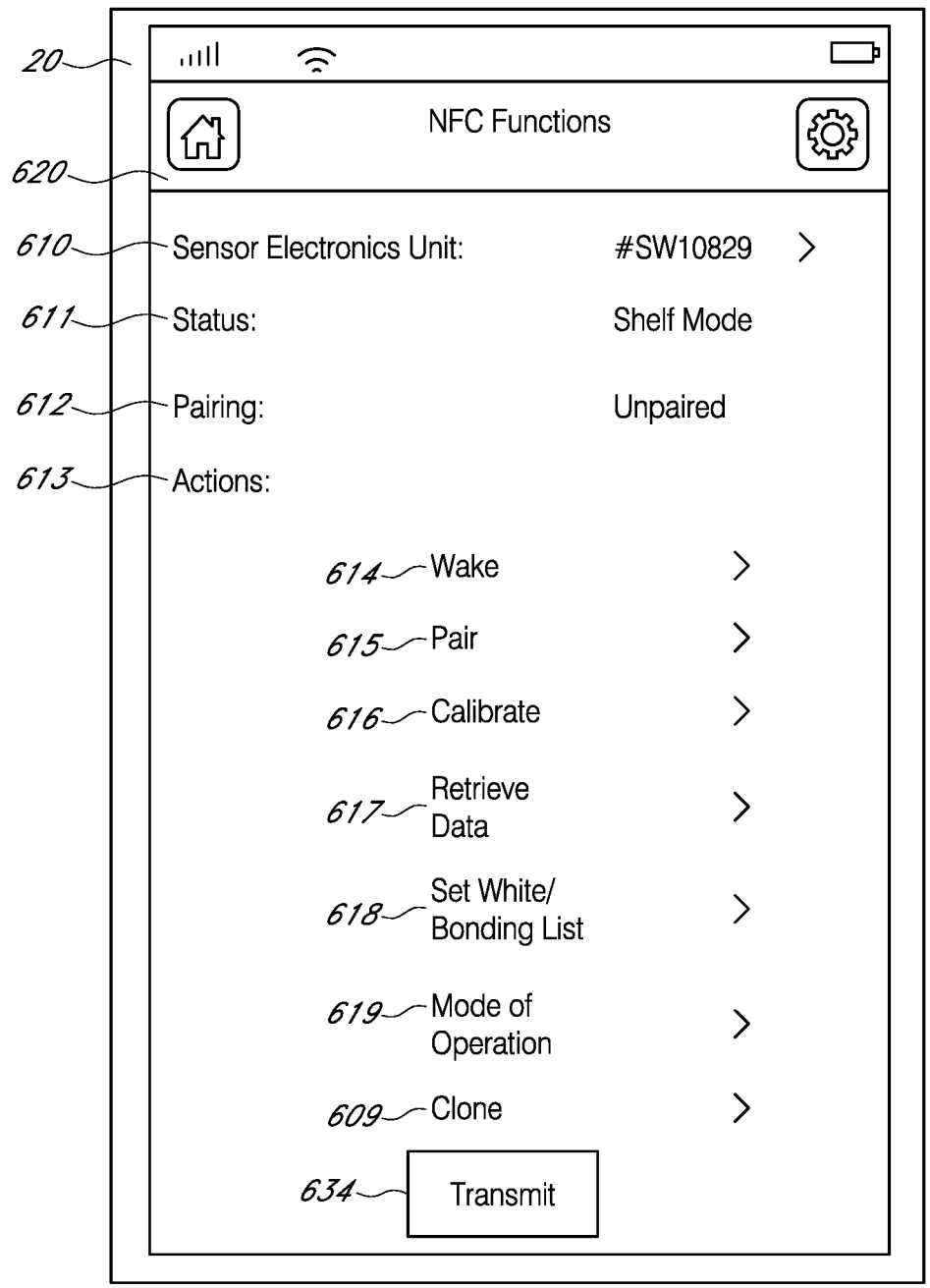
FIG. 6A illustrates an example interface where a user can select NFC functionality from an example display device.

FIG. 6A illustrates an example interface 620 where a user can select functionality corresponding to the functional units illustrated in FIG. 5C from Display Device 20. Interface 620 can be part of a mobile application (e.g., a mobile application downloaded from an entity that created and/or owns and/or licenses the app, and/or an app store such as from APPLE, INC. or GOOGLE INC., or other companies) that performs the functionality and/or has the structure described throughout this disclosure, including with reference to FIG. 5C. Interface 620 can comprise visual, audio, and/or tactile elements to interact with a user using a Display Device 20. Interface 620 can be instantiated on User Interface 409 (illustrated in FIG. 4A). A user may use Interface 620 in order to access the various functionalities of Display Device 20.

In some cases, Interface 620 can have a plurality of panels that display information and/or allow for user interaction. For example, and without limitation, Panel 610 can include a field that shows information for a sensor electronics unit (e.g., Sensor Electronics Unit 6). In some cases, by selecting the field, the user can select a sensor electronics unit with which to use sensor functionality. The sensor electronics unit can be identified by serial number, alias, name, code, and/or any identifier desired. In some implementations, the identifier can be entered manually and/or selected from a list of available (e.g., previously entered, detected, and/or paired) sensor electronics units. Panel 611 can describe a status of the sensor electronics unit identified in Panel 610. As some non-limiting examples, statuses can include one or more of: shelf mode, low power mode, normal operation, active, sleep, transmitting, idle, low battery, and/or any status description. These statuses can be retrieved and displayed by Interface 620 through a server (e.g., network, cloud, etc.) to which the sensor electronics unit sends such statuses, through other communication protocols (e.g., radio transmission or any of the communication protocols described in this disclosure), and/or through previous transmissions (e.g., via radio transmission, RF fields, and/or any other communication protocol described in this disclosure) that include status information from sensor electronics units. Panel 612 can describe the pairing status of Display Device 20 to the sensor electronics unit displayed in Panel 610. As a non-limiting example, a status of unpaired can indicate that the sensor electronics unit is not paired with the Display Device 20 over a communication protocol (e.g., radio transmission, such as BLUETOOTH®, and/or any other communication protocol described in this disclosure). Other examples can include paired (e.g., the sensor electronics unit is paired with the Display Device 20 over a communication protocol described in this disclosure), advertising, on white list, on bonding list, and/or any other pairing status.

Panel 613 can include user-selectable fields on Interface 620, which, when selected, can cause Display Device 20 to initiate corresponding actions. Panel 613 can include actions that a user can take with respect to the sensor electronics unit displayed in Panel 610. These actions include: Action 614, which can be a wake action implementing functionality corresponding at least in part to Wake Unit 654; Action 615, which can be a pair action implementing functionality corresponding at least in part to Pair Unit 655; Action 616, which can be a calibrate action implementing functionality corresponding at least in part to Calibrate Unit 656; Action 617, which can be a retrieve data action implementing functionality corresponding at least in part to Retrieve Data Unit 657; Action 618, which can be a set white/bonding list action implementing functionality corresponding at least in part to Set White/Bonding List Unit 658; Action 619, which can be a mode of operation action implementing functionality corresponding at least in part to Mode of Operation Unit 659; and Action 609, which can be a clone action implementing functionality corresponding at least in part to Clone Unit 649.

Figure 6B:
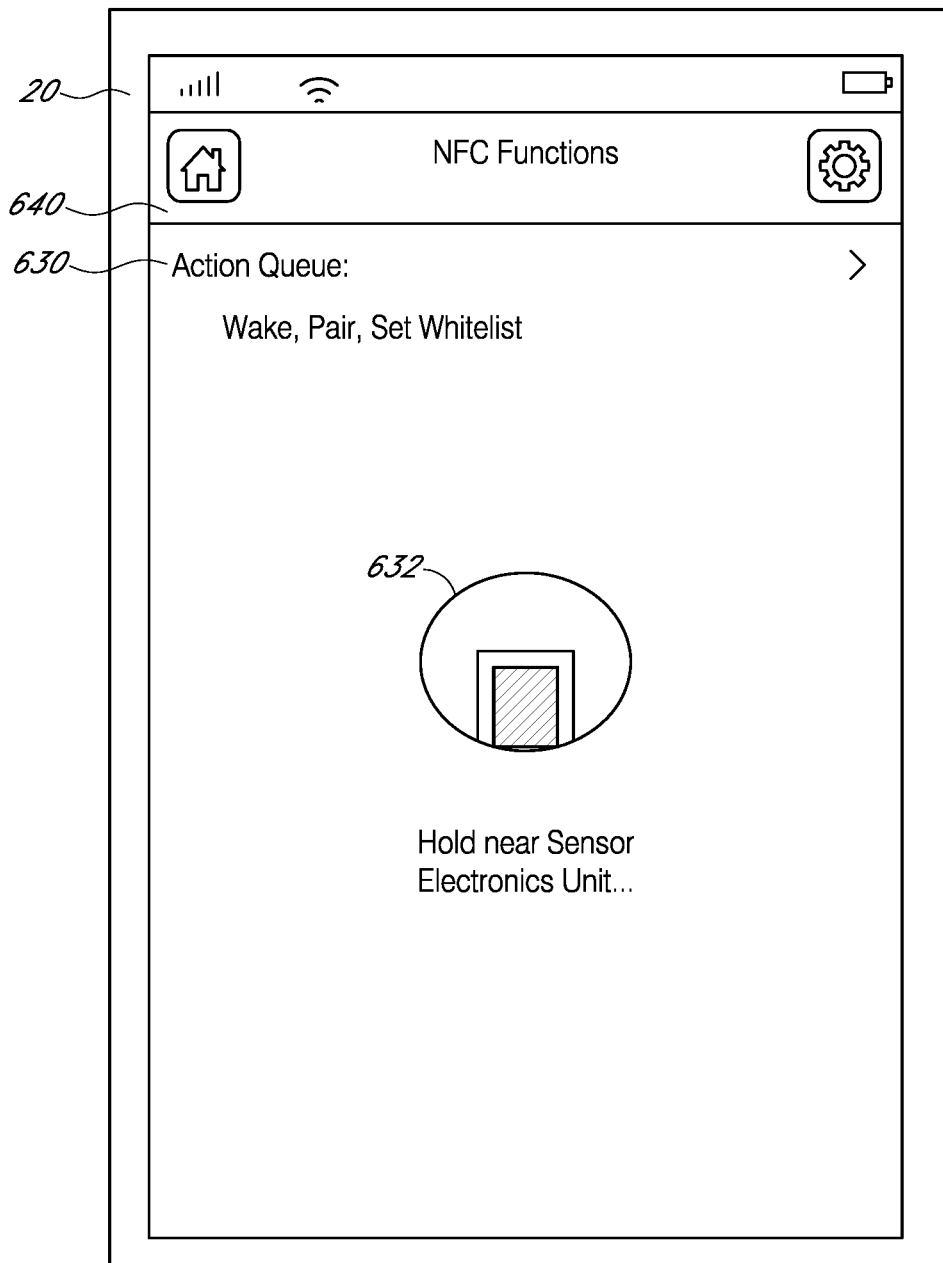
FIG. 6B illustrates an example interface for performing actions in an example action queue over NFC.

A user can add those Actions 614, 615, 616, 617, 618, 619, 609 to a Queue 630 (illustrated in FIG. 6B), which can comprise a list of the actions stored in memory. The actions on the queue can then be used to transmit the appropriate commands, data/information, etc. in order to perform those actions. These actions can be added to Queue 630 by selecting them through Interface 620 (e.g., by touching, clicking, pushing, etc. options on a touch screen or inputted using a keyboard mouse and/or any other apparatus). A person having ordinary skill in the art should appreciate that other actions can also be included in Actions 613 than those previously listed. When the user desires to transmit one or more selected actions from Panel 613, the user can select Button 634, which can then open up Interface 640 for transmission. FIG. 6B illustrates one such interface.

FIG. 6B illustrates an example Interface 640 for performing actions in an Action Queue 630 over NFC. Action Queue 630 can comprise actions selected from Action 613 (e.g., one or more of Actions 614, 615, 616, 617, 618, 619, 609) and/or other actions. In this illustrative example, instructions are transmitted from Display Device 20 to Sensor Electronics Unit 6 via NFC, however, other communication protocols can be used, including radio transmission, RF fields, and/or any other communication protocol described in this disclosure. Graphic 632 can illustrate instructions to the user and tell the user to hold the Display Device 20 near Sensor Electronics Unit 6. In some cases, these instructions can tell the user to tap Display Device 20 to the Sensor Electronics Unit 6 and/or hold the Display Device 20 near Sensor Electronics Unit. When the Display Device 20 is placed within range of Sensor Electronics Device 6, Sensor Electronics Unit 6 can then perform the items in Action Queue 630. In some cases, Display Device 20 may also display a prompt, for example, to indicate that Display Device 20 is now connected via NFC.

A. Waking Up and Putting into Low Power Mode

In some implementations, Sensor Electronics Unit 6 can be placed in a low power mode, such as shelf mode, after manufacturing to preserve battery life. This placement can be done in the factory for shipment (e.g., as described with reference to FIG. 1B) and/or it can be done by a user if he/she wants to preserve battery in Sensor Electronics Unit 6. Once a user decides to start using Sensor Electronics Unit 6, Sensor Electronics Unit 6 can be placed in its normal operational mode. Waking up Sensor Electronics Unit 6 can be difficult because, in some cases, Sensor Electronics Unit 6 may not have a user interface and/or may not be actively transmitting in order to connect to a display device (e.g., Display Device 20) that can initiate a command to wake up.

As previously discussed, in some cases, Sensor Electronics Unit 6 can use the activation of Continuous Analyte Sensor 8 that is communicatively and/or operatively coupled to Sensor Electronics Unit 6 to wake up Sensor Electronics Unit 6 from the low power mode. Sensor Electronics Unit 6 can be attachable to Continuous Analyte Sensor 8 with electrodes that allow current (or voltage) to flow between the Sensor Electronics Unit 6 and electrode. When Sensor Electronics Unit 6 detects a current (or voltage) indicative of attachment to Continuous Analyte Sensor 8, Sensor Electronics Unit 6 can wake up from the low power mode. However, this way of waking up the Sensor Electronics Unit 6 can have shortcomings in some situations. For example, and without limitation, a user can unintentionally wake up Sensor Electronics Unit 6 by touching his/her fingers across the electrodes and/or otherwise causing a change in current across the electrodes of Sensor Electronics Unit 6. In some cases, Sensor Electronics Unit 6 also may not sense the current between the electrodes all the time. Rather, it may only do so periodically, such as every 5, 10, 15, or more minutes. In such cases, a user may have to wait a significant amount of time before Sensor Electronics Unit 6 detects the current across its electrodes and wakes up from the low power mode. This can result in a poor user experience.

In some cases, Sensor Electronics Unit 6 in low power mode can draw its operating power from the RF field associated with Display Device 20 using an electromagnetic radio wave for communication. For example, and without limitation, a communication protocol such as NFC or RFID can be used by Display Device 20 to create an RF field that can allow a Display Device 20 to communicate with Sensor Electronics Unit 6 in low power mode. Advantageously, this communication protocol (e.g., NFC or RFID) can be used by Display Device 20 to wake up Sensor Electronics Unit 6 from that low power mode. The following descriptions of waking up Sensor Electronics Unit 6 can be part of Action 614 utilizing Wake Unit 654. In some implementations, Action 614 can be part of an Action Queue 630 where a plurality of actions (e.g., actions in Actions 613) can be performed.

FIG. 6C illustrates an example timing diagram where an RF field is used to wake a Sensor Electronics Unit 6 from a low power mode. The example timing diagrams are timing diagrams of Sensor Electronics Unit 6. Sensor Electronics Unit 6 can first be in low power mode (e.g., a shelf mode and/or any other low power mode) in Period 602, where the power consumption is at a lower state compared to at least one other power mode (e.g., the regular mode of operation). As discussed throughout this disclosure (e.g., with reference to FIGS. 1B, 5C), the low power mode can be used during shipment and/or in latent periods of Sensor Electronics Unit 6 use. Transmission 604 can be made using a communication protocol utilizing an RF field, such as NFC or RFID when the Sensor Electronics Unit 6 is in low power mode. Transmission 604 can be sent to Sensor Electronics Unit 6 using a Display Device 20. In some implementations, Transmission 604 can include a wake action, such as Action 614, and/or Action 614 can also include Transmission 604. Transmission 604 can include command(s), data, status(s), and/or any other desired transmissions. The wake action can also include and/or be performed in combination with other actions, such as any actions of Actions 613. For example, and without limitation, the command can include instructions requesting Sensor Electronics Unit 6 to wake up (e.g., Action 614) and/or go into a mode for normal operations (e.g., Action 659), such as a mode of operations that allows for the reception of measurements indicative of glucose measurements of the user and/or transmission of data between Sensor Electronics Unit 6 and Display Device 20. In some cases, Sensor Electronics Unit 6 can advertise to Display Device 20 in the mode for normal operation. This advertising can initiate right after or substantially right after the Sensor Electronics Unit 6 awakens from the low power mode.

In some implementations, other commands can tell Sensor Electronics Unit 6 to perform tasks, such as read data and/or current/voltage from a Continuous Analyte Sensor 8 and/or send the Display Device 20 data, statuses, commands, etc. Commands can also include commands relating to changing mode of operation, calibrate measurement circuitry, turn on/off sensor circuits, adjust defined parameters or presets, etc. These commands can also include any commands described with respect to Actions 613. In some cases, Transmission 604 can include energy (e.g., energy transmitted for powering via NFC) that can be used to power from Display Device 20 delivered to the Sensor Electronics Unit 6 in order to power the reception of the command and/or any steps desired to perform the command. For example, and without limitation, Transmission 604 can include energy from the Display Device 20 sent to Sensor Electronics Unit 6 (e.g., via NFC) so that the Sensor Electronics Unit 6 can receive a wake-up command and increase its power usage. In some cases, the received power by Sensor Electronics Unit 6 can allow Sensor Electronics Unit 6 to go from a low power mode to a normal power mode. Once it is in a normal power mode, it can then power its own activities. In some cases, the energy received by Sensor Electronics Unit 6 can power the whole transition (e.g., all the actions/steps taken by Sensor Electronics Unit 6) from the low power mode to a higher power mode. In some cases, the energy received by the Sensor Electronics Unit 6 does not power the whole transition to a normal power mode, but can sufficiently power Sensor Electronics Unit 6 to receive the command to change to the higher power mode from the low power mode.

Data from the Display Device 20 sent to the Sensor Electronics Unit 6 in Transmission 604 can include data about the Display Device 20 (e.g., serial number, authentication, security information, make/model, etc.). In some cases, this data (alone or in combination with sent commands, statuses, etc.) can facilitate pairing between Sensor Electronics Unit 6 and Display Device 20 using other communication protocols. Statuses can include the status of the display device, and/or any information relating to the functionality of the display device (e.g., ready, standby, errors in operation, etc.). During, after, or both during and after Transmission 604, the Sensor Electronics Unit 6 can go into normal operation in Period 606. Period 606 can occur after Time Delay 608 from Transmission 604. Time Delay 608 can be a predetermined delay (e.g., 5, 4, 3, 2, 1, or less seconds).

Where NFC or RFID is used, Transmission 604 can be sent using a tap-to-start initiation. In particular, where NFC is used, NFC can have ranges that are in the order of a few centimeters (e.g., ten centimeters or less), where a user can bring Display Device 20 close to and/or touch Sensor Electronics Unit 6 to send Transmission 604. Such physical interaction can be advantageous by giving the user a physical initiation that can be intuitive. As described throughout this disclosure, tap-to-start initiation can be desirable in a variety of instances. By way of illustration, and without limitation, tap-to-start initiation can be used to wake up Sensor Electronics Unit 6 from a low power mode. It can also be used generally to change the power mode of Sensor Electronics Unit 6 when desirable (e.g., to shelf, mode, normal operation, high power mode, etc.). In some cases, NFC can be used to transmit commands, data, calibration information, etc. between Display Devices 20 and Sensor Electronics Unit 6. Desirably, using NFC generally or in a tap-to-start initiation can be advantageous to allow a user to change the settings of Sensor Electronics Unit 6 without having to go through multiple steps for pairing (e.g., as with BLUETOOTH®) and/or authentication. Such use of NFC can also allow reliable data and command transmission, and can also be performed on-demand without having to wait on transmission timings of other communication protocols such as BLUETOOTH®.

In some implementations, normal operation in Period 606 can include utilizing the communication of protocol of Transmission 604. In some implementations, normal operation in Period 606 can include using a second communication protocol, such as a communication protocol that utilizes radio transmission. In some implementations, this second communication protocol may not be the same communication protocol as the first communication protocol. By way of illustrative example, this second communication protocol can include BLUETOOTH®. In some examples, after transmitting data via the second communication protocol, the Sensor Electronics Unit 6 can return to the low power mode.

Figure 6D:
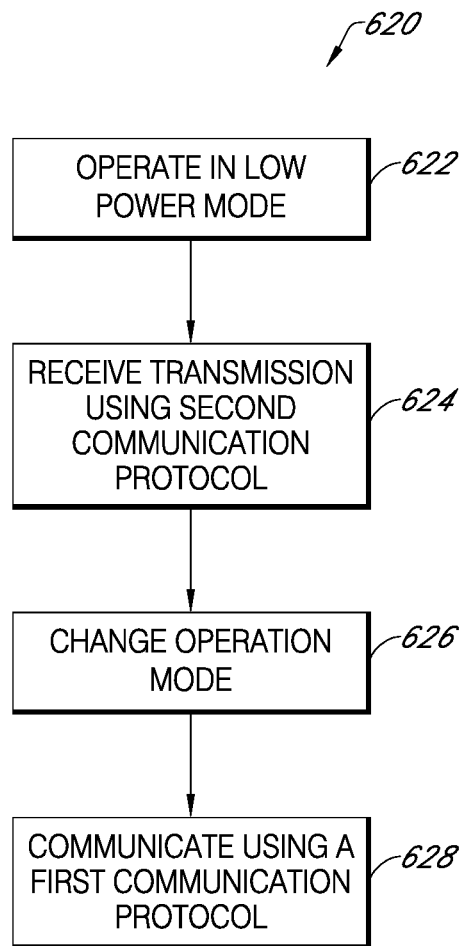
FIG. 6D illustrates an example flow chart illustrating the process of waking up an example sensor electronics unit using an RF field communication protocol.

FIG. 6D illustrates an example flow chart illustrating the process described in FIG. 6C. In some cases, a user of a Display Device 20 may desire to use Method 620 when he/she desires to pair his/her Display Device 20 to Sensor Electronics Unit 6 substantially on demand. For example, and without limitation, some white lists may only let Display Device 20 connect at predetermined intervals, such as every 20 minutes. Instead of waiting for that timing, a user may desire to connect Display Device 20 to Sensor Electronics Unit 6 substantially right away. By way of illustration, a user may want to add a Display Device 20 to a white list instantly during an emergency where there are no other display devices available for use. Sensor Electronics Unit 6 can be sensing analyte measurements of the user, or of someone else (e.g., someone under the care of a user). Accordingly the user may use Method 620 to pair Display Device 20 to Sensor Electronics Unit 6 on demand to facilitate assistance during the emergency. As another illustrative example, a health practitioner may want to pair Display Device 20 to a patient's Sensor Electronics Unit 6 right away as the health practitioner makes rounds. Because the health practitioner may not have time to wait for the predetermined time interval of the white list, the health practitioner may appropriately use Method 620 to connect instantly with the sensor electronics unit 6 of the user. As another illustrative example, a user may just find it inconvenient to wait the predetermined time interval to connect the Sensor Electronics Unit 6 to a Display Device 20. Accordingly, such a user may desire to use Method 620 to connect the Display Device 20 to the Sensor Electronics Unit 6 substantially on demand In Block 622, Sensor Electronics Unit 6 can operate in a low power mode. In Block 624, Sensor Electronics Unit 6 can receive a signal using a first communication protocol. By way of illustrative example, the second communication protocol can utilize an RF field, such as NFC or RFID by Sensor Electronics Unit 6 and/or Display Device 20. This transmission can comprise commands, such as, without limitation, commands for pairing of a first communication protocol, changing mode of operation, calibrate measurement circuitry, turn on/off sensor circuits, adjust defined parameters or presets, etc. The transmission can also include any action, such as, without limitation, Actions 613. By way of illustration, and without limitation, this transmission can include a plurality of actions queued by a user using the Display Device 20. In some cases, these actions can include one or more of: a mode of operation action (e.g., Action 619), a pairing action (e.g., Action 615), and/or a set white/bonding list action (e.g., Action 618). Advantageously, a mode of operation action can allow Sensor Electronics Unit 6 to switch from low power mode to a different mode of operation, such as a normal mode of operation. A pairing action can allow the Display Device 20 to communicate with Sensor Electronics Unit 6 using the second communication protocol to pair to the Sensor Electronics Unit 6 using a first communication protocol. For example, and without limitation, a second communication protocol using an RF field, such as NFC or RFID, can be used to pair a Sensor Electronics Unit 6 with a Display Device 20 for communications using first communication protocol, such as one using radio transmission (e.g., BLUETOOTH®), by exchanging pairing information for that first communication protocol. As described in this disclosure, a set white list action can be used to change the order of the white list of Sensor Electronics Unit 6 for the first communication protocol as desired. In some cases, this action can include instructions in how to reorder the white list, pointers for changing the white list, a copy of a new white list, and/or any other way of setting the white list described in this disclosure (e.g., as described previously with reference to FIGS. 5C, 6A). Any other action described in this disclosure can be also be used. Advantageously, this can allow a user flexibility and convenience in setting up connections. In some implementations, Display Device 20 can autonomously determine actions to queue, such as based at least in part on patterns of user utilization (e.g., based on the uses of one or more of Actions 614, 615, 616, 617, 618, 619, 609 at particular times of day, and/or particular situations, so Display Device 20 learns to initiate those same of Actions 614, 615, 616, 617, 618, 619, 609 at those same times of day and/or situations) and/or on needs of the Display Device 20 (e.g., retrieving missing data).

Next, in Block 626, Sensor Electronics Unit 6 can change from the low power mode to the desired operation mode. By way of illustrative example, various operation modes can be used, such as, without limitation, a normal operation mode, calibration mode, blind mode (e.g., a mode where all or some data is not displayed on a Display Device 20), and/or any desirable mode. In some cases, in Block 626, the desired operation mode can be a normal operation mode.

In Block 628, the Sensor Electronics Unit 6 can then communicate using a first communication protocol, including, without limitation, a radio transmission such as BLUETOOTH® and/or any other communication protocol described in this disclosure. As the Sensor Electronics Unit 6 communicates using this first communication protocol, it can do so without further user interaction because it already received information, such as pairing information, by the second communication protocol.

In some implementations, instead of waking up a Sensor Electronics Unit 6 from a lower power mode, such as shelf mode, a user may desire to put a Sensor Electronics Unit 6 in another operating mode into a low power mode. For example, and without limitation, a user may only want to monitor glucose once a week or every month. Because some Sensor Electronics Unit 6 may have predetermined (or limited) battery lives, putting the Sensor Electronics Unit 6 into low power mode can allow Sensor Electronics Unit 6 to be used for more days.

FIG. 6E illustrates an example timing diagram of Sensor Electronics Unit 6 that is put into a low power mode. In Period 652, Sensor Electronics Unit 6 can have normal operation, or any operation using more power/energy than a low power mode. In normal operation, Sensor Electronics Unit 6 can communicate using one or more communication protocols, such as any communication protocol mentioned in this disclosure including radio transmission such as BLUETOOTH®. In some implementations, Transmission 654 can put Sensor Electronics Unit 6 into a low power mode during Period 656 using a command, such as a command telling Sensor Electronics Unit 6 to go into a low power mode and/or a low power initiation command. Period 656 can occur after Time Delay 658 from Transmission 654.

Time Delay 658 can be a predetermined delay (e.g., 5, 4, 3, 2, 1, or less seconds). Transmission 654 can be made using any communication protocol described in this disclosure. By way of illustrative example, Transmission 654 can be made using an RF field for communication, such as NFC or RFID, or using radio transmission, such as BLUETOOTH®. Where NFC is used, since NFC can have ranges that are in the order of a few centimeters (e.g., ten centimeters or less), a user can bring a Display Device 20 close to and/or touch Sensor Electronics Unit 6 to send Transmission 654. Such physical interaction can be advantageous by giving the user a physical initiation that can be intuitive. Using radio transmission such as BLUETOOTH® can be advantageous because the Display Device 20 may be further away from Sensor Electronics Unit 6 and/or may already be communicating over radio transmission such as BLUETOOTH® to Sensor Electronics Unit 6.

In some implementations, the low power mode can be a shelf mode, or other power modes that use less power. For example, and without limitation, as mentioned with reference to FIGS. 1B, 6A, the low power mode can be a mode that turns off one or more of a transmission circuit (e.g., a BLUETOOTH® radio), measurement circuitry, sensory circuitry, processors, etc. It can also reduce the frequency of refreshes, advertisements, resolution of measurements, and/or any other periodic activities of a Sensor Electronics Unit 6. Sensor Electronics Unit 6 can later be woken up in a process substantially similar to the process described with respect to FIGS. 6C-D.

As was mentioned in this disclosure with reference to FIGS. 6A-B, a wake action (e.g., Action 614 and/or other waking action described in this disclosure) can be performed in combination with other actions, such as one or more of Actions 613. These actions can be performed in a queue, such as Action Queue 630. For example, and without limitation, waking up a Sensor Electronics Unit 6 can be combined with any one or more of Actions 614, 615, 616, 617, 618, 619, 609.

B. Out-of-Sync Communication

In some cases, communications sent by Sensor Electronics Unit 6 can follow certain communication patterns, such as, without limitation, the communication patterns described with reference to FIGS. 6C, 6E. However, in some cases, a user may desire to send/receive communications that do not follow the timing of that communication pattern. By way of example, and without limitation, a retrieve data action, such as Action 617, can be used by a display Device 20 to retrieve data from Sensor Electronics Unit 6 out of the communication pattern. As was mentioned in this disclosure, a retrieving data action (e.g., Action 617 and/or other waking action described in this disclosure) can be performed in combination with other actions, such as one or more of Actions 613. These actions can be performed in a queue, such as Action Queue 630.

Figure 7A:
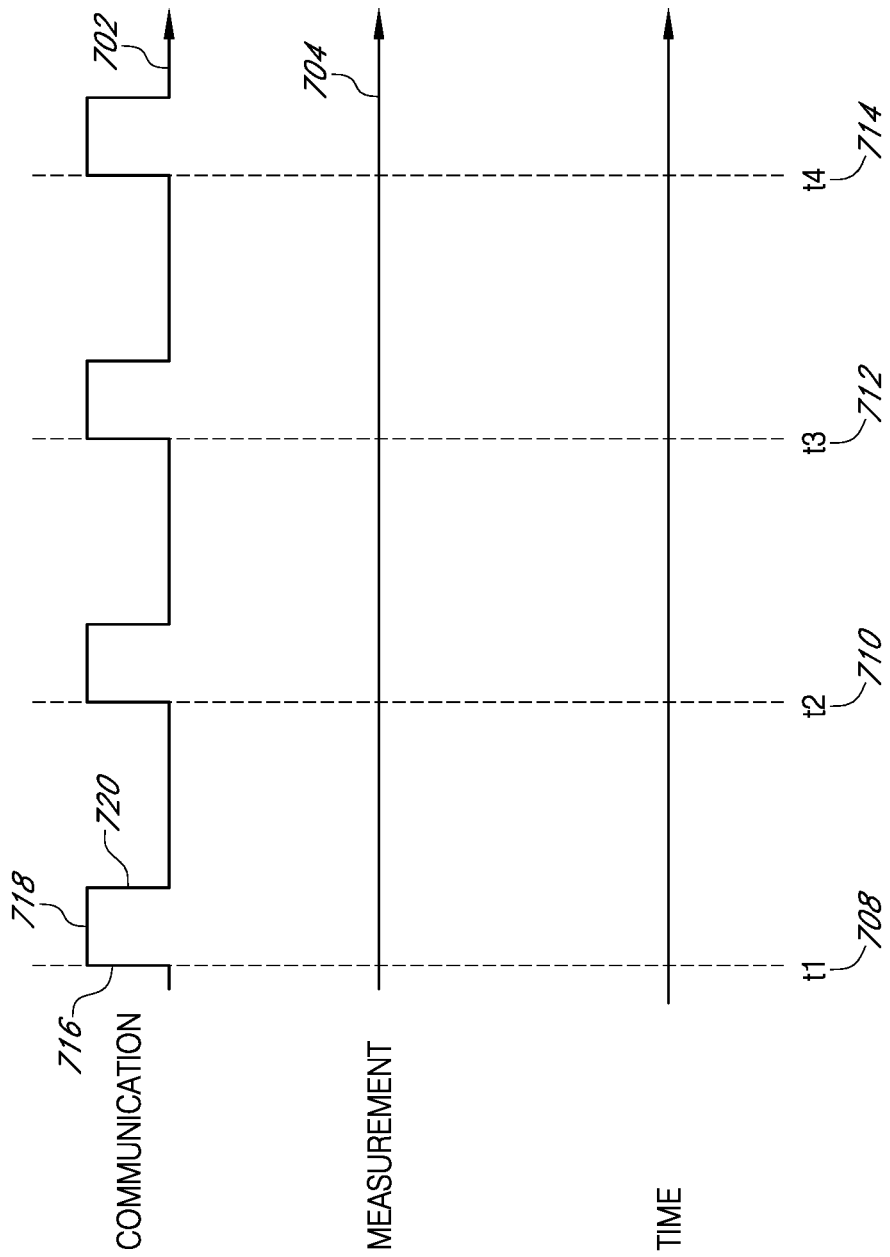
FIG. 7A illustrates an example timing diagram of an example first communication protocol for an example sensor electronics unit.

FIG. 7A illustrates an example timing diagram of an example first communication protocol for Sensor Electronics Unit 6. Measurement Line 704 illustrates that Sensor Electronics Unit 6 can receive measurements substantially constantly. Measurement Line 704 can represent analog and/or digital measurements. In the case of a digital measurement, the continuous line of Measurement Line 704 can represent a recurring reception of discrete digital data measurements.

Communication Line 702 illustrates the timing of a first communication protocol where the Sensor Electronics Unit 6 sends communications indicative of the measurements taken to one or more Display Devices 20A-N. At these times, Sensor Electronics Unit 6 can also receive communications. For example, and without limitation, radio transmission such as BLUETOOTH® can be used as the first communication protocol on Communication Line 702 to send data indicative of blood glucose measurements from Sensor Electronics Unit 6 to Display Device 20. The communications can occur periodically, such as occurring at Times 708, 710, 712, 714.

In some implementations, the time between each sequential Times 708, 710, 712, 714 can be 5, 10, 15, 20 minutes or more as desired. At each of Times 708, 710, 712, 714, a Sensor Electronics Unit 6 can send communications along Communication Line 702. As a non-limiting example, at Time 708, a communication window between Sensor Electronics Unit 6 and Display Device 20 can initiate with Rising Edge 716. Sensor Electronics Unit 6 can then actively send/receive communications for a predetermined amount of time on Edge 718, where the communication window is open. For example, and without limitation, the predetermined amount of time can be 10, 15, 20, 25, 30, 35, 40 or any desired number of seconds. The communication window can then close with Falling Edge 720. In some cases, the amount of time can be related at least in part to the amount of data transmitted and/or the transmission time for that data.

By way of illustrative example, and without limitation, Times 708, 710, 712, 714, and the relationship between them, can be indicative of the frequency in which communications occur, which can be variable based on user-defined settings and/or predetermined transmission frequencies based on activities. For example, and without limitation, a period of 5 minutes or less between two consecutive measurement transmissions (e.g., between Time 708 and Time 710, Time 710 and Time 712, and/or Time 712 and Time 714) can be used when the user desires to have very regular and/or frequent data points on his/her blood glucose levels. Such regular and/or frequent data points can be desirable when the user is going through normal activities such as walking, working, routine exercise, driving, etc. so that he/she can analyze trends in those activities. As another non-limiting example, a period of 20 minutes or more between two consecutive measurement transmissions (e.g., between Time 708 and Time 710, Time 710 and Time 712, and/or Time 712 and Time 714) can be used when a user does not desire many data points. For example, and without limitation, a user's blood glucose levels may be relatively normal or stabilized. By not transmitting measurement data as frequently, a user can extend the life of Sensor Electronics Unit 6 and/or Continuous Analyte Sensor 8. As another non-limiting example, periods of time between two consecutive measurement transmissions (e.g., between Time 708 and Time 710, Time 710 and Time 712, and/or Time 712 and Time 714) can be dynamic and/or variable based on activities and/or conditions. For example, a shorter period of time can be used if a clinically risky situation is detected, such as conditions indicative at least in part of hyperglycemic or hypoglycemic events. In those situations, Sensor Electronics Unit 6 and/or Display Device 20 can detect when a user's blood glucose levels fall below a hypoglycemic glucose level threshold or above a hyperglycemic glucose level threshold. In those cases, Sensor Electronics Unit 6 can increase its connection establishment frequency such that the period of time between two consecutive measurement transmissions is reduced. As another example, Sensor Electronics Unit 6 and/or Display Device 20 can detect when a user is sleeping and transmit measurement data more frequently as there may be risks for diabetics of having a hypoglycemic state while sleeping. The period of time between consecutive measurement transmissions can also be variable on a predetermined schedule, such as transmitting more frequently during meal times. In some cases, the time period between consecutive measurement transmissions can be set by sending a command and the time period between those consecutive measurement transmissions over NFC or RFID so that a user can tap (or bring in substantially close proximity) a Display Device 20 to Sensor Electronics Unit 6. Advantageously, this can allow a user to set the frequency of measurement transmission on demand.

Figure 7B:
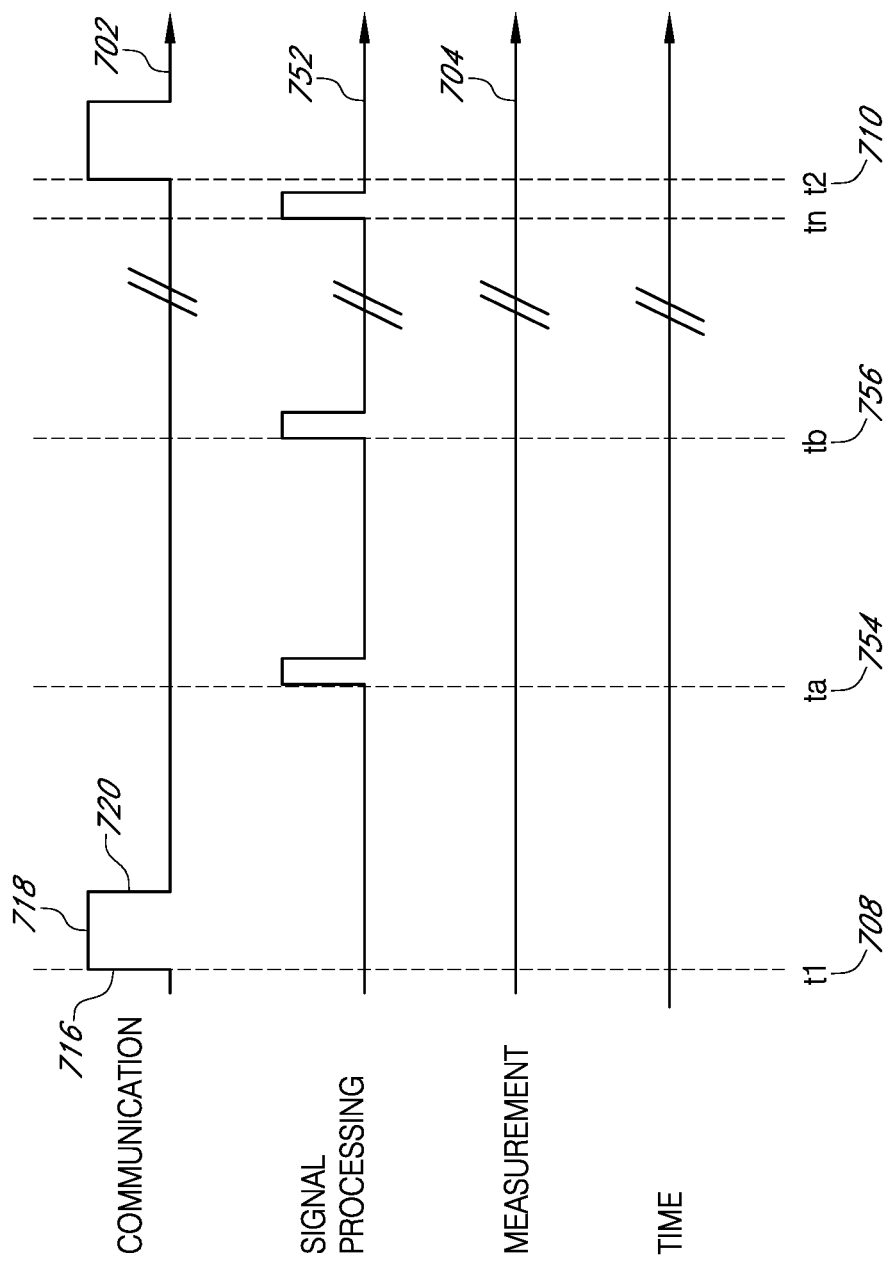
FIG. 7B illustrates an example timing diagram of an example sensor electronics unit showing signal processing that can occur between the communications of the first communication protocol of FIG. 7A.

FIG. 7B illustrates an example timing diagram of Sensor Electronics Unit 6 showing signal processing that can occur between the communications of the first communication protocol of FIG. 7A. For example, and without limitation, Sensor Electronics Unit 6 can perform signal processing on measurement data periodically between communications, such as communications on Communication Line 702. Signal Processing Line 722 illustrates the timing of the signal processing. By way of illustrative example, and without limitation, communication windows can open at Times 708, 710, as described with respect to FIG. 7A. Between Times 708, 710, a signal processor (e.g., a processor substantially similar to Signal Processor 308) can perform signal processing at Times 724, 726, and/or other predefined times. Such signal processing can include any signal processing described in this disclosure. In some cases, the signal processing can include data aggregation where the measurements taken since the last communication are compiled and processed to determine, e.g., analyte measurement trends, blood glucose measurements, and/or other indicia of blood glucose levels and/or the health of the user of Sensor Electronics Unit 6. In some cases, a conversion function can be used to convert measured unprocessed data into processed data, such as estimated glucose values. The signal processing can also determine the state of the user (e.g., normal, hypoglycemic, hyperglycemic) and initiate an alarm and/or notification if there are any health concerns.

Figure 7C:
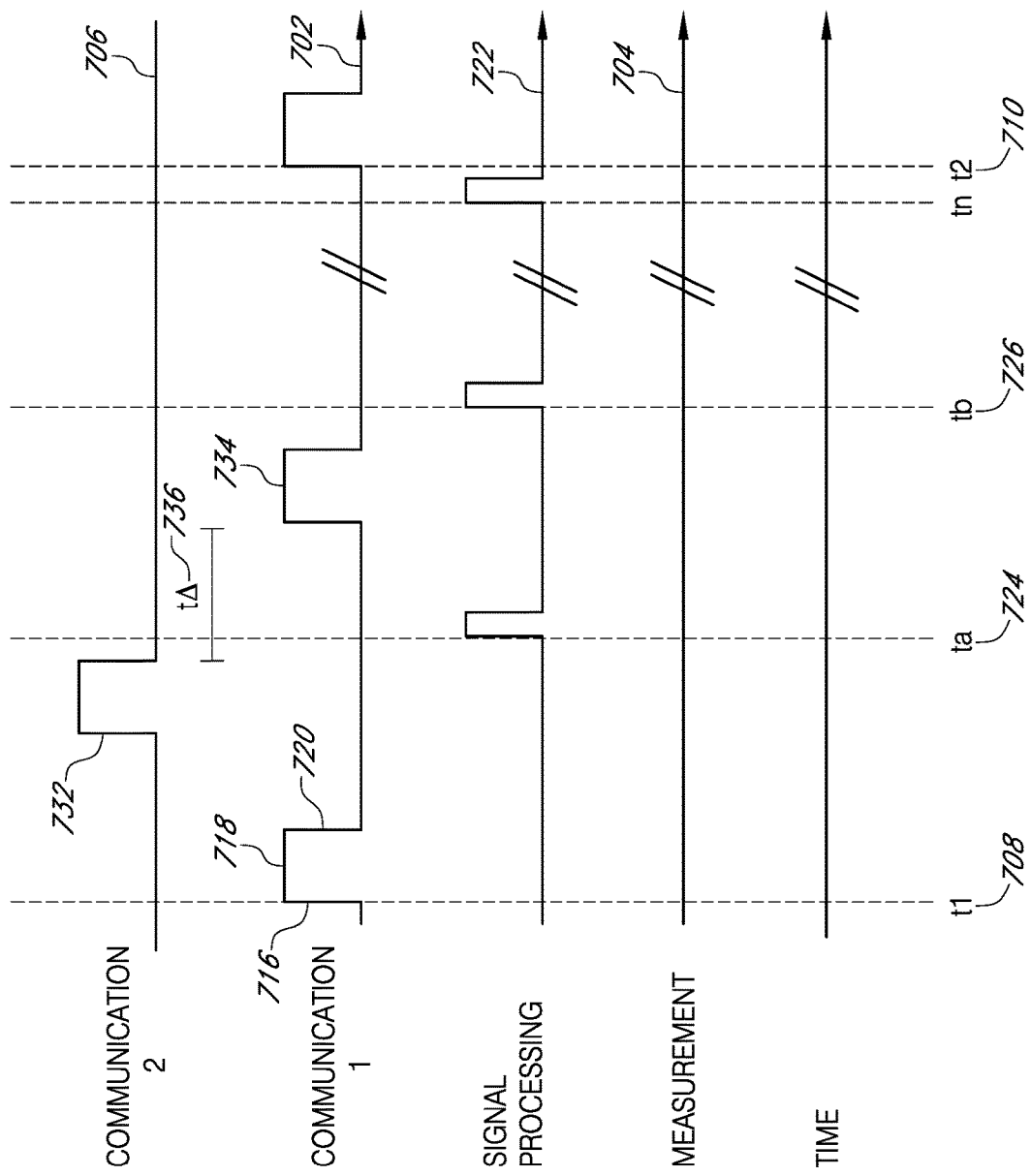
FIG. 7C illustrates an example transmission from an example sensor electronics unit using a second communication protocol to initiate a communication using the first communication protocol from the example timing diagram of FIG. 7B.

FIG. 7C illustrates an example transmission from Sensor Electronics Unit 6 using a second communication protocol to initiate a communication using the first communication protocol from the example timing diagram of FIG. 7B. For example, and without limitation, Transmission 732 can utilize a second communication protocol, such as a communication protocol utilizing an RF field, including but not limited to NFC or RFID, on Communication Line 706. Transmission 732 can further include a command to initiate communication along the first communication protocol (e.g., utilizing a radio transmission such as BLUETOOTH®) whose timing is represented by Communication Line 702. Other transmissions in Transmission 732 can include those associated with a retrieve data action, such as Action 617. That communication can occur after Time Delay 736, which can be a predetermined delay (e.g., 5, 4, 3, 2, 1, or less seconds). For example, and without limitation, Waveform 734 can represent an additional communication window opening. In some implementations, this additional communication window opening can send aggregated measurements as processed by Sensor Electronics Unit 6 unit prior to Transmission 732. By way of illustration, and without limitation, data aggregated by processing initiated at Time 724 can be sent during Transmission 734 in response to Transmission 732. Transmission 734 can occur after Time Delay 736 from Transmission 732. Advantageously, in some implementations, Transmission 734 can occur without altering and/or shifting the schedule communication window openings on Communication Line 706. This ability to not alter and/or shift the schedule of communications can allow a user to receive/send data without then having to wait for the whole communication timing (e.g., the time period between Time 710 and Time 708) for the next communications, as may be the case had the communication schedule been altered.

In other implementations, instead of Transmission 734, a transmission of data can utilize communications using the second communication protocol. For example, and without limitation, Display Device 20 can send Transmission 732 to Sensor Electronics Unit 6 to send recent data. Sensor Electronics Unit 6 can then return data to Display Device 20 using the second communication protocol.

C. Starting or Stopping Sensor Sessions

In some cases, a user may desire to start a new sensor session and/or end a prior sensor session. For example, and without limitation, in some cases, Continuous Analyte Sensor 8 can have a certain life for usage on a user. By way of illustrative example, and without limitation, a user may use Continuous Analyte Sensor 8 for 1, 2, 3, 4, 5, 6, 7, 8, 9, 10, 14 or more days, or any amount of time in which Continuous Analyte Sensor 8 was constructed to function, before changing Continuous Analyte Sensor 8. For example, and without limitation, the amount of time Continuous Analyte Sensor 8 can function can be called a sensor session. Starting or stopping a sensor session can be performed in combination with other actions, such as one or more of Actions 613. These actions can be performed in a queue, such as Action Queue 630.

By way of illustrative background, components of a Sensor Electronics Units 6 may be replaced periodically. For example, and without limitation, Continuous Analyte Sensor 8 may be attached to a Sensor Electronics Unit 6, where it can be desirable to replace Continuous Analyte Sensor 8 periodically (e.g., every 7-30 days). Sensor Electronics Unit 6 can be configured to be powered and/or active for much longer than Continuous Analyte Sensor 8, where Sensor Electronics Unit 6 can have power for 1, 2, 3, 4, 5, 6 or more months until its power supply (e.g., a battery and/or Power Supply 303) runs out of life. Replacing these components can be difficult and costly, including time and monetary costs for assistance from trained personnel. Reducing the replacement of such components, including the battery if replaceable, significantly improves the convenience of Sensor Electronics Unit 6 to a user.

In some implementations, when the Sensor Electronics Unit 6 is used for the first time (or reactivated once a battery has been replaced in some cases), it can be connected to Continuous Analyte Sensor 8. Display Device 20 and Sensor Electronics Unit 6 can initially establish communications when Sensor Electronics Unit 6 is first used or re-activated (e.g., the battery is replaced). Once Display Device 20 and Sensor Electronics Unit 6 have established communication, Display Device 20 and Sensor Electronics Unit 6 may periodically and/or continuously be in communication over the life of several sensors (e.g., Continuous Analyte Sensor 8) until, for example, the battery or the entirety of Sensor Electronics Unit 6 is replaced. Each time the sensor is replaced, notifications of a new sensor can be sent/exchanged via communication protocols (e.g., any communication protocol described in this disclosure) between the Sensor Electronics Unit 6 and Display Device 20.

In accordance with some implementations, Sensor Electronics Unit 6 can gather and/or process sensor measurements from Continuous Analyte Sensor 8 and periodically send sensor information representative of the sensor measurements to Display Device 20. Measurements can be gathered and transmitted over the life of Continuous Analyte Sensor 8 (e.g., in the range of 1 to 30 days or more). In some cases, measurements can be transmitted often enough to adequately monitor analyte levels, such as blood glucose levels. Rather than having the radio-frequency ("RF") circuitry of Sensor Electronics Unit 6 and Display Device 20 continuously communicating, Sensor Electronics Unit 6 and Display Device 20 may regularly and/or periodically establish a communication channel between them. Thus, Sensor Electronics Unit 6 can communicate wirelessly with Display Device 20 at predetermined time intervals. The duration of the predetermined time intervals can be selected to be long enough so that Sensor Electronics Unit 6 does not consume an undesired amount of energy/power by transmitting data too frequently, yet frequent enough to provide substantially real-time sensor information (e.g., measured analyte values) to one or more of display devices for output to a user. As described in this disclosure, this transmission of data can occur at predetermined time intervals and/or irregularly/aperiodically as desired.

A user may desire to start a sensor session after connecting a new sensor (e.g., Continuous Analyte Sensor 8) to Sensor Electronics Unit 6. In starting a new sensor session, Sensor Electronics Unit 6 (and in some cases a Display Device 20) recognizes that a new sensor is being used and can initialize and calibrate that sensor. Similarly, a user may desire to stop a sensor when the user desires to replace the sensor. Also, in some cases, a user may not start/end a sensor session while connecting/disconnecting from a sensor. Instead, by way of non-limiting examples, the user may desire to start/stop a user session to synchronize data collection to a particular time, stop collecting data, and/or reconnect after a poor connection between a Sensor Electronics Unit 6, sensor (e.g., Continuous Analyte Sensor 8), and/or Display Device 20. Having such ability can allow the user to get data more quickly and/or have a better user experience. In some cases, stopping a sensor session may be desirable where the sensor is no longer collecting data and/or the sensor is collecting bad data. Stopping the sensor session at this time can prevent bad data from continuing to be processed by Sensor Electronics Unit 6 and/or prevent Display Device 20 from alerting a user that no data and/or bad data is being collected.

However, in some implementations, starting/stopping sensor sessions can be unintuitive and/or difficult for a user. For example, and without limitation, returning to FIG. 7A, Communication Line 702 illustrates the timing of a first communication protocol where the Sensor Electronics Unit 6 opens a communication window and can send/receive communications indicative of the measurements taken with a Display Device 20. For example, and without limitation, the first communication protocol can utilize radio transmission such as BLUETOOTH®, which can be used to send data indicative of blood glucose measurements. The communication windows can open periodically, such as occurring at Times 708, 710, 712, 714. In this example, where a user desires to start or stop a sensor session, the user can use a second communication protocol, different than the first communication protocol. The second communication protocol can include a communication protocol creating an RF field, such as NFC or RFID.

Figure 7D:
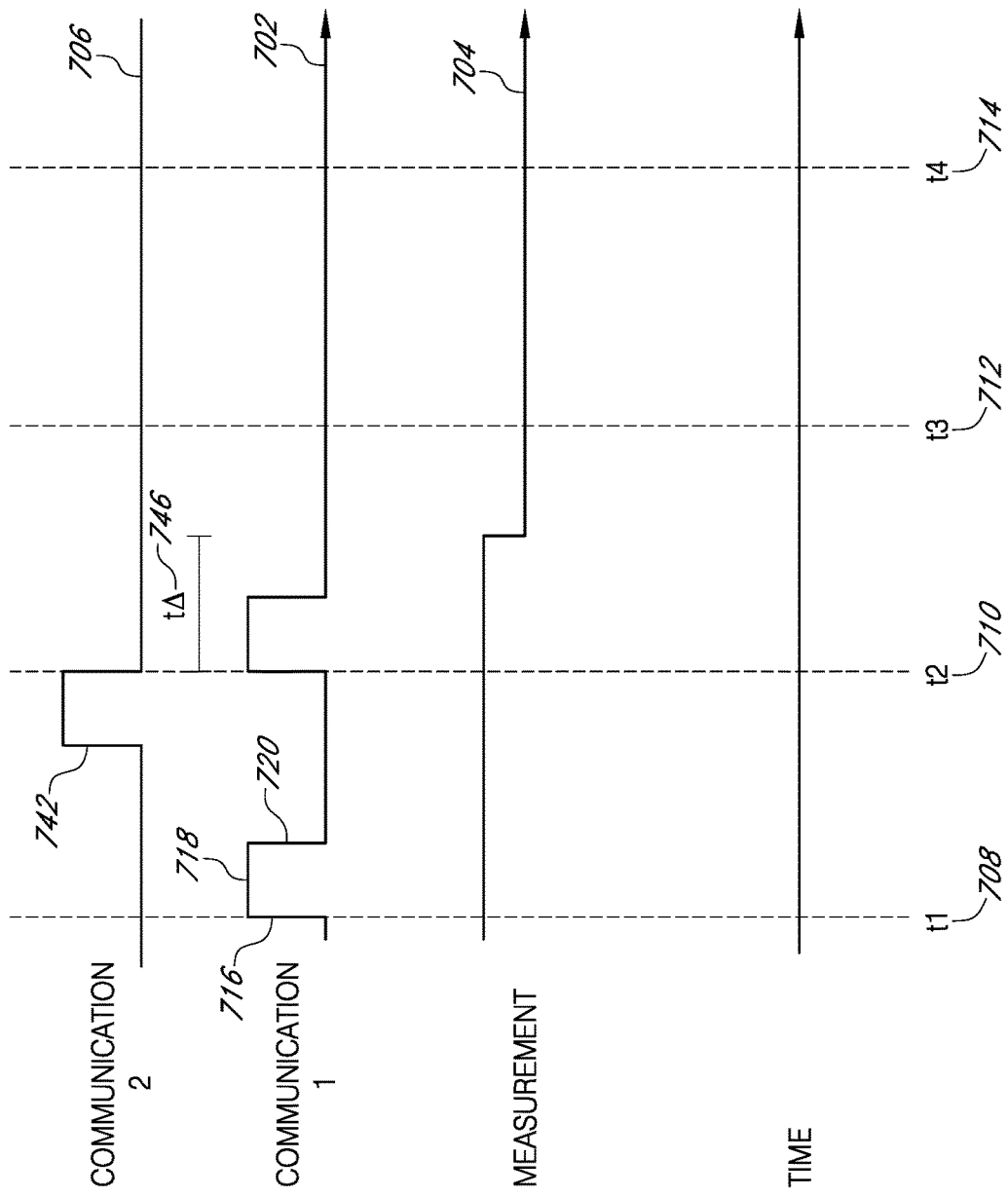
FIG. 7D illustrates an example timing diagram showing a transmission over a second communication protocol that stops an example sensor session.

FIG. 7D illustrates an example timing diagram showing a transmission over a second communication protocol that stops a sensor session, such as the sensor session referenced in FIG. 7A. In this illustrative example, Transmission 742 can utilize a second communication protocol, such as a communication protocol creating an RF field, including NFC or RFID, along Communication Line 706. Transmission 742 can include commands or instructions to stop measurements and/or stop sending data over a radio transmission, such as BLUETOOTH®. The receipt of Transmission 742 can stop measurements and communications along the first communication protocol on Communication Line 702 (e.g., closing communications over Communication Line 702). In some implementations, there can be a delay after Transmission 742 before measurements and communications along the first communication protocol stop. This delay can be Time Delay 746, which can be a predetermined delay (e.g., 5, 4, 3, 2, 1, or less than 1 second) set by a user or automatically by Sensor Electronics Unit 6 and/or Display Device 20. After Time Delay 746, measurements on Measurement Line 704 can turn off.

Figure 7E:
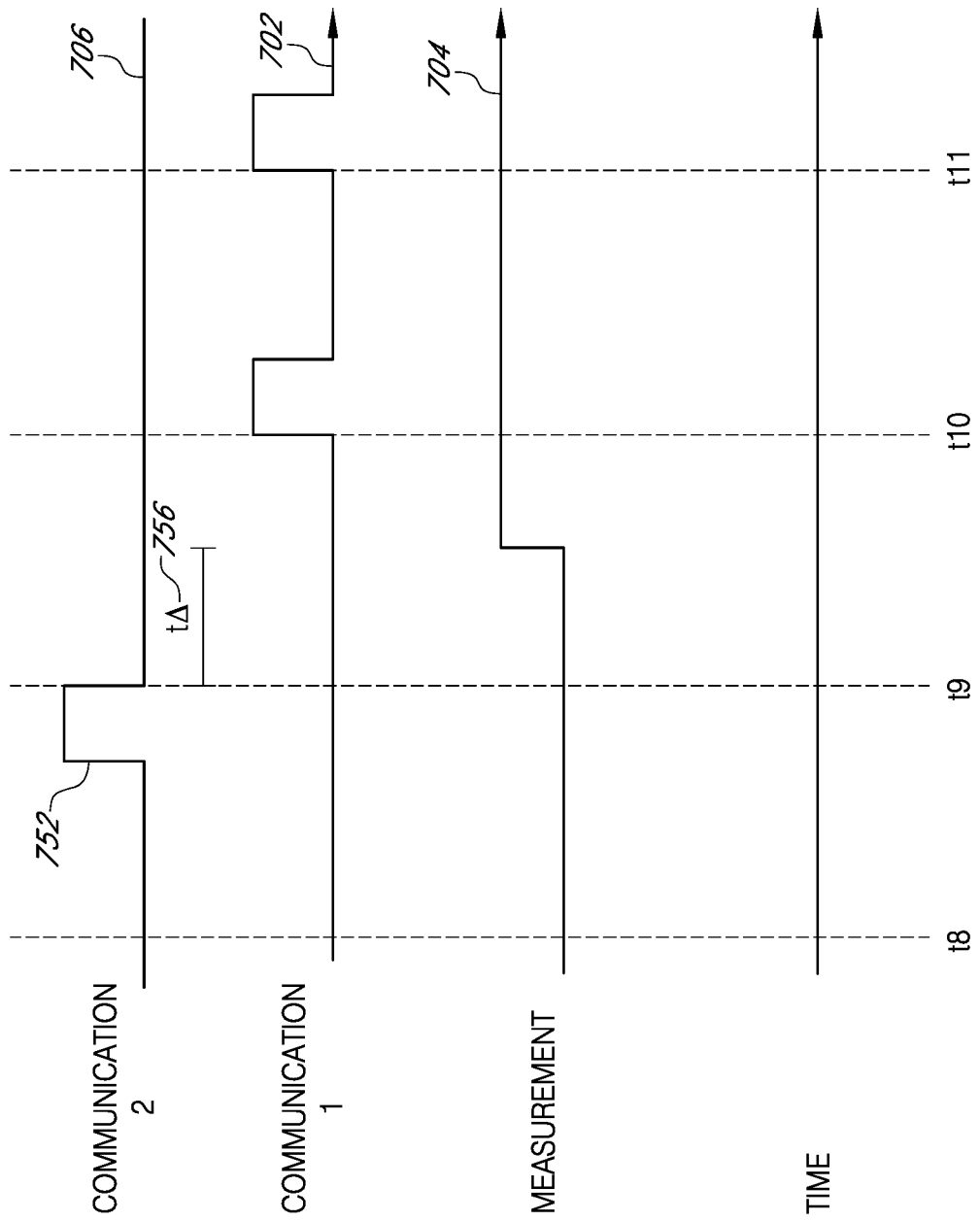
FIG. 7E illustrates an example timing diagram showing the timing of a transmission over a second communication protocol that starts a sensor session.

FIG. 7E illustrates an example timing diagram showing the timing of a transmission over a second communication protocol that starts a sensor session. In this illustrative example, Transmission 752 can utilize a second communication protocol, such as a communication protocol creating an RF field, including NFC or RFID, along Communication Line 706. The receipt of Transmission 752 can start measurements and communications along the first communication protocol along Communication Line 702. In some implementations, there can be a delay after Transmission 752 before measurements and communications along the first communication protocol start. This can be Time Delay 756, which can be a predetermined delay (e.g., 5, 4, 3, 2, 1, or less than 1 second) set by a user or automatically by Sensor Electronics Unit 6 and/or Display Device 20. After Time Delay 756, measurements on Measurement Line 704 can turn on.

D. Pairing Using Multiple Communication Protocols

In some implementations, one communication protocol can be used to initiate a pairing using another communication protocol. Such pairing can be performed as part of Action 615 and/or as a separate action. As was mentioned in this disclosure, a pairing action (e.g., Action 615 and/or other pairing action described in this disclosure) can be performed by Pairing Unit 655 and in combination with other actions, such as one or more of Actions 613. These actions can be performed in a queue, such as Action Queue 630. Such pairing ability can be advantageous in improving user experience. For example, and without limitation, some communication protocols have extensive pairing and/or authentication procedures. As a non-limiting example, radio transmission such as BLUETOOTH® can utilize a handshaking procedure where a device (e.g., Display Device 20) sends authentication information and is selected from a list of available devices. Having procedures with too many steps can detract from the user experience and also drain battery life and bandwidth with excessive communications.

By way of background, and as a non-limiting example, where Display Device 20 can have a unique address, such as a unique 48-bit address which can be represented as a 12-digit hexadecimal value. The address, or a portion of the address, can be used as an identifier for other devices with the same radio transmission, such as BLUETOOTH®, where those other devices also can also have an address for connection for communication. BLUETOOTH® devices can also have user-friendly names given to them to be seen in a display.

In this background example, for BLUETOOTH® and substantially similar radio transmission protocols, the connection process using BLUETOOTH® can have multiple steps. The first step can be an inquiry, where two BLUETOOTH® devices (e.g., a first device and second device by way of illustration) connecting for the first time run an inquiry to discover the other. The first device can send out a request, and the second device responds to the request with its address and possibly other information (e.g., its user friendly name or any desired information). The inquiry request can include the address of the first device, or the address information can be sent in a separate transmission. The next step is a paging process where the devices use the addresses obtained in the inquiry step to form a connection. The next step is the connection step, where the devices actually connect.

In some cases, during an initial connection, the two devices can be paired using an authentication process where a user validates the connection between the first and second devices. The flow of the authentication can vary, depending on the user interfaces of the devices. Sometimes pairing can be the click of the button, the entering of a numeric code, entering a common pin, entering an alphanumeric string, etc.

Because the BLUETOOTH® pairing process takes so many steps, and may prompt a user to enter information or take other actions, it can take away from the user experience. There is a need to simplify this procedure for the pairing CGM devices so that users can more easily monitor their glucose levels on their devices. Also, Sensor Electronics Unit 6 may not have user interfaces, which can make user initiated pairing over some communication protocols, such as radio transmission (e.g., BLUETOOTH®), more challenging. In many cases, with communication protocols such as BLUETOOTH®, a user may initiate and/or confirm pairings using a user interface of Display Device 20. With an RF field such as NFC or RFID, a user may just place Display Device substantially next to the Sensor Electronics Unit 6. This ability of NFC or RFID may be advantageous when Sensor Electronics Unit 6 does not have a user interface.

FIG. 8 illustrates an example flow chart showing how one communication protocol can be used to facilitate pairing for communication using another communication protocol. Process 800 can be performed by Sensor Electronics Unit 6 and/or Display Device 20 used with a CGM system.

In Block 802, a first device (e.g., Sensor Electronics Unit 6 or Display Device 20) can send an address, pairing information (e.g., timing information, encryption key, authentication information, advertising parameters, address, make/model, name, GAP, IRK, etc.), commands, and/or other information to a second device (e.g., Sensor Electronics Unit 6 or Display Device 20) using a second communication protocol. In some cases, the second communication protocol can utilize an RF field, such as NFC or RFID. In particular, NFC or RFID may be advantageous because they can transmit data and/or information automatically, sometimes in seconds or fractions of a second. When in range, the address, pairing, and/or other information can be sent from the device to another device. Advantageously, the limited range of NFC communication, in particular, can allow added security because only devices within its range can communicate via NFC. In some cases, NFC communications can be encrypted, such as using algorithms such as 128-bit or 256-bit keys and/or other encryption algorithms complying with standards such as the Advanced Encryption Standard ("AES"), RSA, Data Encryption Standard ("DES"), Triple DES, and the like.

In some implementations Block 802 can include sending encryption information. For example, and without limitation, encryption can be an encryption associated with a first communication protocol (e.g., BLUETOOTH® encryption) or other encryption schemes, such as, without limitation, using algorithms such as 128-bit or 256-bit keys and/or other encryption algorithms complying with standards such as the AES, RSA, DES, Triple DES, and the like.

In some implementations, Block 802 can include sending parameters, which can include frequency of advertising, the sequence of advertising (e.g., which devices are advertised to in what order and with what signals), type of Display Device 20 to be paired, and/or other pairing information. Advantageously, this can facilitate the pairing of Display Device 20 and Sensor Electronics Unit 6, and allow battery management wherein excessive advertising can be reduced.

Similarly, in Block 804, the second device can receive address, pairing, commands, and/or other information from the first device using the second protocol. The pairing information can include timing information, encryption key, authentication information, advertising parameters, address, make/model, name, GAP, IRK, and the like.

In Block 806, the first device can then pair with the second device for communication over the first communication protocol, which in some implementations can be a radio transmission such as BLUETOOTH®.

By way of illustrative example, Process 800 can be part of a tap-to-initiate NFC protocol where a user with Display Device 20 can connect Display Device 20 to Sensor Electronics Unit 6 of a CGM system by tapping (or bringing in substantially close proximity) Display Device 20 to Sensor Electronics Unit 6. This tap can use an RF field protocol, such as NFC or RFID, as the second communication protocol. This second communication protocol can then facilitate Display Device 20 and Sensor Electronics Unit 6 to pair to communicate using a first communication protocol, such as BLUETOOTH®.

In some cases, Process 800 (which can be called out-of-band pairing) can be used to conserve power over conventional pairing of the first communication protocol. For example, and without limitation, the advertising and connecting of Display Device 20 to Sensor Electronics Unit 6 using radio transmission such as BLUETOOTH® can drain the battery life of Sensor Electronics Unit 6. In some cases, Sensor Electronics Unit 6 can advertise using radio transmission such as BLUETOOTH® for different lengths of time depending on the type Display Device 20 attempting to connect. As non-limiting example, the advertising and connecting time using BLUETOOTH® for a specialized receiver can be shorter (e.g., about 7 seconds) as compared to the advertising and connecting time (e.g., 20 seconds) for a mobile device. As a consequence, energy savings can occur when NFC or RFID is used to pair because of the shorter connecting time.

By way of illustrative example, instead of the advertising and connecting time and power consumption associated with the radio transmission (e.g., BLUETOOTH®), NFC or can be used to initiate the pairing for the radio transmission. If used in a tap-to-initiate fashion, connecting Display Device 20 can establish a connection on demand without incurring (and/or using less than) the power consumption associated with standard radio transmission advertising and connecting.

E. Setting the White List and/or Bonding List

In some implementations, actions can be taken over a communication protocol to set and/or manipulate the white list and/or bonding list of Sensor Electronics Unit 6. In cases where NFC is used, these actions can include Action 618 and/or similar actions, where some actions can utilize Set White/Bonding List Unit 658. The following illustrative examples described in reference to white lists and bond lists can be part of Action 618 and/or separate actions, and/or utilize Set White/Bonding List Unit 658. As was mentioned in this disclosure, a setting white/bonding list action (e.g., Action 618 and/or other actions described in this disclosure setting, adding to, removing from, and/or manipulating a white list and/or bonding list) can be performed in combination with other actions, such as one or more of Actions 613. These actions can be performed in a queue, such as Action Queue 630.

Figure 9A:
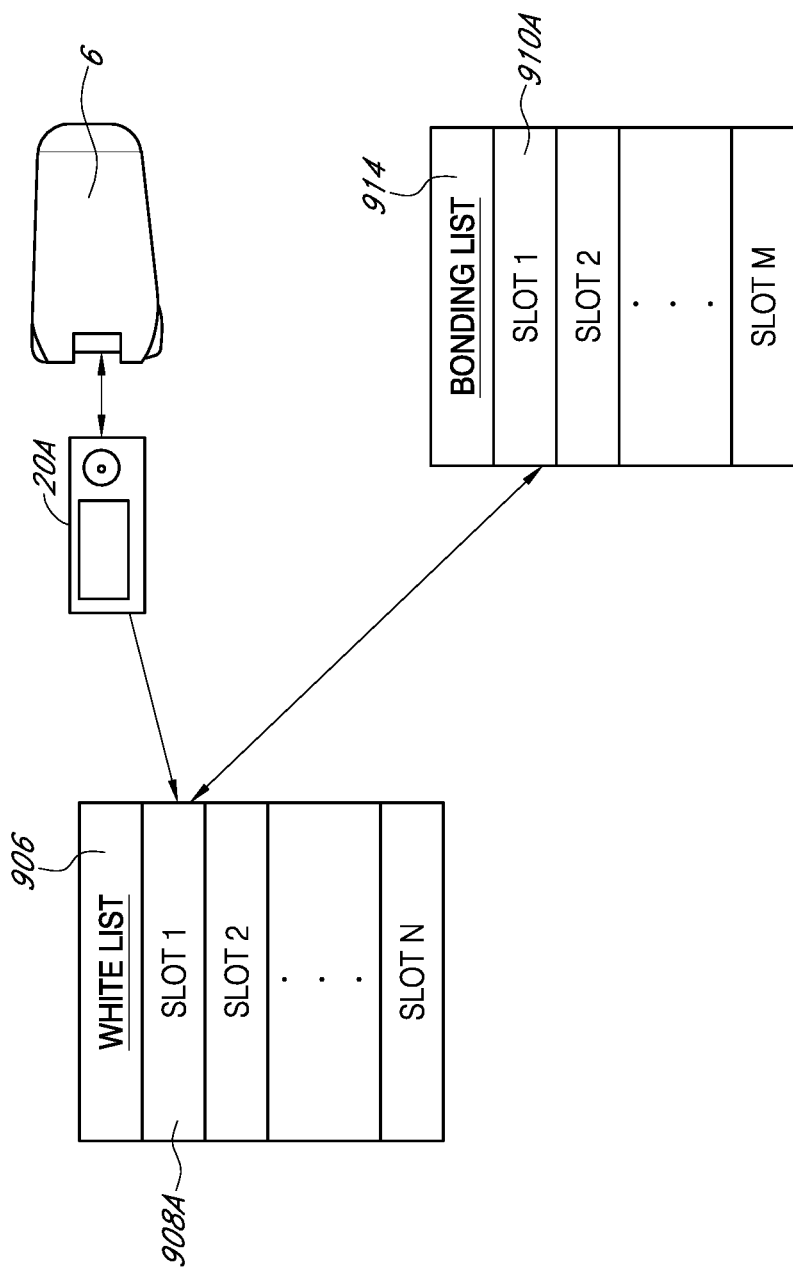
FIG. 9A illustrates an example white list and example bonding list that can be used for pairing an example sensor electronics units and an example display devices by using two or more communication protocols.

FIG. 9A-F illustrates example manipulations of white lists and/or bonding lists using a plurality of communication protocols. FIG. 9A illustrates an example White List 906 and Bonding List 914 that can be used for pairing Sensor Electronics Unit 6 and Display Device 20A by using two or more communication protocols. Sensor Electronics Unit 6 can communicate with Display Device 20A as described in Process 800. As described in Process 800, a second communication protocol can be used to allow Sensor Electronics Unit 6 and Display Device 20A to send/received address, pairing, and/or other information from each other. As a result of the exchange, Sensor Electronics Unit 6 and Display Device 20A can communicate using a first communication protocol, such as, without limitation, a first communication protocol using radio transmission such as BLUETOOTH®.

For the radio transmission (e.g., BLUETOOTH®) connection, Display Device 20A can be listed on White List 906 of Sensor Electronics Unit 6 when it is paired with Sensor Electronics Unit 6. White List 906 can have a predetermined number of slots, such as Slot 908A, where the pairing information from Display Device 20A can be saved into that slot. The information from White List 906 can also be stored on Bonding List 914. For example, and without limitation, the information for Display Device 20A stored in Slot 908A of White List 906 can also be stored in Slot 910A of Bonding List 914.

Figure 9B:
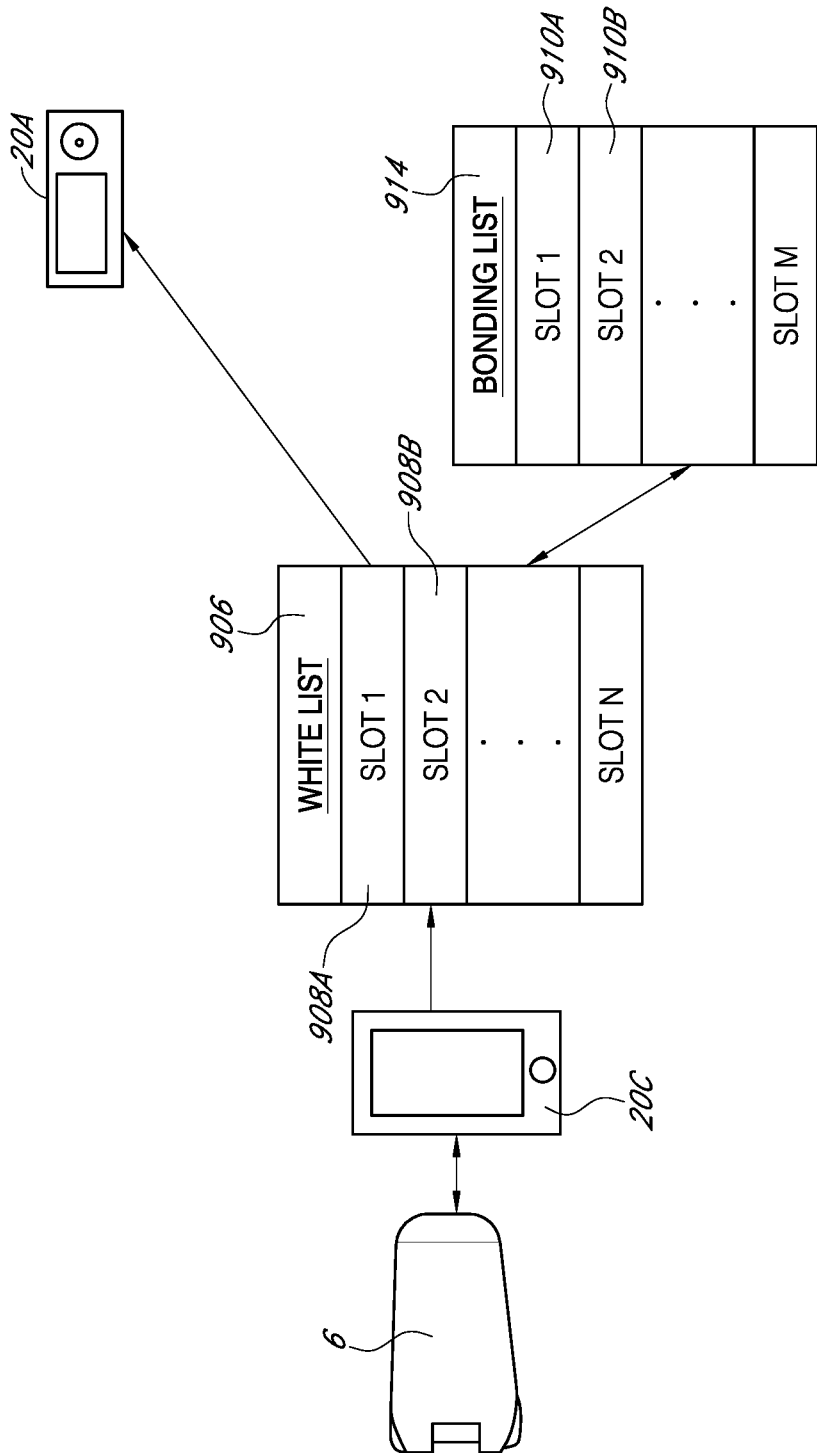
FIG. 9B illustrates multiple example display devices connecting to an example sensor electronics unit using a second communication protocol as reflected in the example white list and example bonding list illustrated in FIG. 9A.

FIG. 9B illustrates multiple example Display Devices 20A,C connecting using a second communication protocol as reflected in White List 906 and Bonding List 914 illustrated in FIG. 9A. For the radio transmission (e.g., BLUETOOTH®) connection, Display Device 20C can also be listed on White List 906 of Sensor Electronics Unit 6. The pairing information (e.g., address, make/model, name, GAP, IRK, etc.) for Display Device 20C can be stored in a different slot, such as Slot 908B, from the pairing information for Display Device 20A, which was stored in Slot 908A. The pairing information for Display Device 20C can also be stored in a slot in Bonding List 914, such as Slot 910B.

Figure 9C:
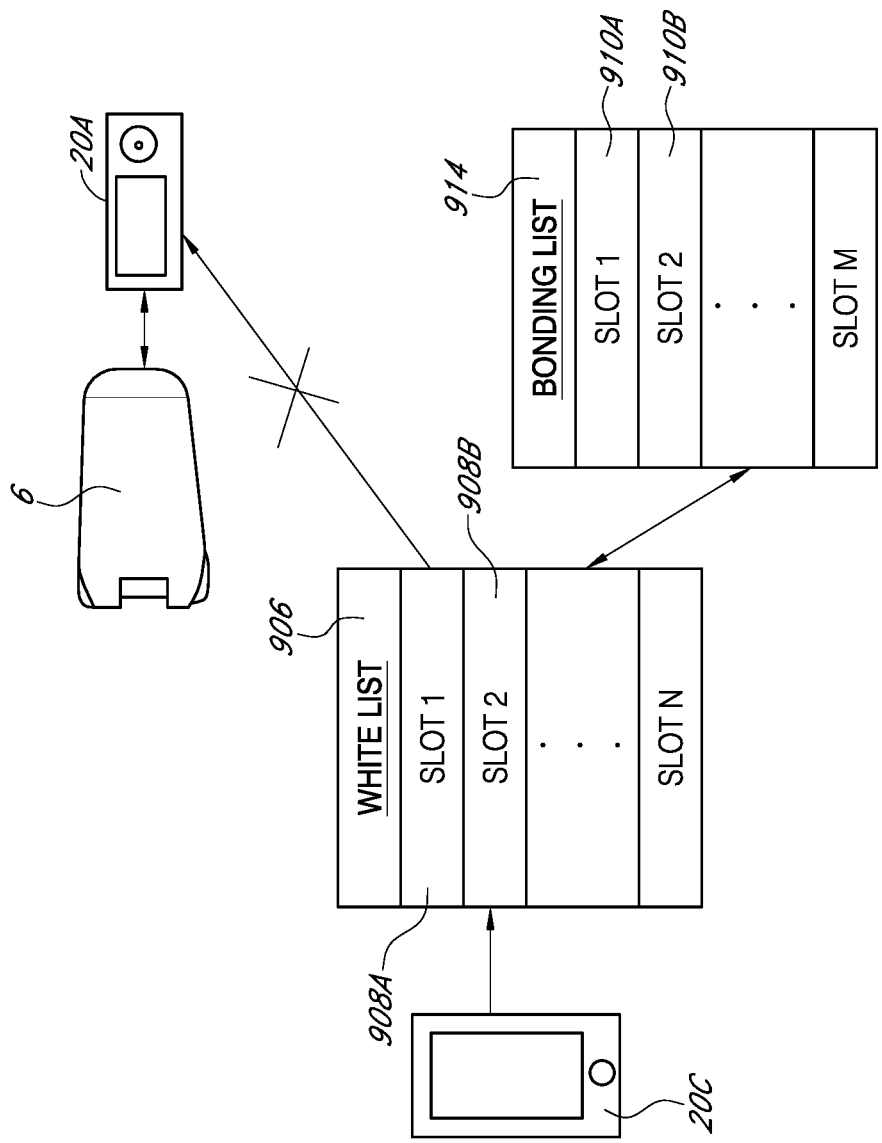
FIG. 9C illustrates an example white list and example bonding list of a communication protocol being updated when an example sensor electronics unit and an example display device are unpaired using the second communication protocol.

FIG. 9C illustrates an example white list and bonding list being updated when Sensor Electronics Unit 6 and Display Device 20A are unpaired using the second communication protocol. Advantageously, using a second communication protocol, such as an RF field (e.g., NFC or RFID), can allow a user to remove Display Device 20A (or any other display device, such as Display Device 20C) from a white list (e.g., White List 906) dynamically and on-demand. This can result in power savings in some situations. By way of illustrative example, Sensor Electronics Unit 6 can advertise to a display device on White List 906. However, if that display device is no longer in range and/or no longer desirable for use, Sensor Electronics Unit 6 potentially wastes energy undesirably in trying to make that connection. Also, advantageously, removing a first display device from White List 906 can prevent that first display device from inadvertently connecting if such connection would be undesirable. For example, and without limitation, a user may want to connect a second display device to Sensor Electronics Unit 6, and having the first display device connect to Sensor Electronics Unit 6 may prevent the second display device from connecting by taking its position in White List 906.

By way of example illustration, and without limitation, Sensor Electronics Unit 6 can use the second communication protocol, as also described with reference to FIGS. 9A-B, to remove Display Device 20A from White List 906, and consequently, from active communication with Sensor Electronics Unit 6. In some implementations, Display Device 20A can send a command to Sensor Electronics Unit 6 telling Sensor Electronics Unit 6 to remove Display Device 20A from Slot 908A. In some cases, this can leave an empty spot in White List 906.

Bonding List 914 may act independently from White List 906. Just because Display Device 20A was removed from White List 906 does not mean it will be removed from Bonding List 914. Bonding List 914 can store Display Device 20A's pairing information for later use. In some cases, where Bonding List 914 has utilized all its open slots, pairing information in one or more slots of Bonding List 914 may be deleted. Bonding List 914 can be stored in an application (e.g., a mobile application downloaded from an entity that created and/or owns and/or licenses the app, and/or an app store such as from APPLE, INC. or GOOGLE INC., or other) on one or more of Sensor Electronics Unit 6 and Display Devices 20A,C. In some cases, this deletion can be accomplished by Display Device 20A sending over the second communication protocol at least a command/request to remove Display Device 20A's pairing information from Bonding List 914. This removal can be desirable where a user does not want Sensor Electronics Unit 6 to communicate with Display Device 20A anymore, and does not want to risk Display Device 20A connecting. Removing Display Device 20A from Bonding List 914 advantageously reduces that risk of undesired communication/connection by removing the pairing information from memory.

Figure 9D:
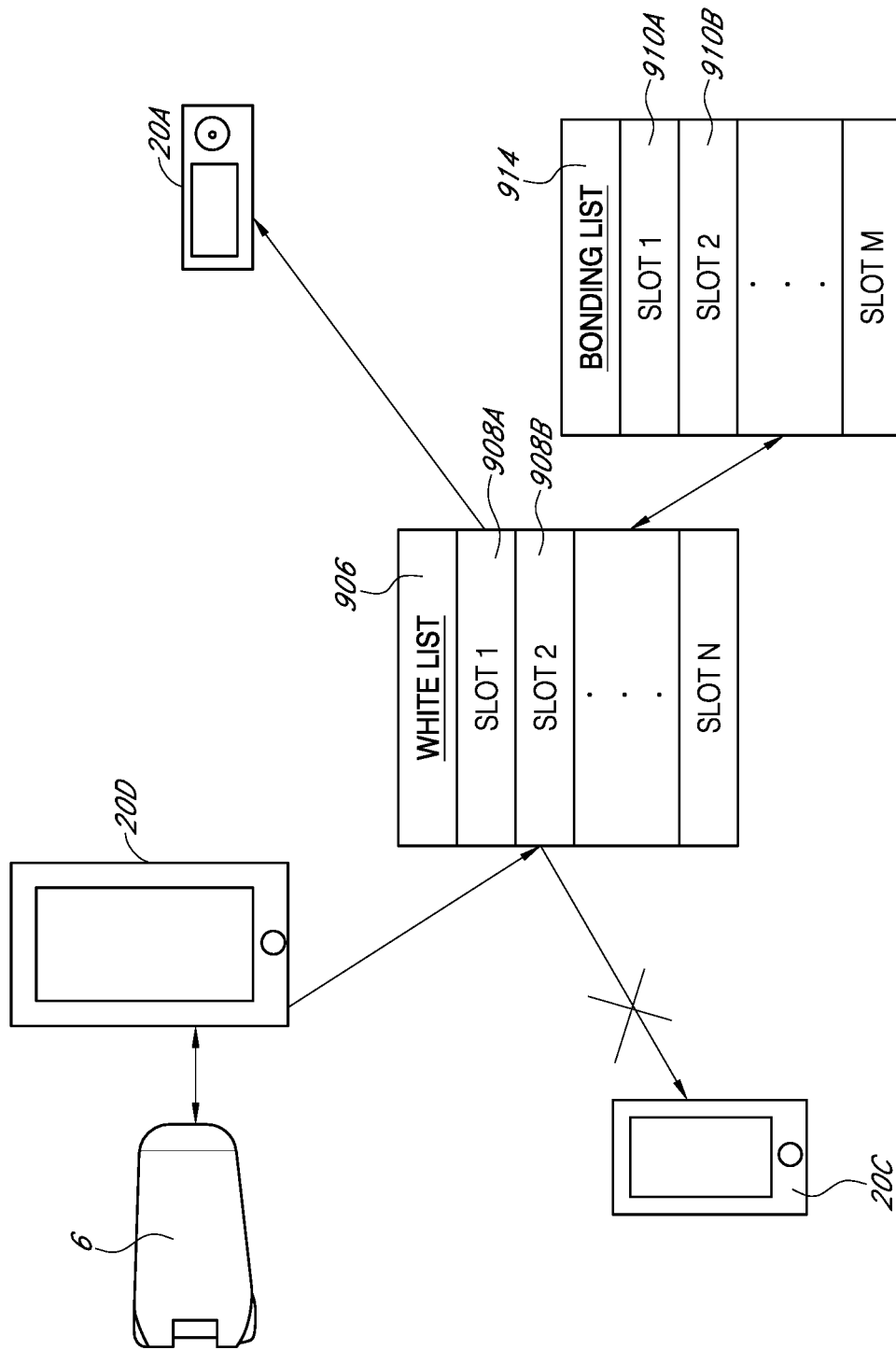
FIG. 9D illustrates an example implementation where a communication protocol can be used to add an example display device to the example white list of another communication protocol, and remove a different example display device from that same example white list.

FIG. 9D illustrates an example where a second communication protocol can be used to add Display Device 20D to White List 906 of a first communication protocol, and remove Display Device 20C from that same White List 906. Initially, pairing information for Display Device 20A can be stored in Slot 908A and pairing information for Display Device 20C can be stored in Slot 908B, and Display Device 20C and Sensor Electronics Unit 6 can be paired for communication using the second communication protocol. Display Device 20D can pair with Sensor Electronics Unit 6 to communicate over the first communication protocol by using a second communication protocol, such as a communication protocol using an RF field (e.g., NFC or RFID) as described in Process 800. In some cases, the pairing of Display Device 20D to Sensor Electronics Unit 6 can cause Display Device 20D to replace another display device paired to Sensor Electronics Unit 6. This can be desirable when all slots in White List 906 are filled and/or the user desires to pair Display Device 20D to Sensor Electronics Unit 6. In some implementations, Display Device 20D can also send a command via the second communication protocol to Sensor Electronics Unit 6 instructing Sensor Electronics Unit 6 to replace the pairing information of Display Device 20C on White List 906 with pairing information for Display Device 20D. In some implementations, the command can include instructions that causes the Sensor Electronics Unit 6 to add Display Device 20D to White List 906. In some cases, based at least in part on the type of Display Device 20D (e.g., receiver, mobile device, etc.), Sensor Electronics Unit 6 can replace a display device on White List 906 of the same device type. In some implementations, the command may include instructions that may cause the Sensor Electronics Unit 6 to send Display Device 20D information indicative of at least the contents of White list 906, including Slot 908B. Sensor Electronics Unit 6 can then send such information indicative of White List 906's contents to Display Device 20D. Display Device 20D can then, through user input or automatically (e.g., based on device type or learned pattern, such as a user disconnecting a device at certain times of day), choose to remove the pairing information of Display Device 20C from Slot 908B and add the pairing information of Display Device 20D. As illustrated in FIG. 9D, pairing information for Display Device 20D can replace pairing information for Display Device 20C in Slot 908B.

Figure 9E:
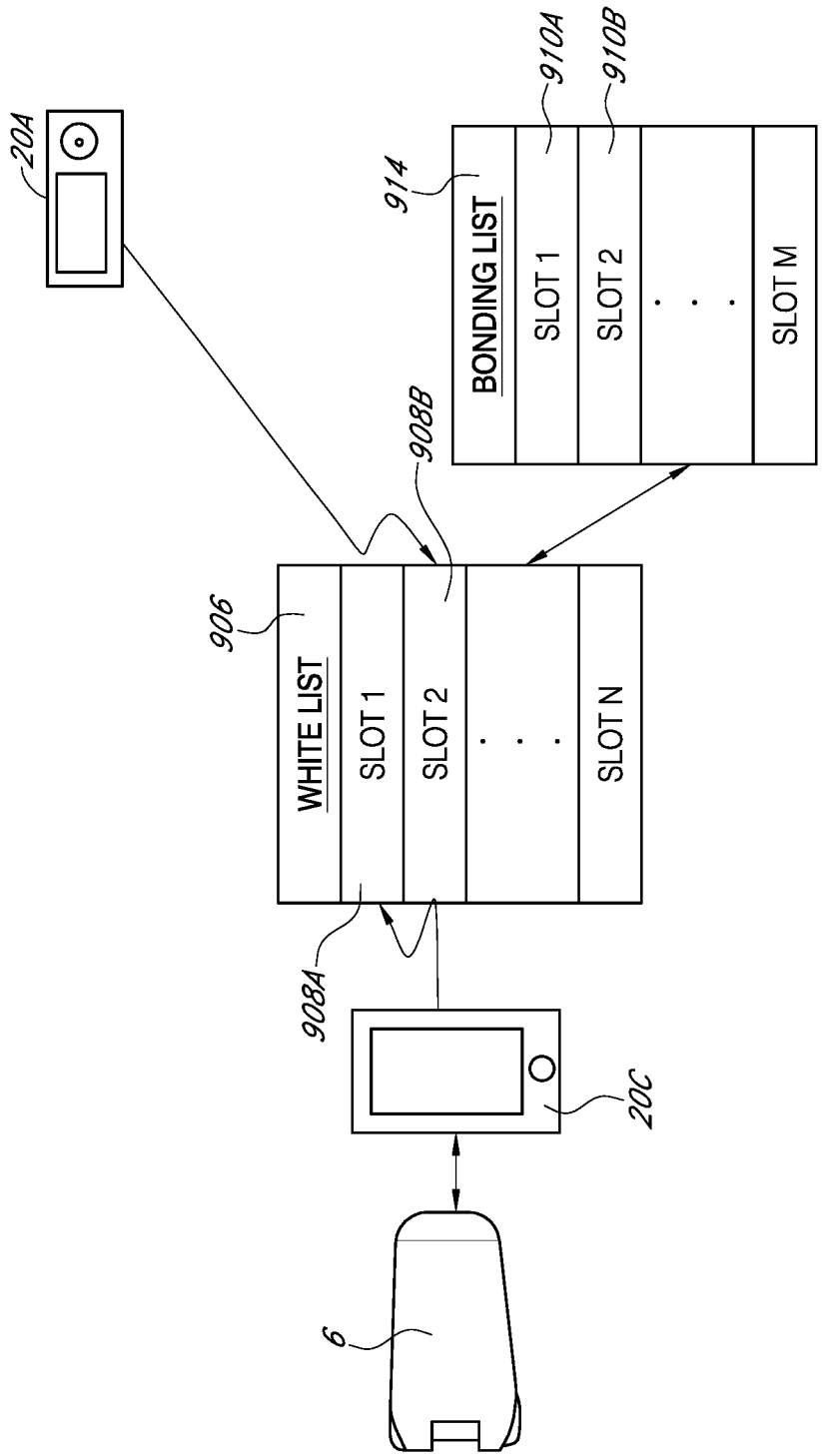
FIG. 9E illustrates an example where a second communication protocol is used to reorder the example white list illustrated in FIG. 9B.

FIG. 9E illustrates an example where the second communication protocol is used to reorder White List 906 illustrated in FIG. 9B. In some implementations, Sensor Electronics Unit 6 can communicate to paired display devices, (e.g., any paired Display Devices 20A-N), serially. In other words, it can communicate to one display device first and then sequentially to the next display device.

Figure 9F:
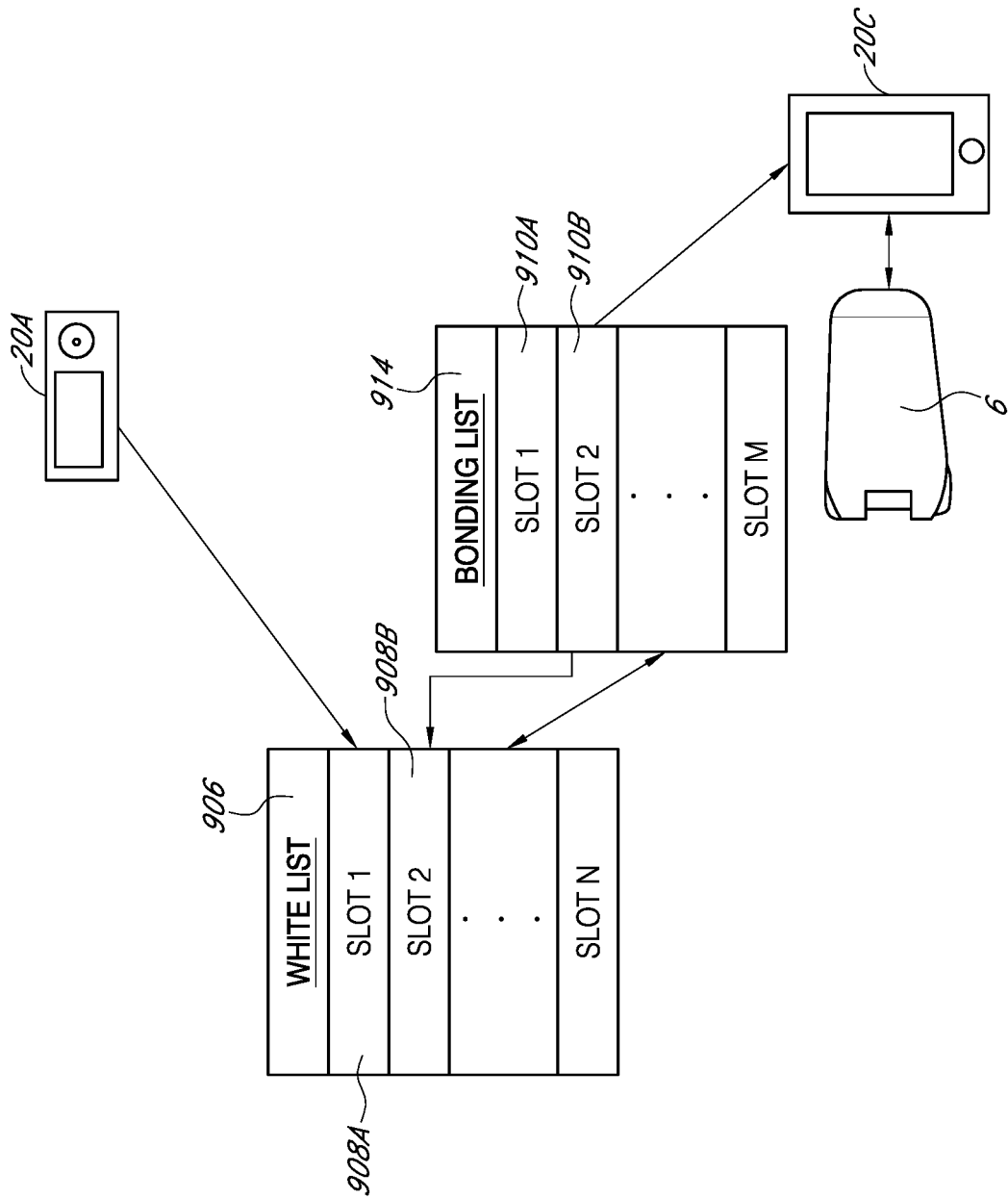
FIG. 9F illustrates an example where a second communication protocol is used to move an example display device on the example bonding list of a first communication protocol to the example white list of that first communication protocol.
Figure 9G:
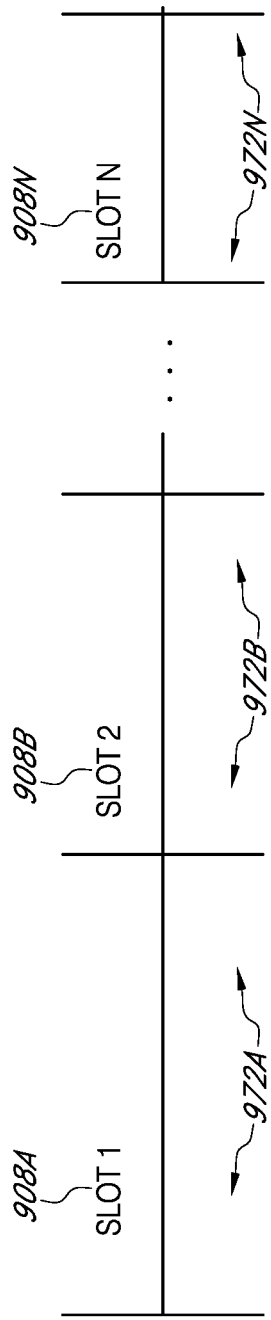
FIG. 9G illustrates a graph of example sequential communication windows for communication between an example sensor electronics unit and an example display devices in the example white list of FIGS. 9A-F.

By way of illustrative example, FIG. 9G illustrates sequential communication windows for communication between Sensor Electronics Unit 6 and display devices in Slots 908A-N. Communications between Sensor Electronics Unit 6 and display devices in Slots 908A-N can occur in Communication Windows 972A-N. Communication Windows 972A-N can each be a period of time where Sensor Electronics Unit 6 can connect to the respective display devices in Slots 908A-N and communicate with those display devices. Each Communication Windows 972A-N can be set (e.g., by a user or automatically by Sensor Electronics Unit 6) independently or together. For example, the period of time for each of Communication Windows 972A-N can be set independently in some cases. In other cases, a plurality of Communication Windows 972A-N can be set as the same period of time. In other cases, all of Communication Windows 972A-N can be set as the same period of time. In any of these cases, the period of time can be 5, 10, 15, 20, 25, 30, or more seconds. The period of time can also be set based at least in part on the time it takes to connect to a display device, the importance of the connection, and/or other factors. For example, the time it takes to connect to a display device can vary by device type and the communication protocol used. By way of illustration, a specialized receiver can be specifically configured to connect to Sensor Electronics Unit 6 and can send/receive pairing information faster than a generalized device, such as a mobile device. Accordingly, the specialized receiver may be in one of Communication Windows 972A-N that has been set with a smaller period of time. In some cases, the period of time for one of Communication Windows 972A-N that corresponds with a preferred device can be longer because a longer period of time can allow for more communication attempts in case there are any dropped and/or missed communications.

Because Sensor Electronics Unit 6 can communicate sequentially to the display devices in Slots 908A-N (e.g., where Sensor Electronics Unit 6 first communications to the display device in Slot 908A, then to the display device in Slot 908B, and so on and so forth), there can be a temporal difference between when display devices in Slots 908A-N receive messages. There can also be reliability differences (and/or robustness differences) between communications between Sensor Electronics Unit 6 and the display devices in each of Slots 908A-N. In some cases, the display device in Slot 908A that receives information first can be designated the primary display device, the display device in Slot 908B can be the secondary display device, the display device in Slot 908C can be the tertiary display device, and so on and so forth. In some cases, it may be desirable to switch the order of which display device is in which of Slots 908A-N. As an illustrative example, and without limitation, it may be desirable to switch the secondary display device to the primary display device, and consequently the display device in Slot 908B to Slot 908A.

In some cases, one or more of Display Devices 20A-N can communicate with Sensor Electronics Unit 6 to change the designation of one or more Display Devices 20A-N. Returning to FIG. 9E, by way of non-limiting example, and without limitation, the pairing information for Display Device 20C can be initially stored in Slot 908B and the pairing information for Display Device 20A can initially be stored in Slot 908A. Display Device 20C can communicate with Sensor Electronics Unit 6 using a second communication protocol, such as a communication protocol using an RF field, such as NFC or RFID. Through the second communication protocol, Display Device 20C can send a command to Sensor Electronics Unit 6 to move it to Slot 908A and move the pairing information in Slot 908A (e.g., the pairing information of Display Device 20A) to another slot, such as Slot 908B. In some implementations, the command can comprise a request to designate Display Device 20C to a particular status (e.g., primary, secondary, tertiary, etc.). Accordingly, Sensor Electronics Unit 6 can then switch Display Device 20C from Slot 908B to Slot 908A, and Display Device 20A from Slot 908A to Slot 908B based at least in part on the determination of Sensor Electronics Unit 6 that Slot 908A corresponds to the requested particular status. In making that switch, Sensor Electronics Unit 6 can also switch Display Device 20A to Slot 908B based at least in part on a determination that because Display Device 20C is switching to Slot 908A, Display Device 20A should switch to Slot 908B to provide for the appropriate priority. In some implementations, the command can comprise an interrogatory asking Sensor Electronics Unit 6 to send Display Device 20C information indicative of at least the contents of White List 906, including Slot 908B. Sensor Electronics Unit 6 can then send such information indicative of White List 906's contents to Display Device 20C. Display Device 20C can then, through user input or automatically (e.g., based on device type or learned pattern, such as a user's usage of a display device as the primary display device at certain times of day), choose to switch the pairing information in Slot 908B and Slot 908A.

In some implementations, the command to reorder White List 906 can be paired with another command, request, and/or action in this disclosure. For example, and without limitation, a display device can be added to White List 906, and White List 906 can also be reordered. There may any number of combinations of actions, which can be performed in a queue such as Action Queue 630.

FIG. 9F illustrates using the second communication protocol to move Display Device 20C on the Bonding List 914 of a first communication protocol to White List 906 of that first communication protocol. For example, and without limitation, pairing information for Display Device 20C can be stored in Slot 910B of Bonding List 914. Pairing information for Display Device 20C may not be listed in White List 906.

Using a second communication protocol, such as a communication protocol using an RF field like NFC or RFID, Display Device 20C can send a command to Sensor Electronics Unit 6 to move it from Bonding List 914 to White List 906 (e.g., to Slot 908B) of the first communication protocol of Sensor Electronics Unit 6. That first communication protocol, in some cases, can be BLUETOOTH®. Moving Display Device 20C to White List 906 from Bonding List 914 can be used, in some cases, when there is a malfunction in White List 906 and information from Bonding List 914 can be used to populate White List 906. For example, and without limitation, White List 906 can malfunction and have data corruption and may have errors in trying to identify and pair with Display Device 20C. Identifying information and pairing information for Display Device 20C can be moved from Bonding List 914 to White List 906 in such circumstances to allow a user to connect Display Device 20C.

In FIGS. 9A-F, even though depictions of display devices (e.g., Display Devices 20A,C-D) and Sensor Electronics Unit 6 have form factors for illustrative purposes, a person having ordinary skill in the art should appreciate that any of those display devices and Sensor Electronics Unit 6 are representative of any sensor electronics unit and/or display device described in this disclosure.

F. Data Transfer

In some implementations, Sensor Electronics Unit 6 may communicate with a Display Device 20 using one communication protocol. However, another communication protocol can be used in certain situations. For example, in some implementations, a user may desire to connect Display Device 20 to Sensor Electronics Unit 6 to collect past data, or data generated for analysis of past events to which Sensor Electronics Unit 6 collected data. Such connection to collect past data can be performed at one time, or periodically as desired. For example, and without limitation, Display Device 20 can be in a mode where a user may not be able to see real-time glucose values, but can receive glucose alerts and alarms during a sensor session. The data can later be downloaded by a healthcare professional or any user who desires to see the data using another display device (e.g., one of Display Devices 20A-N). As another non-limiting example, a user may want to switch display devices (e.g., one of Display Devices 20A-N) from another display device (e.g., another one of Display Devices 20A-N) that had previously been used. With the newly connected display device, a user can download past data from Sensor Electronics Unit 6. In this case, the display device downloading past data may provide timing information to Sensor Electronics Unit 6 at least in part of the period of time in which the Sensor Electronics Unit 6 should send lost data. As another non-limiting example, Sensor Electronics Unit 6 may reduce and/or altogether stop transmitting to connect to Display Device 20 after a determined number of time/cycles. This can allow Sensor Electronics Unit 6 to save power, processor use, and/or other resources. As another non-limiting example, a user and/or healthcare provider may want to periodically download data, and consequently, may want to connect Display Device 20 to Sensor Electronics Unit 6 to collect past data.

In these examples, Display Device 20 (or any other one of Display Devices 20A-N) may typically send/receive data and/or otherwise send communications to/from Sensor Electronics Unit 6 using one communication protocol, such as a communication protocol using radio transmission like BLUETOOTH®. Display Device 20 can then receive past data over another communication protocol, such as an RF field like NFC and RFID. Display Device 20 can first send a command to Sensor Electronics Unit 6 over either the first communication protocol or the second communication protocol. Sensor Electronics Unit 6 can then send the data over the second communication protocol. For example, and without limitation, this data can be sent over a communication protocol using an RF field, such as NFC and RFID. The second communication protocol can also re-initiate communication over the first communication protocol in ways substantially similar to processes described in this disclosure, such as those described with reference to FIGS. 8, 9A-F.

In some implementations, NFC or RFID can be used to transmit command and/or requests from Display Device 20 to Sensor Electronics Unit 6. These commands and/or requests can include start transmission for a communication protocol (e.g., radio transmission such as BLUETOOTH®, or any other communication protocol described in this disclosure), pair with display device (e.g., radio transmission such as BLUETOOTH®, or any other communication protocol described in this disclosure), stop transmission for a communication protocol (e.g., radio transmission such as BLUETOOTH®, or any other communication protocol described in this disclosure), sleep, low power, wake-up, calibrate Sensor Electronics Unit 6 and/or Continuous Analyte Sensor 8, start or stop sensor session, send past data, and/or any command desirable, including those associated with one or more of Actions 613. In this way, in some cases, communication protocols utilizing RF fields, such as NFC or RFID, can be used to initiate transfer over data over radio transmission, such as BLUETOOTH®. This data can include, data indicative of estimated blood glucose levels, past data indicative of blood glucose levels, pairing information, statuses, model numbers, error logs, communication conditions (e.g., historical or previous communications such as the following: the number of previously missed communications; a previous advertising interval/duration budget; and/or historical time-until-connection associated with a particular display device), etc.

In some implementations, a second communication protocol can be used to transfer information regarding an error condition or any type of data that would be helpful in assisting with technical support when a first communication protocol is not working and/or is impaired in some form. For example, and without limitation, in some implementations, a radio transmission such as BLUETOOTH® can be the first communication protocol. In some cases, the radio transmission capabilities of Sensor Electronics Unit 6, Display Device 20, or both can be impaired or broken so that Sensor Electronics Unit 6, Display Device 20, or both do not have full communication capabilities over radio transmission. It may be desirable to get diagnostic and/or error condition information (e.g., an error log) in order to diagnose the problem. A second communication protocol using a RF field, such as NFC or RFID, can be used to obtain the diagnostic and/or error condition information. Using the second communication protocol can be advantageous in that it allows the diagnostic and/or error condition information to be pulled on demand instead of waiting for the communication timing of the first communication protocol, if the first communication protocol can even send that information. By way of illustrative example, Display Device 20 can send a command to Sensor Electronics Unit 6 over a communication protocol using an RF field, such as NFC or RFID. Sensor Electronics Unit 6 can then send the diagnostic and/or error condition information using that same communication protocol. In some cases, Display Device 20 can then further transfer this information to a server (e.g., a network, cloud, etc.) via a communication protocol, such as cellular connection, Wi-Fi or any communication protocol described in this disclosure.

In some cases, it can be desirable to receive data from Sensor Electronics Unit 6 when the battery of Sensor Electronics Unit 6 is low or dead. In some implementations, a communication protocol can be used to retrieve that data, such as, without limitation data indicative of estimated blood glucose levels, past data indicative of blood glucose levels, pairing information, statuses, model numbers, error logs, etc. For example, and without limitation, a communication protocol using an RF field, such as NFC or RFID, can use the energy of the Display Device 20 to power the transmission of Sensor Electronics Unit 6 over that same communication protocol. By way of illustrative example, where NFC is the communication protocol, Display Device 20 can create an RF field using induction. Sensor Electronics Unit 6 can have an NFC tag that stores data. Accordingly, the Display Device 20 can have an NFC reader that can read the NFC tag even when Sensor Electronics Unit 6 has little or no power. In some implementations, the use of a communication protocol by Display Device 20 can actually power Sensor Electronics Unit 6 unit to send data. By way of illustrative example, and without limitation, the magnetic inductance of the RF field created by Display Device 20 using an NFC communication protocol can allow for inductive charging, or the transfer of energy wirelessly from Display Device 20 to Sensor Electronics Unit 6. This energy can be used by Sensor Electronics Unit 6 to power data transfer using an RF field, such as NFC, or another communication protocol. In some implementations, this energy can be used by Sensor Electronics Unit 6 to power the circuitry (e.g., application-specific integrated circuit ("ASIC") and/or other hardware) of Sensor Electronics Unit 6 to recover data and/or this energy can be used to power a radio transmission protocol, such as BLUETOOTH®. The radio transmission protocol can then transmit data from Sensor Electronics Unit 6 to Display Device 20.

Advantageously, there can be situations where a user desires to retrieve such data from their Sensor Electronics Unit 6 after Sensor Electronics Unit 6 has low or no battery life. For example, and without limitation, a user could send his/her Sensor Electronics Unit 6 to a health provider or a third party of the end of a sensor session. At that stage, the battery of Sensor Electronics Unit 6 may be low or depleted. The health provider or third party could then download the data from Sensor Electronics Unit 6 using a communication protocol that uses an RF field, such as NFC or RFID. In some cases, the health provider can be prompted by Sensor Electronics Unit 6, where Sensor Electronics Unit 6 may prompt the display device of the health provider to transfer data over NFC.

As another non-limiting example, a user may wish to clone his/her Sensor Electronics Unit 6 (e.g., using Action 609 and/or Clone Unit 649). Advantageously, if the user transfers the data after Sensor Electronics Unit 6 is out of power or has low power (e.g., little to no battery life), he/she can transfer as much information as possible before switching to a new sensor electronics unit. Accordingly, while in using NFC and a clone action, such as Action 609, the user can then power the transfer of data/information from Sensor Electronics Unit 6 to Display Device 20 even if Sensor Electronics Unit 6 has little to no battery.

As another non-limiting example, a user may have been negligent in his/her monitoring of his/her blood glucose level and the maintenance of his/her equipment. If he/she desires to get information from his/her Sensor Electronics Unit 6 when it has little to no battery life, he/she can use NFC to power that transfer.

In some implementations, a plurality of communication protocols can be used where some types of communications are sent over one type of communication protocol and other types of communications are sent over another type of communication protocol.

By way of illustrative example, and without limitation, NFC can be used to send all commands and/or requests from a Display Device 20 to Sensor Electronics Unit 6. These commands and/or requests can include start transmission for a communication protocol (e.g., radio transmission such as BLUETOOTH®, or any other communication protocol described in this disclosure), pair with Display Device 20 (e.g., radio transmission such as BLUETOOTH®, or any other communication protocol described in this disclosure), stop transmission for a communication protocol (e.g., radio transmission such as BLUETOOTH®, or any other communication protocol described in this disclosure), calibrate Sensor Electronics Unit 6 with Continuous Analyte Sensor 8, send past data, and/or any command desirable, including those associated with one or more of Actions 613. NFC can also be used to configure settings of the Sensor Electronics Unit 6, such as its transmission parameters, advertising (e.g., broadcasting, beaconing, stealth mode, etc.), timings, etc. Advantageously, NFC can provide a secure and intuitive way for a user to send these commands and/or requests. The range limitation of NFC can lower the risk of unauthorized display devices sending commands and/or requests to Sensor Electronics Unit 6. Furthermore, the physical action of bringing the Display Device 20 close to Sensor Electronics Unit 6 can be intuitive for a user.

In some implementations, radio transmission such as BLUETOOTH® can be used to send all data from the Sensor Electronics Unit 6 to a Display Device 20 because radio transmission can have a longer range and higher transfer speed. Also, advantageously, radio transmission communication can happen autonomously with Display Device 20, and also can be utilized without a user actively placing a Display Device 20 next to Sensor Electronics Unit 6. In some cases, the data can be transmitted in response to commands and/or requests sent over a communication protocol using an RF field such as NFC or RFID. In some implementations, certain types of data can be sent over the RF field rather than radio transmission. By way of illustrative example, and without limitation, some data can be considered of higher security and could have an impact on the functionality of a Sensor Electronics Unit 6/Continuous Analyte Sensor 8. It may be desirable to use a different protocol than radio transmission to send such information. For example, and without limitation, a user can send calibration data from a Display Device 20 to Sensor Electronics Unit 6. This calibration data can contain data indicative of analyte measurements, such as blood glucose levels, taken from another source, such as finger pricking. The data can be used to calibrate the readings of blood glucose levels from the Sensor Electronics Unit 6/Continuous Analyte Sensor 8. Such data can be sent over NFC in order to provide added security and/or to make the transfer more user-friendly. Calibration data may also be particularly advantageous to send over NFC because it can allow a user to adjust or update the calibration of Sensor Electronics Unit 6 on demand when it is convenient and/or desirable.

In some implementations, transmissions can be split between a plurality of communication protocols in order to further encrypt a message. For example, and without limitation, part of a command can be sent from a Display Device 20 over a first communication protocol (e.g., radio transmission such as BLUETOOTH®) and part of the command can be sent over a second communication protocol (e.g., an RF field such as NFC or RFID). By way of illustrative example, in the cases where an RF field communication protocol and radio transmission are used, the Sensor Electronics Unit 6 can perform the commanded action if it receives the part of the command over radio transmission and the part of the command over an RF field communication protocol. Similarly, data transmitted from Sensor Electronics Unit 6 can be split between an RF field communication protocol and radio transmission so that part of the data is sent over the RF field communication protocol and part of the data is sent over radio transmission. In this way, a Display Device 20 would use both the RF field communication protocol and the radio transmission to receive all the data. As a non-limiting example, encryption information could be sent over an RF field communication protocol such as NFC or RFID, and then that encryption data could be used to decrypt data sent via a radio transmission protocol such as BLUETOOTH®.

In some implementations, what kinds of transmissions are sent over which communication protocol can be dependent at least in part on remaining battery life and/or available power of Sensor Electronics Unit 6. In some implementations, when there is battery life of Sensor Electronics Unit 6 is above a first predetermined threshold, one usage of communication protocols can be used, where as if the battery life falls below a second predetermined threshold (which may have a value equal or substantially equal to the first predetermined threshold or have a different value), a second usage of communication protocols can be used. By way of illustrative example, and without limitation, a first predetermined threshold can be defined in a range where the battery of Sensor Electronics Unit 6 has substantial life (e.g., above 30, 40, 50, 60, or more percentage of battery life remaining, or any predetermined percentage as desired). When the amount of battery life is above that first predetermined threshold, communications between the Sensor Electronics Unit 6 and Display Device 20 can utilize radio transmission such as BLUETOOTH® and/or a combination of radio transmission, such as BLUETOOTH®, and an RF field communication protocol, such as NFC or RFID. However, when the amount of battery life of the Sensor Electronics Unit 6 is relative low and falls below the second predetermine threshold (e.g., less than 30% of battery life remaining), a communication protocol that utilizes less energy and/or saves energy can be used (e.g., an RF field communication protocol, such as NFC or RFID) for communications between Sensor Electronics Unit 6 and Display Device 20. Advantageously, this can allow a user to ration battery power so that only a certain number of actions can be performed over a communication protocol per day. For example, if the number of actions (e.g., 1, 5, 10, or any number of actions budgeted by a user determined at least in part by the energy consumption) performed by a first communication protocol per day is exceeded, the communications between the Sensor Electronics Unit 6 and Display Device 20 can switch to a second communication protocol. By way of non-limiting example, the first communication protocol can be a radio transmission such a BLUETOOTH® and the second communication protocol can utilize an RF field, such as NFC or RFID. The number of actions could be 5 in a day. So if the user exceeded 5 communications over the radio transmission in a day, the user would then utilize the RF field communication protocol for subsequent communications.

In some implementations, a transmission can be sent over one communication protocol, but data/information over a second communication protocol can be used to view the transmission. For example, and without limitation, data can be sent from a Sensor Electronics Unit 6 to a Display Device 20 using a radio transmission protocol such as BLUETOOTH®. However, that data may not be viewable by the Display Device 20 until the Sensor Electronics Unit 6 sends a decryption key over an RF field communication protocol, such as NFC or RFID, to the Display Device 20.

By way of illustrative example, and without limitation, a Sensor Electronics Unit 6 may broadcast, beacon, and/or otherwise send data using one protocol. For example, it may send data over a radio transmission, such as BLUETOOTH®, to any device within its range. A second communication protocol, such as a communication protocol using an RF field like NFC or RFID can be used for a user to view that information. By way of illustration, and without limitation, a Sensor Electronics Unit 6 can broadcast data about a user over BLUETOOTH® to BLUETOOTH®-enabled devices within the Sensor Electronics Unit 6's BLUETOOTH® range. These BLUETOOTH®-enabled devices can receive the data and store the data (e.g., using a computer application). However, the data can be encrypted and/or otherwise not viewable on the BLUETOOTH®-enabled device until the BLUETOOTH®-enabled device uses NFC or RFID to communicate with the Sensor Electronics Unit 6 to receive an encryption key, a command, and/or data that enables the BLUETOOTH®-enabled device to view the received data.

As another illustrative example, in some implementations, the Sensor Electronics Unit 6 can be in broadcast mode using a first communication protocol using a radio transmission, such as BLUETOOTH®, wherein the radio of the Sensor Electronics Unit 6 can only send data, but cannot receive it from a Display Device 20 (e.g., one-way data transmission). In this case, a second communication protocol using an RF field, such as NFC or RFID, can be used to send commands, such as a command opening a two-way communication over the first communication protocol. Once two-way communications are open over the first communication protocol, the Display Device 20 can send commands and/or information to the Sensor Electronics Unit 6. For example, and without limitation, the Display Device 20 can send calibration data and a calibration command over the first communication protocol to the Sensor Electronics Unit 6. Once the two-way communication is completed, then the Sensor Electronics Unit 6 goes back into broadcast mode. Advantageously, allowing the second communication protocol to open two-way communication while the Sensor Electronics Unit 6 is in broadcast mode can allow the Sensor Electronics Unit 6 to retain the efficiency of broadcasting via broadcast mode, yet still receive timely information and/or commands from a Display Device 20.

As another illustrative example, a Sensor Electronics Unit 6 may use a radio transmission broadcast, such as a BLUETOOTH® broadcast (e.g., beaconing and/or one-way communication), sent to Display Device 20. This beacon can be sent exclusively to certain devices (e.g., in an exclusive mode) and/or can be sent only at certain times. This exclusivity can be achieved by encrypting the beacon and/or broadcasting the beacon to certain identified display devices (e.g., identified through make, model, IP address, etc. in the beacon). For example, and without limitation, a user may use different display devices at night than in the day. In the day, he/she may go to work in an office and have mobile devices that he/she uses there. These may be different display devices that he/she uses when he/she is at home. In some implementations, the beacon can broadcast to a first set of display devices during the day when the user is at work and to a second set of display devices at night when the user is away from work. In some cases, these radio transmission broadcasts can be encrypted to secure any data, commands, information, statuses, etc. sent between sensor electronics devices and display devices, and vice versa. In some implementations, another communication protocol, such as NFC or RFID can be used to transmit decryption keys to decrypt the encrypted data, commands, information, statuses, etc. Where NFC is used, a display device that a user desires to send/receive data, commands, information, statuses, etc. can be brought in close proximity to the Sensor Electronics Unit 6. The Sensor Electronics Unit 6 may be beaconing to the display device already, or may have yet-to-start beaconing. The display device and Sensor Electronics Unit 6 can exchange decryption keys (e.g., static keys and/or dynamic keys) which can then be used to decrypt transmissions (e.g., data, commands, information, statuses, communications, etc.) sent between the display device and Sensor Electronics Unit 6.

In some cases, a Sensor Electronics Unit 6 can beacon, where it can send data and/or invite devices within its communication range to connect. In some implementations, a Sensor Electronics Unit 6 can beacon using a first communication protocol and then a Display Device 20 can use a second communication protocol to connect the Display Device 20 to the Sensor Electronics Unit 6 for communication using the first communication protocol. By way of illustrative example, and without limitation, a Sensor Electronics Unit 6 can beacon using a radio transmission such as BLUETOOTH®. A Display Device 20 can receive a beaconed message and be prompted to pair with the Display Device 20. The Display Device 20 can then use an RF field communication protocol such as NFC or RFID to pair the Sensor Electronics Unit 6 and Display Device 20 for communication over BLUETOOTH®. Advantageously, such a pairing mechanism can simplify pairing procedures and allow users to avoid the plurality of steps involved with BLUETOOTH® pairing. Also, it may also provide extra security by utilizing NFC's limited range for pairing, which may prevent unauthorized connections.

In some cases, poor connectivity over a first communication protocol, such as BLUETOOTH®, can result in too many tries to connect and dropped data packets. Being able to intelligently switch to another, second communication protocol that does not have the same connectivity issues can be used to resynchronize the timing of the first communication protocol and/or be used to send the data packets.

By way of illustrative example, a first communication protocol for communication between a Sensor Electronics Unit 6 and a Display Device 20 can be a radio transmission such as BLUETOOTH®. As desired by a user (e.g., when a user of Sensor Electronics Unit 6 and/or the Display Device 20 notice connectivity issues), connections (e.g., pairing) of the Sensor Electronics Unit 6 and the Display Device 20 can be re-established by using a second communication protocol, such as an RF field communication protocol (e.g., NFC or RFID).

Where radio transmission such as BLUETOOTH® is the first communication protocol and NFC is the second communication protocol, NFC can be particularly helpful in re-establishing connectivity because of NFC's simple initiation and transmission at short ranges. As an example, Display Device 20 can send a command to the Sensor Electronics Unit 6 to disconnect. An RF field communication protocol such as NFC or RFID can also be used by Sensor Electronics Unit 6 and/or Display Device 20 to exchange public and/or private keys for authentication and connection.

In some cases, an RF field communication protocol, such as NFC or RFID, can be used to send data from the Sensor Electronics Unit 6 to Display Device 20, or vice versa, in order to send missed data. For example, and without limitation, over the RF field communication protocol, the received data packets by either the Sensor Electronics Unit 6 or Display Device 20 can be compared with the sent data packets by the other of Sensor Electronics Unit 6 and Display Device 20. In some cases, the Sensor Electronics Unit 6 and/or Display Device 20 can have lists of sent, received, and/or sent but not received data packets. A processor of either the Sensor Electronics Unit 6 and/or the Display Device 20 can compare the sent and received lists, or process the sent but not received list, and determine which data packets were sent but not received. Those data packets that were sent but not received can be transferred accordingly (e.g., from Sensor Electronics Unit 6 to Display Device 20 and/or Display Device 20 to Sensor Electronics Unit 6) over the RF Field communication protocol, or any other communication protocol described in this disclosure (e.g., radio transmission such as BLUETOOTH®).

Exemplary Analyte Monitoring Systems

The following exemplary analyte monitoring systems are provided.

Analyte Monitoring System 1: An analyte monitoring system, comprising: a sensor configured to take measurements indicative of analyte levels; a sensor electronics unit communicatively coupled to the sensor, the sensor electronics unit configured to: receive the measurements indicative of analyte levels from the sensor and calculate estimated analyte values; operate in a normal power mode and a low power mode; transmit data indicative of analyte levels when in the normal power mode using a first communication protocol, and receive a command in the low power mode using a second communication protocol; and a display device configured to: transmit the command to the sensor electronics unit using the second communication protocol; receive data indicative of analyte levels from the sensor electronics unit using the first communication protocol; and wherein the sensor electronics unit is configured to switch from the low power mode to the normal power mode in response to the command and wirelessly connect to the display device for communication using the first communication protocol.

Analyte Monitoring System 2: An embodiment of Analyte Monitoring System 1, wherein the low power mode is a shelf mode.

Analyte Monitoring System 3: An embodiment of Analyte Monitoring System 1 or 2, wherein the command is a wake up command.

Analyte Monitoring System 4: An analyte monitoring system, comprising: a sensor configured to take measurements indicative of analyte levels; a sensor electronics unit communicatively coupled to the sensor, the sensor electronics unit configured to: receive the measurements indicative of analyte levels from the sensor and calculate estimated analyte values, operate in a normal power mode and a low power mode, transmit data indicative of analyte levels when in the normal power mode using a first communication protocol, and receive a command in the normal power mode using a second communication protocol; and a display device configured to: receive data indicative of analyte levels from the sensor electronics unit using the first communication protocol, and transmit the command to the sensor electronics unit using the second communication protocol; and wherein the system is configured to cause the sensor electronics unit to switch from the normal power mode to the low power mode in response to the command and wirelessly disconnect the display device from the sensor electronics unit for communication over the first communication protocol.

Analyte Monitoring System 5: An embodiment of Analyte Monitoring System 4, wherein the low power mode is a shelf mode.

Analyte Monitoring System 6: An embodiment of Analyte Monitoring System 4 or 5, wherein the command is a sleep command.

Analyte Monitoring System 7: An analyte monitoring system, comprising: a sensor configured to take measurements indicative of analyte levels; a sensor electronics unit communicatively coupled to the sensor and configured to: receive the measurements indicative of analyte levels, process the received measurements, and transmit data indicative of analyte levels using a first communication protocol at a predefined time; and a display device configured to: receive data indicative of analyte levels sent by the sensor electronics unit using the first communication protocol, and use a second communication protocol to retrieve data indicative of analyte levels from the sensor electronics unit at least before the predefined time.

Analyte Monitoring System 8: An embodiment of Analyte Monitoring System 7, wherein the processing of the received measurements by the sensor electronics unit comprises calculating estimated analyte levels based at least in part on the measurements.

Analyte Monitoring System 9: An analyte monitoring system, comprising: a sensor configured to take measurements indicative of analyte levels; a sensor electronics unit communicatively coupled to the sensor and configured to: receive the measurements indicative of analyte levels, process the received measurements, and transmit data indicative of analyte levels using a first communication protocol at a predefined time; and a display device configured to: receive data indicative of analyte levels sent by the sensor electronics unit using the first communication protocol, transmit a command message via a second communication protocol to stop the sensor from taking measurements, and further transmit a request message via the second communication protocol requesting the sensor electronics unit to stop the transmission of the data indicative of analyte levels using the first communication protocol.

Analyte Monitoring System 10: An embodiment of Analyte Monitoring System 9, wherein the processing of the received measurements by the sensor electronics unit comprises calculating estimated analyte values based at least in part on the measurements.

Analyte Monitoring System 11: An embodiment of Analyte Monitoring System 9 or 10, wherein the command message provides instructions to the sensor electronics unit to cause the sensor to stop taking measurements.

Analyte Monitoring System 12: An embodiment of Analyte Monitoring System 9, 10, or 11, wherein the display device is further configured to use the second communication protocol to initiate the taking of measurements by the sensor and initiate the transmission of data indicative of analyte levels using the first communication protocol.

Analyte Monitoring System 13: An analyte monitoring system, comprising: a sensor configured to take measurements indicative of analyte levels; a sensor electronics unit communicatively coupled to the sensor, wherein the sensor electronics unit is configured to: receive the measurements indicative of analyte levels from the sensor and calculate estimated analyte values, transmit data indicative of analyte levels using a first communication protocol, and receive commands using a second communication protocol; and a display device configured to: receive data indicative of analyte levels using the first communication protocol, and transmit a data request command to the sensor electronics unit using the second communication protocol, wherein the sensor electronics unit sends data indicative of analyte levels using the first communication protocol in response to the data request command.

Analyte Monitoring System 14: An embodiment of Analyte Monitoring System 13, wherein the sensor electronics unit is further configured to measure a remaining battery life of the sensor electronics unit.

Analyte Monitoring System 15: An embodiment of Analyte Monitoring System 14, wherein the display device is further configured to transmit the data request command to the sensor electronics unit using the second communication protocol when the remaining battery life falls below a predetermined threshold.

Analyte Monitoring System 16: An embodiment of Analyte Monitoring System 13, wherein the sensor electronics unit is configured to selectively receive one or more commands over the second communication protocol and selectively transmit data over the first communication protocol.

Analyte Monitoring System 17: An embodiment of Analyte Monitoring System 13, wherein the sensor electronics unit is further configured to send data indicative of analyte levels at predetermined time intervals.

Analyte Monitoring System 18: An embodiment of Analyte Monitoring System 17, wherein the sending of data indicative of analyte levels using the first communication protocol in response to the data request command does not interfere with the sensor electronics unit sending data indicative of analyte levels at the predetermined time intervals.

Analyte Monitoring System 19: An embodiment of Analyte Monitoring System 13, 14 or 15, wherein, when the remaining battery life falls below the predetermined threshold, the display device transmits power to the sensor electronics unit using a radio frequency field, thereby providing power to the sensor electronics unit to send data indicative of analyte levels over the second communication protocol.

Analyte Monitoring System 20: An embodiment of Analyte Monitoring System 14, wherein the sensor electronics unit is further configured to store data indicative of analyte levels on a passive tag when the remaining battery life falls below a predetermined threshold, and the display device is further configured to read the passive tag using the second communication protocol.

Analyte Monitoring System 21: An embodiment of Analyte Monitoring System 13, wherein the sensor electronics unit further sends a decryption key using the second communication protocol in response to the data request command, and the decryption key is used to decrypt the data indicative of analyte levels sent using the first communication protocol in response to the data request command.

Analyte Monitoring System 22: An analyte monitoring system, comprising: a sensor configured to take measurements indicative of analyte levels; a sensor electronics unit communicatively coupled to the sensor, wherein the sensor electronics unit is configured to: receive the measurements indicative of analyte levels from the sensor and calculate estimated analyte values, transmit the estimated data indicative of analyte levels using a first communication protocol, and receive commands using a second communication protocol; and a display device configured to: receive data indicative of analyte levels using the first communication protocol, and transmit a data request command to the sensor electronics unit using the second communication protocol, wherein the sensor electronics unit sends a portion of the data indicative of analyte levels using the first communication protocol and another portion of the data indicative of analyte levels using the second communication protocol in response to the data request command.

Analyte Monitoring System 23: An embodiment of Analyte Monitoring System 22, wherein the sensor electronics unit is further configured to measure a remaining battery life of the sensor electronics unit.

Analyte Monitoring System 24: An embodiment of Analyte Monitoring System 22 or 23, wherein the sensor electronics unit is further configured to cease transmission of data indicative of analyte levels when the measured remaining battery life falls below a predetermined threshold.

Analyte Monitoring System 25: An embodiment of Analyte Monitoring System 23, wherein the sensor electronics unit is further configured to utilize the low power mode when the measured remaining battery life falls below a predetermined low power mode threshold.

Analyte Monitoring System 26: An embodiment of Analyte Monitoring System 23, 24, or 25, wherein the sensor electronics unit is further configured to utilize the normal power mode when the measured remaining battery life is above a predetermined normal power mode threshold.

Analyte Monitoring System 27: An embodiment of Analyte Monitoring System 22 wherein the second communication protocol utilizes at least one of near field communication and radio-frequency identification.

Analyte Monitoring System 28: An embodiment of Analyte Monitoring System 22, wherein the sensor electronics unit is further configured to calculate estimated analyte levels based at least in part on the measurements.

Analyte Monitoring System 29: An embodiment of Analyte Monitoring System 22 wherein the display device is further configured to calculate estimated analyte values based at least in part on the measurements.

Analyte Monitoring System 30: An embodiment of Analyte Monitoring System 22, wherein, after a device authentication procedure has been completed, the display device is further configured to read calibration or manufacturing information from a passive tag incorporated into the sensor electronics unit.

Analyte Monitoring System 31: An embodiment of Analyte Monitoring System 30, wherein at least a portion of the information read from the passive tag is encrypted.

In some implementations, a computing system that has components including a central processing unit ("CPU"), input/output ("I/O") components, storage, and memory can be used to execute the monitoring system, or specific components and/or subcomponents of the monitoring system. The executable code modules of the monitoring system can be stored in the memory of the computing system and/or on other types of non-transitory computer-readable storage media. In some implementations, monitoring system can be configured differently than described above.

Each of the processes, methods, and algorithms described in the preceding sections can be embodied in, and fully or partially automated by, code modules executed by one or more computers, computer processors, or machines configured to execute computer instructions. The code modules can be stored on any type of non-transitory computer-readable medium or tangible computer storage device, such as hard drives, solid state memory, optical disc, and/or the like. The systems and modules can also be transmitted as generated data signals (e.g., as part of a carrier wave or other analog or digital propagated signal) on a variety of computer-readable transmission mediums, including wireless-based and wired/cable-based mediums, and can take a variety of forms (e.g., as part of a single or multiplexed analog signal, or as multiple discrete digital packets or frames). The processes and algorithms can be implemented partially or wholly in application-specific circuitry. The results of the disclosed processes and process steps can be stored, persistently or otherwise, in any type of non-transitory.

As used herein, the term module or unit might describe a given unit of functionality that can be performed in accordance with one or more implementations of the present application. As used herein, a module or unit might be implemented utilizing any form of hardware, software, or a combination thereof. For example, one or more processors, controllers, ASICs, PLAs, PALs, CPLDs, FPGAs, logical components, software routines or other mechanisms might be implemented to make up a module or unit. The modules, units, circuitry, processors, etc. may be affixed to a printed circuit board (PCB), or the like, and may take a variety of forms. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

The various features and processes described above can be used independently of one another, or can be combined in various ways. All possible combinations and sub-combinations are intended to fall within the scope of this disclosure. In addition, certain method or process blocks can be omitted in some implementations. The methods and processes described herein are also not limited to any particular sequence, and the blocks or states relating thereto can be performed in other sequences that are appropriate. For example, described tasks or events can be performed in an order other than that specifically disclosed, or multiple can be combined in a single block or state. The example tasks or events can be performed in serial, in parallel, or in some other manner. Tasks or events can be added to or removed from the disclosed example implementations. The example systems and components described herein can be configured differently than described. For example, elements can be added to, removed from, or rearranged compared to the disclosed example implementations.

Conditional language used herein, such as, among others, "can," "could," "might," "may," "e.g.," and the like, is not generally intended to imply that features, elements and/or steps are required for one or more implementations or that one or more implementations necessarily include logic for deciding, with or without author input or prompting, whether these features, elements and/or steps are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. can be either X, Y or Z. Thus, such conjunctive language is not generally intended to imply that certain implementations require at least one of X, at least one of Y and at least one of Z to each be present. The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value. Also, as used herein "defined" can include "predefined" and/or otherwise determined values, conditions, thresholds, measurements, and the like.

While certain example implementations have been described, these implementations have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein can be embodied in a variety of other forms; furthermore, various omissions, substitutions and changes in the form of the methods and systems described herein can be made without departing from the spirit of the inventions disclosed herein.

What is claimed is:

1. An analyte monitoring system, comprising:
   an analyte sensor configured to generate sensor data indicative of analyte levels;
   a sensor electronics unit communicatively connectable to the analyte sensor, wherein the sensor electronics unit is configured to:
      process the sensor data indicative of analyte levels from the analyte sensor to generate sensor information,
      transmit a first portion of the sensor information using a first communication protocol, and
      receive one or more commands and respond to the one or more commands using a second communication protocol; and
   a display device configured to:
      receive the first portion of the sensor information using the first communication protocol,
      present a user interface for user selection of at least one of the one or more commands,
      receive a selection of at least one of the one or more commands from a user,
      transmit the selected at least one of the one or more commands to the sensor electronics unit using the second communication protocol, and
      receive at least a second portion of the sensor information using the second communication protocol in response to the selected at least one of the one or more commands;
   wherein the first communication protocol uses a Bluetooth transceiver; and
   wherein the second communication protocol uses a Near Field (NFC) Communication transceiver.

2. The analyte monitoring system of claim 1, wherein the sensor electronics unit is further configured to calculate estimated analyte levels based at least in part on the generated sensor data.

3. The analyte monitoring system of claim 1, wherein the display device is further configured to calculate estimated analyte values based at least in part on the generated sensor data.

4. The analyte monitoring system of claim 1, wherein the display device is further configured to read sensor calibration or manufacturing information from the sensor electronics unit.

5. The analyte monitoring system of claim 4, wherein at least a portion of the information is encrypted and is read from a passive tag.

6. The analyte monitoring system of claim 1, wherein the first communication protocol has a first communication range and the second communication protocol has a second communication range, and wherein the second communication range is shorter than the first communication range.

7. The analyte monitoring system of claim 1, wherein the selected at least one of the one or more commands is a retrieve data command.

8. The analyte monitoring system of claim 1, wherein the display device is configured to present a user interface displaying information associated at least with the second portion of the sensor information received from the sensor electronics unit.

9. The analyte monitoring system of claim 1, wherein the display device is configured to present an alarm based at least in part on the first portion of the sensor information received from the sensor electronics unit.

10. The analyte monitoring system of claim 1, wherein the display device is a mobile phone or a medical receiver.

11. In an analyte monitoring system comprising an analyte sensor configured to generate sensor data indicative of analyte levels, a sensor electronics unit communicatively connectable to the analyte sensor, and a display device, a method of using the system to monitor analyte levels of a subject, the method comprising:
   transcutaneously implanting the analyte sensor;
   selecting a wake command for the sensor electronics unit;
   waking up the sensor electronics unit from a low power mode by transmitting the selected wake command from the display device to the sensor electronics unit via a first communication protocol, wherein the first communication protocol uses a Near Field Communication (NFC) transceiver;
   selecting a retrieve data command for the sensor electronics unit;
   retrieving sensor data from the sensor electronics unit by transmitting the selected retrieve data command from the display device to the sensor electronics unit via the first communication protocol;
   establishing a communication channel via a second communication protocol between the sensor electronics unit and the display device, wherein the second communication protocol uses a Bluetooth transceiver; and
   transmitting sensor data from the sensor electronics unit to the display device via the second communication protocol;
   wherein the retrieved sensor data via the first communication protocol is being used to display information associated with the sensor data on the display device, and wherein the sensor data transmitted via the second communication protocol is being used to generate alarms on the display device.

12. The method of claim 11, wherein the first communication protocol has a range of 10 cm or less, and wherein the second communication protocol has a range of 30 feet or more.

13. The method of claim 11, wherein the low power mode is a sleep mode or a shelf mode.

14. The method of claim 11, comprising holding the display device within 10 cm of the sensor electronics unit when transmitting the wake command from the display device.

15. The method of claim 11, wherein the establishment of the communication channel via the second communication protocol includes using authentication information related to the sensor electronics unit.

16. The method of claim 11, wherein the first communication protocol has a first communication range, wherein the second communication protocol has a second communication range longer range than the first communication range.

* * * * *

UNITED STATES PATENT AND TRADEMARK OFFICE
CERTIFICATE OF CORRECTION

PATENT NO. : 10,980,451 B2
APPLICATION NO. : 17/027418
DATED : April 20, 2021
INVENTOR(S) : Wedekind et al.

It is certified that error appears in the above-identified patent and that said Letters Patent is hereby corrected as shown below:

On the Title Page

On page 3, in Column 2, item (56), U.S. Patent Documents, Line 17, delete "1,037,618" and insert -- 10,376,188 --.

On page 3, in Column 2, item (56), U.S. Patent Documents, Line 18, delete "1,056,134" and insert -- 10,561,349 --.

On page 3, in Column 2, item (56), U.S. Patent Documents, Line 19, delete "1,056,855" and insert -- 10,568,552 --.

On page 6, in Column 1, item (56), Other Publications, Line 6, below "commucation" and insert -- communication --.

In the Specification

In Column 9, Lines 20-21, delete "andrenostenedione;" and insert -- androstenedione; --.

In Column 9, Line 25, delete "1-13" and insert -- 1-β --.

In Column 9, Lines 36-37, delete "diptheria" and insert -- diphtheria --.

In Column 9, Line 39, delete "13-human" and insert -- β-human --.

In Column 9, Line 43, delete "perioxidase;" and insert -- peroxidase; --.

In Column 9, Lines 52-53, delete "sissomicin;" and insert -- sisomicin; --.

In Column 9, Line 57, delete "duodenalisa," and insert -- duodenalis, --.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,980,451 B2

In Column 9, Line 63, delete "Rickettsia" and insert -- rickettsia --.

In Column 9, Lines 64-65, delete "Trepenoma pallidium," and insert -- Treponema pallidum, --.

In Column 9, Line 66, delete "stomatis" and insert -- stomatitis --.

In Column 10, Line 36, delete "(FHIAA)." and insert -- (5-HIAA). --.

In Column 10, Line 42, delete "disclosure)." and insert -- disclosure. --.

In Column 21, Line 8, delete "or and" and insert -- and/or --.

In Column 30, Line 33, delete "Internet" and insert -- internet --.

In Column 44, Line 42, delete "demand" and insert -- demand. --.

In Column 62, Line 21, delete "where as" and insert -- whereas --.

In the Claims

In Column 70, Line 67, Claim 1, delete "(NFC) Communication" and insert -- Communication (NFC) --.